US008602780B2

(12) United States Patent
Rubbert

(10) Patent No.: US 8,602,780 B2
(45) Date of Patent: Dec. 10, 2013

(54) CUSTOMIZED DENTAL PROSTHESIS FOR PERIODONTAL OR OSSEOINTEGRATION AND RELATED SYSTEMS AND METHODS

(75) Inventor: Ruedger Rubbert, Berlin (DE)

(73) Assignee: Natural Dental Implants, AG, Berlin (DE)

( * ) Notice: Subject to any disclaimer, the term of this patent is extended or adjusted under 35 U.S.C. 154(b) by 549 days.

(21) Appl. No.: 12/763,001

(22) Filed: Apr. 19, 2010

(65) Prior Publication Data

US 2010/0203478 A1 Aug. 12, 2010

Related U.S. Application Data

(63) Continuation-in-part of application No. 11/724,261, filed on Mar. 15, 2007, now Pat. No. 7,708,557, which is a continuation-in-part of application No. 11/549,782, filed on Oct. 16, 2006, now Pat. No. 8,454,362.

(51) Int. Cl.
*A61C 8/00* (2006.01)
(52) U.S. Cl.
USPC ........................................................ 433/173
(58) Field of Classification Search
USPC .............. 433/172–176, 191–195; 700/95–98; 703/2, 6–7
See application file for complete search history.

(56) References Cited

U.S. PATENT DOCUMENTS 2,721,387 A   10/1955   Ashuckian
2,792,628 A    5/1957   Neumayer
3,628,248 A   12/1971   Kroder
3,717,932 A *  2/1973   Brainin .......................... 433/175
3,984,914 A   10/1976   Schwartz
4,178,686 A   12/1979   Riess et al.
4,199,864 A    4/1980   Ashman (Continued)

FOREIGN PATENT DOCUMENTS

CA   2624830 A1   4/2007
DE   2729969 A1   1/1978

(Continued)

OTHER PUBLICATIONS

Office Action from co-pending U.S. Appl. No. 11/549,782, filed Feb. 7, 2012.

(Continued)

*Primary Examiner* — Robyn Doan
*Assistant Examiner* — Matthew Nelson
(74) *Attorney, Agent, or Firm* — Bracewell & Giuliani LLP

(57) ABSTRACT

Dental prosthesis, systems, and methods of forming and using a dental prosthesis, are provided. An example of a dental prosthesis includes a first manufactured portion shaped to substantially conform to the three-dimensional surface of a root of a tooth to be replaced and a second manufactured portion shaped to substantially conform to the three-dimensional surface of a crown of the tooth. Furthermore, customized manufactured splints to position and fixate a tooth-shaped prosthesis, are provided. Furthermore, a CAD/CAM based methods of and a systems for manufacturing a customized dental prosthesis are provided. The tooth can be scanned to determine its three-dimensional shape and substantially copied using an imaging system in-vitro like a 3D scanner or in-vivo like a cone beam CT system and CNC machinery. Biocompatible material that is suitable to be integrated into the extraction socket and adopted by existing tissue forming the socket can be manufactured or engineered.

11 Claims, 29 Drawing Sheets

(56) References Cited

U.S. PATENT DOCUMENTS

| | | | |
|---|---|---|---|
| 4,278,630 A | 7/1981 | Scheicher | |
| 4,504,229 A | 3/1985 | Garito | |
| 4,552,779 A * | 11/1985 | McClure | 433/191 |
| 4,684,555 A | 8/1987 | Neumeyer | |
| 4,828,117 A | 5/1989 | Panzera et al. | |
| 5,002,488 A | 3/1991 | Homsy | |
| 5,061,285 A | 10/1991 | Koch | |
| 5,094,618 A | 3/1992 | Sullivan | |
| 5,108,289 A | 4/1992 | Fukuyo | |
| 5,123,844 A | 6/1992 | Wakai | |
| 5,264,215 A * | 11/1993 | Nakabayashi et al. | 424/423 |
| 5,562,450 A | 10/1996 | Gieloff | |
| 5,691,905 A | 11/1997 | Dehoff | |
| 5,725,376 A | 3/1998 | Poirier | |
| 5,725,378 A | 3/1998 | Wang | |
| 5,772,439 A | 6/1998 | Yamaoka | |
| 5,800,175 A | 9/1998 | Zuk | |
| 5,921,778 A * | 7/1999 | Karmaker et al. | 433/215 |
| 6,089,867 A | 7/2000 | Filho | |
| 6,099,313 A | 8/2000 | Dorken | |
| 6,186,790 B1 | 2/2001 | Karmaker | |
| 6,193,516 B1 | 2/2001 | Story | |
| 6,250,923 B1 | 6/2001 | Gibbs et al. | |
| 6,436,143 B1 | 8/2002 | Ross | |
| 6,447,295 B1 | 9/2002 | Kumar et al. | |
| 6,521,246 B2 | 2/2003 | Sapieszko | |
| 6,534,197 B2 | 3/2003 | Noda et al. | |
| 6,589,625 B1 | 7/2003 | Kothari et al. | |
| 6,696,073 B2 * | 2/2004 | Boyce et al. | 424/422 |
| 6,702,855 B1 | 3/2004 | Steinemann et al. | |
| 6,755,651 B2 | 6/2004 | Brodbeck | |
| 6,788,986 B1 | 9/2004 | Traber et al. | |
| 6,863,694 B1 | 3/2005 | Boyce | |
| 6,913,666 B1 | 7/2005 | Aeschlimann | |
| 6,921,264 B2 | 7/2005 | Mayer | |
| 6,955,540 B2 | 10/2005 | Mayer | |
| 6,984,261 B2 | 1/2006 | Cummings et al. | |
| 7,008,226 B2 | 3/2006 | Mayer | |
| 7,105,182 B2 | 9/2006 | Szymaitis | |
| 7,110,594 B2 | 9/2006 | Jones | |
| 7,156,655 B2 | 1/2007 | Sachdeva | |
| 7,234,937 B2 | 6/2007 | Sachdeva | |
| 7,333,874 B2 | 2/2008 | Taub | |
| 7,377,782 B1 * | 5/2008 | Brosnihan | 433/215 |
| 7,708,557 B2 | 5/2010 | Rubbert | |
| 7,774,048 B2 | 8/2010 | Nakaoka et al. | |
| 7,813,806 B2 | 10/2010 | Skiba | |
| 7,904,307 B2 | 3/2011 | Abolfathi et al. | |
| 2001/0055745 A1 * | 12/2001 | Gault | 433/201.1 |
| 2002/0015934 A1 | 2/2002 | Rubbert et al. | |
| 2002/0102009 A1 | 8/2002 | Jones et al. | |
| 2002/0140137 A1 | 10/2002 | Sapieszko et al. | |
| 2003/0064349 A1 | 4/2003 | Simmons | |
| 2003/0118968 A1 | 6/2003 | Massoud | |
| 2004/0015327 A1 | 1/2004 | Sachdeva et al. | |
| 2004/0038178 A1 | 2/2004 | Mayer et al. | |
| 2004/0053198 A1 | 3/2004 | Minevski et al. | |
| 2004/0110110 A1 * | 6/2004 | Chishti et al. | 433/24 |
| 2004/0152034 A1 | 8/2004 | Cummings et al. | |
| 2004/0168610 A1 | 9/2004 | Conrad et al. | |
| 2004/0185418 A1 | 9/2004 | Schulter | |
| 2004/0197727 A1 * | 10/2004 | Sachdeva et al. | 433/24 |
| 2005/0033427 A1 | 2/2005 | Freilich | |
| 2005/0038498 A1 * | 2/2005 | Dubrow et al. | 623/1.15 |
| 2005/0048440 A1 | 3/2005 | Feng | |
| 2005/0079469 A1 | 4/2005 | Akagawa et al. | |
| 2005/0084513 A1 | 4/2005 | Tang | |
| 2005/0106534 A1 | 5/2005 | Gahlert | |
| 2005/0142517 A1 | 6/2005 | Frysh | |
| 2005/0186540 A1 | 8/2005 | Taub et al. | |
| 2005/0260541 A1 | 11/2005 | McDevitt | |
| 2006/0003292 A1 | 1/2006 | Lauren | |
| 2006/0078847 A1 * | 4/2006 | Kwan | 433/174 |
| 2006/0105295 A1 * | 5/2006 | Mayer et al. | 433/173 |
| 2006/0154203 A1 | 7/2006 | Emanuelli | |
| 2007/0015110 A1 | 1/2007 | Zhang et al. | |
| 2007/0072152 A1 | 3/2007 | Jaghab | |
| 2007/0154866 A1 | 7/2007 | Hall | |
| 2007/0264612 A1 | 11/2007 | Mount | |
| 2008/0090207 A1 | 4/2008 | Rubbert | |
| 2008/0090208 A1 | 4/2008 | Rubbert | |
| 2008/0213725 A1 | 9/2008 | Adilstam et al. | |
| 2009/0042167 A1 | 2/2009 | Van Der Zel | |
| 2009/0087817 A1 | 4/2009 | Jansen | |
| 2010/0203478 A1 | 8/2010 | Rubbert | |
| 2010/0261141 A1 | 10/2010 | Ajlouni | |
| 2011/0010187 A1 | 1/2011 | Andersson et al. | |

FOREIGN PATENT DOCUMENTS

| | | |
|---|---|---|
| DE | 197 53 577 A1 | 6/1999 |
| DE | 10020894 A1 | 4/2000 |
| DE | 10109118 A1 | 9/2002 |
| DE | 103 58 680 A1 | 7/2005 |
| EP | 0053903 A1 | 6/1982 |
| EP | 0053903 B1 | 4/1987 |
| EP | 1073381 | 4/1999 |
| EP | 1150620 | 1/2000 |
| EP | 1150620 B1 | 5/2003 |
| EP | 1073381 B1 | 9/2004 |
| EP | 2 025 303 A1 | 2/2009 |
| EP | 2087852 A1 | 8/2009 |
| EP | 2087853 A1 | 8/2009 |
| EP | 2095789 A1 | 9/2009 |
| JP | 95014400 | 2/1995 |
| WO | WO 0134056 A1 | 5/2001 |
| WO | WO 2004056405 A2 | 7/2004 |
| WO | WO 2005057439 A1 | 6/2005 |
| WO | WO 2005105164 A1 | 11/2005 |
| WO | WO 2006031096 A1 | 3/2006 |
| WO | WO 2006060836 A1 | 6/2006 |
| WO | WO 2007006258 A1 | 1/2007 |
| WO | WO 2007038817 A1 | 4/2007 |
| WO | 2007131337 A1 | 11/2007 |
| WO | WO 2007125323 A1 | 11/2007 |
| WO | 2008017472 A1 | 2/2008 |
| WO | WO 2008047204 A2 | 4/2008 |
| WO | WO2009020447 A1 | 12/2009 |

OTHER PUBLICATIONS

Berndt et al., "Topologically Structured Surfaces and Coating Treatments for Peridontal and Osseo-Integration", Natural Dental Implants AG (2009), pp. 1-5.

Barsch, "Verbesserung des Haftverbundes fur Vollkeramikkronen aus Y-TZP durch Femtosekundenlaser-Mikrostrukturierung", 35 (10) Quintessenz Zahntech (2009), pp. 1322-1332.

Spouge, "Oral Pathology", The C.V. Mosby Co., Saint Louis (1973).

Vannier, "Craniofacial computed tomography scanning: technology, applications and future trends",. 6 (Suppl 1) Orthod. Craniofacial Res. (2003), pp. 23-30.

"Introduction to Digital Dentistry and Guided Surgery", 3D Diagnostix.com, http://www.3ddx.com/guided_surgery.htm [Oct. 7, 2011 7:21:51 PM].

Christensen et al., "Role of Rapid Digital Manufacture in Planning and Implementation of Complex Medical Treatments", from Advanced Manufacturing Technology for Medical Applications: Reverse Engineering, Software Conversion and Rapid Prototyping, I. Gibson (Edi.), John Wiley & Sons, Ltd. (2005), pp. 15-30.

Ganz, "Use of Conventional CT and Cone Beam for Improved Dental Diagnostics and Implant Planning", Amer. Assoc. of Dental Radiographic Technicians Newsletter (Spring 2005), http://aadmrt.com/currents/ganz_spring_2005_print.htm [Oct. 18, 2011 2:22:24 PM].

Hatcher, "Cone Beam CT for Pre-Surgical Assessment of Implant Sites", Amer. Assoc. of Dental Radiographic Technicians Newsletter (Summer 2005).

Partial File History of U.S. Appl. No. 11/562,953 (Hall), filed Nov. 22, 2006.

"Materialise Scores Against Nobel Biocare: More Changes Looming in the Surgical Guide Market?", http://www.osseonews.com/materialise-against-nobel-biocare/print/[Oct. 17, 2011 7:41:51 PM].

(56) References Cited

OTHER PUBLICATIONS

Ganz, Use of Stereolithographic Models as Diagnostic and restorative Aids for predictable Immediate Loading of Implants, 15(10) Pract. Proced. Aesthet. Dent. (2003), pp. 763-771.
Dakhno, Abstract—"Maxillolofacial surgery planning for the insertion of dental implants obtained from CT data using the SimPlant interactive software", 2(2) Implantology & Paradontology & Osteology (2005), pp. 23-27.
Mupparapu, "Implant Imaging for the Dentist", 70(1) J. Canadian Dent. Assoc. (2004), pp. 32-32g.
European Search Report for Application No. 09075154.6, dated Jul. 13, 2009.
Department of Dentistry: Research—Department of Dentistry—University of Alberta; http://www.dent.ualberta.ca/; Jan. 26, 2007 (1 page).
Partial File History of U.S. Appl. No. 11/549,782 (Rubbert), filed Oct. 16, 2006.
Int'l Prelim. Rpt. on Patentability and Written Opinion, PCT/IB2007/003072, dated Jul. 22, 2008.
Int'l Srch. Rpt, PCT/IB2007/003072, dated Oct. 16, 2007.
Partial File History of U.S. Appl. No. 13/247,843, filed Sep. 28, 2011.
Partial File History of U.S. Appl. No. 13/247,607, filed Sep. 28, 2011.
Office Action Summary, Patent Application No. 11549782, dated Mar. 24, 2011.
International Search Report for Related PCT Patent Application No. PCT/IB2007/003072, dated Oct. 16, 2007.
European Search Report for Related European Patent Application No. 09075153.8, dated Jul. 8, 2009.
European Search Report for Related European Patent Application No. 09075155.3, dated Jul. 30, 2009.
File History for Related U.S. Appl. No. 11/549,782, filed Oct. 16, 2006.
File History for Related U.S. Appl. No. 11/724,261, filed Mar. 15, 2007, now U.S. Patent 7,708,557.
European Search Report for Related European Application No. 09075154.6, dated Jul. 13, 2009.
Office Action Summary, Patent Application No. 11549752, dated Oct. 25, 2010.
Office Action of co-pending U.S. Appl. No. 11/549,782, dated Aug. 3, 2012.
E. Nuzzolese, "Intentional Dental Reimplantation: A Case Report," The Journal of Contemporary Dental Practice, vol. 5, No. 3, Aug. 15, 2004. pp. 1-7.
K. Wong, "Exarticulation and Reimplantation Utilizing Guided Tissue Regeneration: A Case Report," Quintessence International, vol. 33, No. 2, 2002, pp. 101-109.
A. Goerig, "Successful Intentional Reimplantation of Manidular Molars," Quintessence International, vol. 19, No. 8, 1988, pp. 585-588.
D. Benedict, "Reimplantation of Teeth," Quintessence International, vol. 9, 1989, pp. 41-47.
Kerr Corp., Datasheet, "Bioplant, Biocompatible, Synthetic, Osteoconductive," 2006.
A. Touchstone, "Simplifying CAS/CAM Dentistry," Dental Products Report, Nov. 2005, An Advanstar Publication, pp. 1-20.
Juxtaendo, website article,"Juxtaendo" Dentistry Implant (A. DiGiulio), downloaded from San Babila Day Hospital (Italy), Oct. 18, 2006.
Exodontia: The Ogram System, pp. 1-2, Jan. 26, 2007.
Bartold, "Tissue Engineering: A New Paradigm for Periodontal Regeneration Based on Molecular and Cell Biology," Periodontology 2000, vol. 24, pp. 253-269.
Buser, "Formation of a Periodontal Ligament Around Titanium Implants," J. Periodontal, Sep. 1990, vol. 61, No. 9, pp. 597-601.
El-Homsi, "Simultating Periodontal Effects in Dental Osseointegrated Implants: Effect of an Intramobile Damping Element on the Fatigue Strength of Dental Implants—An In Vitro Test Method," Quintessence International, vol. 35, No. 6, 2004, pp. 449-455.
Grzesik, "Cementum and Periodontal Wound Healing and Regeneration," Crit. Rev. Oral Biiol Med. 2002, vol. 13, pp. 474-484.
Lang, "Attachment Formation Following Replantation of Cultured Cells Into Periodontal Defects—A Study in Minipigs," J. Dent. Res., Feb. 1998, vol. 77, No. 2, pp. 393-405.
Lin, "Dental Implants with the Periodontium: A New Approach for the Restoration of Missing Teeth," Elsevier, Medical Hypotheses, 2009, vol. 72, pp. 58-61.
Malekzadeh, "Isolation of Human Osteoglast-Like Cells and In Vitro Amplification for Tissue Engineering," J. Periodontal, Nov. 1998, vol. 60, No. 11, pp. 1256-1262.
Mensor, "Compliant Keeper System Replication of the Periodontal Ligament Protective Damping Function for Implants," The Journal of Prosthetic Dentistry, Nov. 1998, vol. 80, No. 5, pp. 565-569.
Metzger, "Manufacturing Splints for Orthognathic Surgery Using a Three-Dimensional Printer," http:www.aadmrt.com/currents/metzgeretal_winter_09_print.htm,Apr. 8, 2009, 14 pages.
Reichert, "Tuning Cell Adhesion on PTFE Surface by Laser Induced Microstructures," Advanced Engineering Materials, 2007, vol. 9, No. 12,Wiley-VCH Verlag GmbH & Co., KGaA, Weinheim, pp. 1104-1113.
Van Dijk, "Cell-Seeding of Periodontal Ligament Fibroblasts," J. Clin Periodontal, 1991, vol. 18, pp. 196-199.
Patient Information Leaflet Orthognathic Surgery, British Orthodontic Society, 2 pages, 2003.
A. Veis, "Specific Amelogenin Gene Spice Product Have Signaling Effect on Cells in Culture and in Implants in Vivo, " The Journal of Biological Chemistry, 2000 by The American Society for Biochemistry and Molecular Biology, Inc., vol. 275, No. 52, pp. 41263-41272, Dec. 29, 2000.
F. Kawana, "Porcine Enamel Matrix Derivative Enhances Trabecular Bone Regeneration During Wound Healing of Injure Rat Femur," The Anatomical Record, 2001, vol. 264, pp. 438-446.
M. Iijima, Control of Ostacalcium Phosphate and Apatite Crystal Growth by Amelogenin Matrices, Journal of Materials Chemistry, 2004, vol. 14, pp. 2189-2199.
A.M. Hoang, "Amelogenin is a Cell Adhesion Protein," Journal of Dental Research, 2000, http://www.sagepublications.com, vol. 81(7), pp. 497-500.
L. Hammartrom, "Periodontal Regeneration in a Buccal Dehisence Model in Monkeys After Application of Enamel Matrix Proteins," Journal of Clinical Periodontal, 1997, vol. 24, pp. 669-677.
B.D. Boyan, "Porcine Fetal Enamel Matrix Derivative Enhances Bone Formation Induced by Demineralized Freeze Dried Bone Allograft in Vivo," J. Periodontal, 2000, vol. 71, No. 8, pp. 1278-1286.
A. Veis, "Amelogenin Gene Splice Products: Potential Signaling Molecules," CML Cellular and Molecular Life Sciences, Birkhauser Verlag, Basel, vol. 60 (2003), pp. 38-55.
F. Schwartz,"Effect of Enamel Matrix Protein Derivative on the Attachment, Proliferation, and Viability of Human SA0s2 Osteoblasts on Titanium Implants," Clinical Oral Investment, Springer-Verlag (2004), vol. 8, pp. 165-171.
K. Tomplins, "Two Related Low Molecular Mass Polypeptide Isoforms of Amelogenin Have Distinct Activities in Mouse Tooth Germ Differentiation In Vitro," Journal of Bone and Mineral Research, vol. 20, No. 2, 2005. pp. 341-349.
H.B. Wen, "Modulation of Apatite Crystal Growth on Bioglass by Recombinant Amelogenin," Biomaterials, vol. 20, (1999), pp. 1717-1725.
H.B. Wen, "Modification of Calcium-Phosphate Coating on Titanium by Recombinant Amelogenin," Center for Craniofacial Molecular Biology, School of Dentistry, Univ. of Southern California, 2003 Wiley Periodicals, Inc., pp. 483-490.
L. Heijl, "Periodontal Regeneration With Enamel Matrix Derivative in One Human Experimental Defect," Journal of Clinical Periodontalology, 1997, vol. 24, pp. 693-696.
A.G. Fincham, "The Structural Biology of the Developing Dental Enamel Matrix," Journal of Structural Biology, 1999, vol. 126, pp. 270-299.

(56) References Cited

OTHER PUBLICATIONS

C. Du, "Supramolecular Assembly of Amelogenin Nanospheres Into Birefringent Microribbons," Science, 2005, vol. 307, pp. 1450-1454.
Strauman, "Emdogain, The Reliable Solution for Periodontal Treatment," http//www.Straumann.com, Mar. 2006.
Warrer, "Periodontal Ligament Formation Around Different Types of Dental Titanium Implants: The Self-Tapping Screw Type Implant System," J. Periodontal, Jan. 1993, vol. 64, No. 1, pp. 29-34.
Search Report for Related Application PCT/EP2013/053246.
Non-final Office Action dated Aug. 29, 2013 for related U.S. Appl. No. 13/247,843.

* cited by examiner

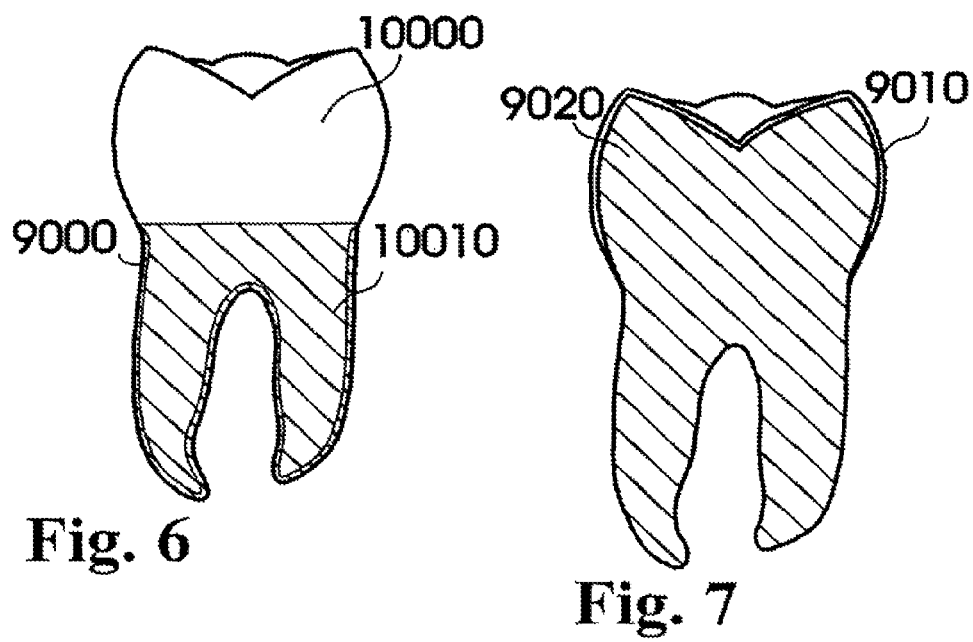
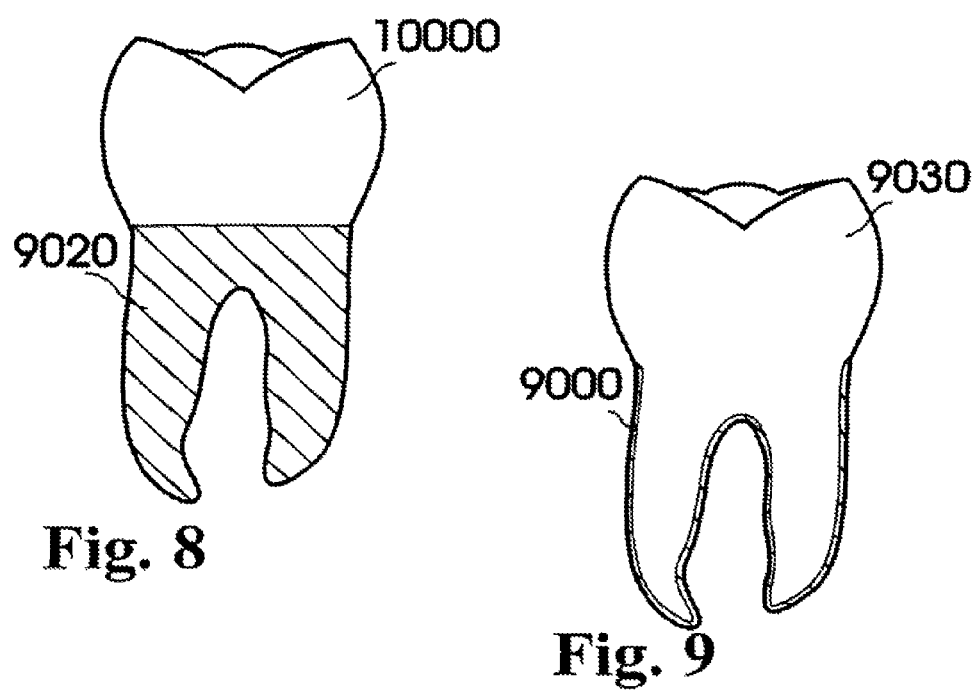

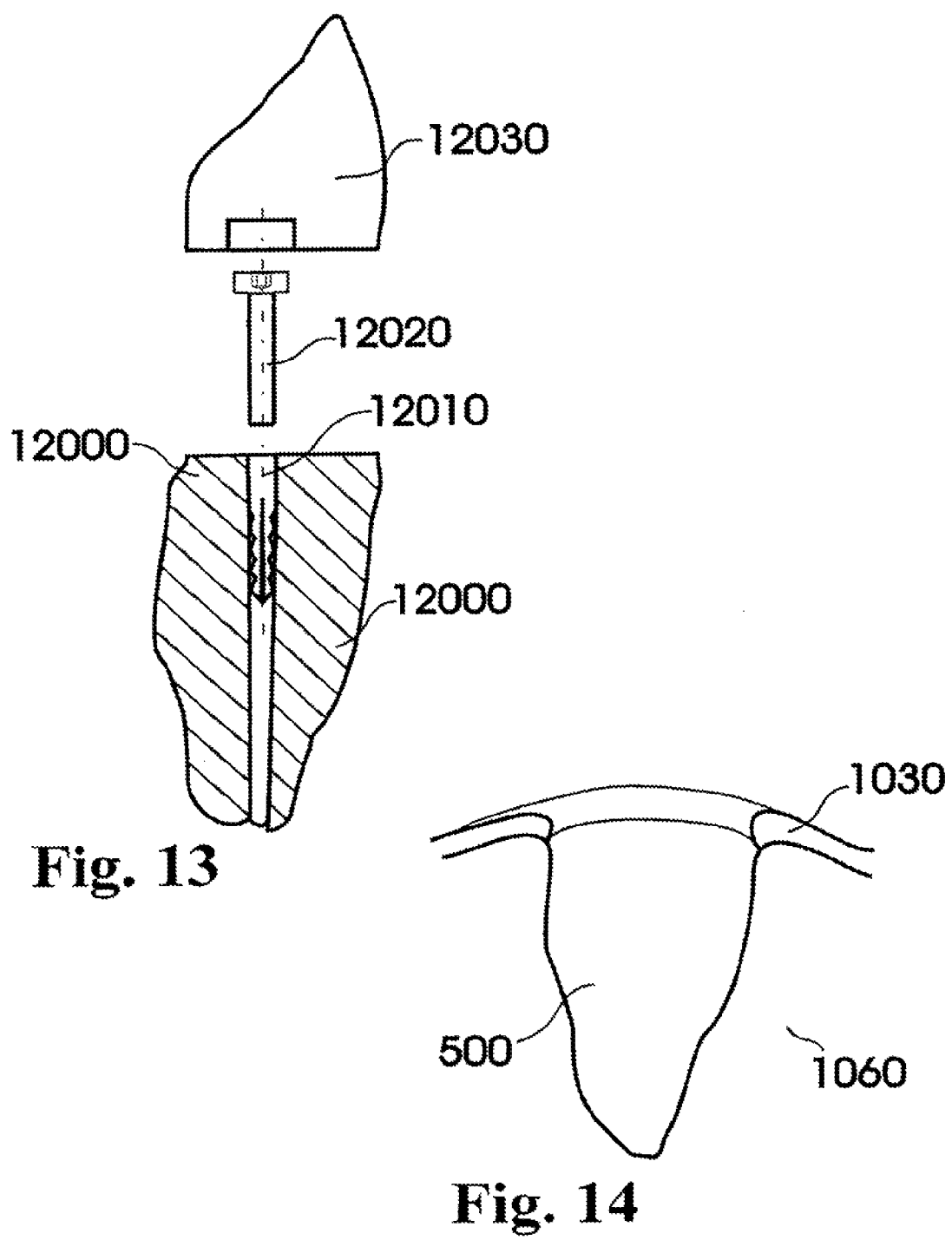

CUSTOMIZED DENTAL PROSTHESIS FOR PERIODONTAL OR OSSEOINTEGRATION AND RELATED SYSTEMS AND METHODS

RELATED APPLICATIONS

The present application is a continuation-in-part of and claims priority to and the benefit of U.S. patent application Ser. No. 11/724,261, titled "Customized Dental Prosthesis for Periodontal- or Osseointegration and Related Systems and Methods," filed on Mar. 15, 2007, and is a continuation-in-part of and claims priority to and the benefit of U.S. patent application Ser. No. 11/549,728, filed on Mar. 16, 2006, titled "Customized Dental Prosthesis for Periodontal- or Osseointegration and Related Systems and Methods," each incorporated herein by reference in its entirety.

BACKGROUND OF THE INVENTION

1. Field of the Invention

The present invention relates generally to the field of dentistry, and more particularly to the field of dental restorations, implants and prostheses. The present invention further relates to computer assisted and conventional systems and methods for designing and manufacturing such custom dental prosthesis.

2. Description of Related Art

Human teeth serve a variety of functions. Not only are they important for chewing food, but they also necessary to properly pronounce certain consonants, especially fizzle- and S-sounds. Furthermore, teeth play a major role in our personal appearance. White, healthy and well aligned teeth are an ideal of beauty and appear as a cosmetic sign of youth and success. Although various preventive measures, like frequent tooth brushing and flossing, and drinking fluoridized or iodized water are widely accepted and used, the great majority of people are sooner or later challenged with dental fillings, restorations implants, and/or prostheses. As such, a major goal in dentistry is to postpone loss of teeth as long as possible. Another goal is certainly to provide comfortable prostheses with a broad scope/indication and a long lasting life-time.

Generally, the number of available restorative and prosthetic options is limited. Typically fillings, inlays, and crowns are used if the root and its embedding periodontal structure are healthy, and sufficient as support for such restorative partial prostheses. Traditionally, if the original tooth can no longer be used, the use of bridges or non-customized osseointegrated implants, is indicated. In this context, several negative aspects are to be endured. In order to provide the support structure for a bridge, adjacent teeth are ground, and healthy enamel is partially destroyed. Osseointegrated implants are drastically invasive and the gingiva-implant interface is often the cause of chronic local infection. Additionally, all the aforementioned restorative and prosthetic options have a limited average lifetime. Removable dentures are certainly the final prosthetic option.

When a tooth is partially damaged, either by caries or mechanical impact, the missing portion should in most cases be replaced. As long as a tooth provides enough structural strength to support a dental prosthesis, such as, for example, in the form of an inlay or a crown, this will typically be the preferred solution. If the loss of tooth substance is severe, however, this may not be applicable. In these cases, a bridge can be applied, enduring the aforementioned negative consequences. Another option is to replace the tooth with an implant.

There are many methods or options for replacing missing teeth. Off-the-shelf or pre-shaped osseointegrated dental implants are one of the options. Osseointegration means the direct contact of the implant surface with the bone without a fibrous connective tissue interface (natural teeth are typically not in direct contact with the bone, but are connected to the bone by ligaments). The use of such dental implants includes a wide variety of implant designs and materials, use of implants in different locations in the mouth and use of a variety of surgical protocols.

Endosteal implants are placed into the bone, like natural tooth roots. They can provide an anchor for one or more artificial teeth, and are the most commonly used type of implants. There are various types of endosteal implants, for example, screws, cylinders, cones, plates and blades. The generic screw, cylinder and cone types of implants are sometimes called "root-form" type. Such generic root-form implants that replace a single tooth generally consist of three major parts, the actual implant-root for osseointegration, an abutment, and the artificial crown. The interfaces between the three aforementioned parts are critical in respect to the sealing quality between said three parts. Bacterial infections can be caused if the sealing is compromised in regards to its short, mid and long-term stability.

Sometimes, implant designs that actually consolidate two of said three parts, for example, the implant-root to be osseointegrated and the abutment, are referred to as one-piece implants. Contrary hereto, the term "one-piece" implant as used hereinafter is meant to refer to the integration of all three parts: the implant root, the abutment, and the crown. The term "immediate placing" of an implant is used if the integration of the implant into the bone occurs a short term after the extraction of a tooth. If such implants have a reasonable initial contact stability with the bone directly after being inserted, the so called primary stability, then such implants are called "immediately loaded", which means that the osseointegrative stability, the so called secondary stability, does not need to be developed before performing the following process steps: making an impression of the abutment part of the implant in conjunction with the gingiva and the adjacent teeth situation, then fabricating the crown, implementing the crown and actually allowing the patient to use the implant for mastication.

Subperiosteal implants are implants that are placed over the bone in cases where the bone has atrophied and jaw structure is limited. Subperiosteal implants are customized metal frameworks, providing the equivalent of multiple tooth roots. They can be applied in a limited area or in the entire mouth. After application, natural tissue membrane or bone will grow back around the implant, thus providing more stability. Posts protrude through the gum to hold the prosthesis.

Traditionally, osseointegrated dental implants are placed in bone and covered by mucosa during the immediate postoperative healing period. At four to eight months, a second surgical procedure is performed to expose the implant so it may be loaded with various types of dental crowns. In recent years, immediate implant placement following tooth extraction and immediate crown loading after surgical placement has become more common. The success rate and the in-vivo life time of osseointegrated dental implants, however, are limited, and the surgical procedure is considered heavily invasive because the bone needs to be drilled or ground in order to be adapted to the shape of the non-customized implants. Furthermore, osseointegrated implants are a limiting factor in a later orthodontic treatment. Problems relating to nerve transposition, osseous grafting, ridge augmentation, and sinus augmentation of osseointegrated dental implants, and/or to tissue health adjacent to dental implants have also been reported. Patients often complain about chronically infected periodontal structure caused by osseointegrated implants.

In cases where a tooth is not severely damaged, and would be ready to receive a partial restoration, but an intra-oral repair is impossible due to access problems, or a reverse root canal treatment is required, an alternative method is the intentional re-implantation. The tooth is extracted, repaired, and re-integrated into the existing periodontal structure of a dental patient. Nuzzolese et al write in the Journal of Contemporary Dental Practice, Volume 5, No. 3, Aug. 15, 2004: "It is well known dental reimplantation is indicated following traumatic avulsion by the preservation of cellular vitality in the periodontal ligament and under conditions of asepsis. The rate of endodontic success at five years reported in the literature ranges between 70% and 91%. As such, intentional dental reimplantation may be an effective strategy for the treatment of teeth that would be difficult, if not impossible, to treat using traditional root canal therapy. Different prognoses exist for intentional dental reimplantation and trauma-related reimplantation. This is due to such important variables such as the level of cellular vitality in the periodontal ligament; the degree of trauma to surrounding tissues, and the degree of asepsis when a tooth is removed. Surgical extraction is more favorable in this regard compared to a traumatic avulsion scenario. Although this method is not yet widely used, the reported success rates are noteworthy. Reported are also autogenous and allogenic transplantation of a healthy natural tooth into the extraction socket for parodontal/periodontal integration. A disadvantage relating to all such techniques is certainly that the specific tooth to be reimplanted or transplanted still needs an overall reasonable condition and prognosis to justify an intentional re-implantation and that only certain root and root canal deficiencies can be repaired this way.

Various publications report that the prognosis of intentional reimplanted or transplanted teeth is significantly better than the reimplantation after a traumatic extraction, since the extraction is surgically controlled and relatively aseptic techniques are utilized. Spouge writes in his Oral Pathology, Mosby, Saint Louis 1973: "The majority of reimplantations however are clinically successful, and the teeth are retained firmly in the socket for the appropriate 5 year period. However, despite the apparent success, most of them show localized ankylosis and gross resorption of the root at the end of this time. The fibrous attachment that develops in the new periodontal ligament area often involves the formation of an immature type of connective tissue whose fibers remain tangential to the root surface rather than becoming physiologically oriented. There is experimental evidence to suggest that formation of a physiologic periodontium is more easily achieved in condition where the viability of the original periodontal ligament is maintained. In keeping with this, the prognosis for clinical success in a reimplanted tooth fall rapidly if is have been completely dislocated from its socket for more than 24 hours." Wong suggests in Quintessence International, Vol. 33, No. 2, 2002, a surgical "exarticulation" method where the removal of the tooth from its socket is achieved "(after the incision of the crestal periodontal ligament fibers with micro-blades) with a combination of luxation and gentle, rotary, reciprocating movements" in order to minimize physical trauma to the excising periodontium. Goerig et al recommends in Quintessence International, Vol. 19, No. 8, 1988 a sectioning procedure where a molar tooth is cut in half dividing the roots in order to minimize the damage of the existing periodontal ligament. The Ogram System (www.ogramsystem.com) provides a tooth removal protocol promising no or very little trauma of the surrounding tissue.

El-Bialy et al from the University of Alberta, Canada reports the stimulation of jaw growth and tissue healing by directly applying ultrasound vibes to the tooth of interest. In this context, is air lake muscle writes to their leg towels yet you do teeth are muscle or Powell's 2002 pool of and/or drink water or so to account ready anything heavy it is known to those skilled in the art that the alternating "load" of dental structures in patients' day-to-day use of their dentition activates healing processes while a protection against or the avoidance of such alternating load causes resorption of roots, bone and soft tissue.

U.S. Pat. No. 5,562,450 references as prior art the German application DE 27 29 969 A1, which is incorporated herein by reference in its entirety, describing the osseintegration of an implant that is substantially a copy of an extracted human tooth fabricated by a process involving copy milling. In order to be successfully osseointegrated, the connective tissue (e.g., ligament) remaining in the extraction socket needs to be removed by being scraped out or curetted. The '450 patent recognizes the need to create a compression pressure between the bone and the implant in order to reach reasonable primary stability of the implant and teaches, therefore, to dimensionally enlarge the anatomical shape of the implant over the extracted tooth to fill the extraction socket.

U.S. Pat. No. 6,099,313 discloses a dental implant for osseointegration having a bone-contact section which is root-shaped with an apical extension and an abutment described as a build-up section for fastening a crown.

All such restorative and prosthetic options and methodologies are deficient being heavily invasive and/or limited in their respective scope. There has not been recognition, until now by the inventor, of the need for a product, systems, and methods related to the integration of dental prosthesis such as artificial tooth, bridges, or segments of the dentition that includes (a) custom-shaped root structures to be osseointegrated as one piece, (b) custom-made positioning and fixation splint for achieving primary stability, and (c) even more beneficial, parts to be integrated into the existing periodontal structure of an individual patient, having the desirable broad scope and reduced invasive requirements. There is also no prior recognition of fabricating the root-shaped custom portions of the prosthesis based on anatomical imaging data prior to the extraction of the tooth or of the teeth of interest or directly of the alveolar situation.

The product, and related systems and methods provided by the various embodiments of present invention comprise several independent inventive features providing substantial improvements to prior art. The greatest benefit will be achieved for dental treatments especially for patients requiring tooth replacement.

SUMMARY OF THE INVENTION

In view of the foregoing, various embodiments of the present invention beneficially provide a customized dental prosthesis and implant in various embodiments based on a process that includes copying a significant portion of the original root geometry of a human tooth to be integrated after extraction of the original tooth either in the existing biological cell structure of the periodontal ligament or as one piece into the embedding bone structure of the respective jaw. According to various embodiments of the present invention, primary stability is favorably achieved by a custom made splint that connects the dental prosthesis with the adjacent tooth or teeth or other dental structures like existing implants, bridges and the like. The concept of periodontal integration of an artificial tooth uses the existing human periodontal ligament for integration and is certainly less invasive than the integration of osseointegrated implants. The concept of integrating a one-piece prosthesis that includes a root-shape part, an abutment, and a crown, according to an exemplary configuration, combines the two clinical episodes of integrating the root-shaped part and adapting the crown into one clinical event. Even if such one-piece prosthesis would include an assembly of two or more parts, the assembly can be fabricated in the controlled environment of a dental laboratory or an industrial fabrication. As a result, the quality of the interface sealing between such parts can be expected to be of higher quality as produced in the mouth of the patient. This may reduce the infection rate so that the success rate of the one-piece prosthesis according to an embodiment of the present invention would be higher as achieved with implementations according to conventional systems. Further, the concept of a splint that is custom made in the laboratory in advance can serve at least two purposes: the correct positioning of the prosthesis, and the achievement of reasonable primary stability. The concept of using in-vivo imaging data in order to design and fabricate the prosthesis prior to the extraction of the tooth or teeth of interest enables a laboratory lead time prior to the invasive clinical event. The concept of using data to design a root-shaped portion or portions of the prosthesis not actually of the tooth or teeth extracted or to be extracted, but of the anatomical alveolar structure, allows an ability to adapt the prosthesis to the post-extraction or even post-surgical shape of the alveolar situation.

Any combination of the aforementioned concepts of the various embodiments of the dental prosthesis and splint can be used for efficient and/or less-invasive clinical methods according to various embodiments of the present invention. One of such clinical methods, for example, includes the immediate placement of a one-piece prosthesis allowing immediate loading. In another embodiment of the present invention, these concepts can be combined with methods of ultrasonic or other vibrations applied to the prosthesis or adjacent tooth/teeth after placement in order stimulate bone and tissue healing. In another embodiment of the present invention, the extraction of the tooth might be performed using ultrasonic or other vibrations applied to the tooth of interest to facilitate the extraction.

According to an embodiment of the present invention, an example of a method of manufacturing a dental prosthesis for implantation into a jaw bone cavity of a pre-identified patient includes the steps of receiving imaging data describing a three-dimensional shape of an outer surface portion of a root portion of a nonfunctional natural tooth of a pre-identified patient, deriving digital design data defining a three-dimensional shape of an outer surface of a root portion of a tooth prosthesis responsive to the received imaging data, and manufacturing the root portion of the tooth prosthesis at least partially responsive to the digital design data to form at least a substantial portion of the root portion of the tooth prosthesis. According to an exemplary configuration, the three-dimensional shape of the outer surface of the root portion of the tooth prosthesis defined by the derived a digital design data dimensionally matches the three-dimensional shape of a corresponding outer surface portion of the natural tooth of the pre-identified patient. Correspondingly, the three-dimensional shape of the at least a substantial portion of the outer surface portion of the root portion of the tooth prosthesis substantially produced by the manufacturing step correspondingly can also advantageously dimensionally match the three-dimensional shape of the corresponding outer surface portion of the root portion of the nonfunctional natural tooth described by the imaging data.

According to an embodiment of the present invention, the method can also include the steps of receiving imaging data describing a three-dimensional shape of an outer surface portion of a crown portion of the nonfunctional natural tooth of the pre-identified patient, deriving digital data defining a three-dimensional shape of an outer surface of a permanent crown portion of the tooth prosthesis responsive to the received imaging data, and manufacturing the crown portion of the tooth prosthesis at least partially responsive to the digital data defining the three-dimensional shape of the outer surface of the permanent crown portion of the tooth prosthesis to form at least substantial portions of a crown portion body of the crown portion of the tooth prosthesis. According to a exemplary configuration, the three-dimensional shape of the outer surface of the crown portion of the tooth prosthesis defined by the digital data dimensionally matches the corresponding three-dimensional shape of a corresponding outer surface portion of the natural tooth of the pre-identified patient; and the at least substantial portions of the crown portion body substantially matches the three-dimensional shape of a corresponding outer surface portion of the crown portion of the nonfunctional natural tooth of the pre-identified patient described by the respective imaging data.

According to an embodiment of the present invention, such as, for example, an embodiment whereby a root portion body of the dental prosthesis is configured to be at least substantially adhesively held by the periodontal ligament structure adjacent the jaw bone cavity and at least not substantially held by direct bone integration with alveolar bone tissue adjacent the jaw bone cavity when substantially integrated into and adopted by the periodontal ligament structure, the outer surface portion of the root portion of the tooth prosthesis is sized so that the three-dimensional shape thereof does not exceed dimensionally a natural three-dimensional shape of the outer surface of the root portion of the nonfunctional tooth that corresponds to an embedding outer surface of the jawbone cavity, and/or a natural pre-insertion three-dimensional shape of the embedding jaw bone cavity surface when the tooth prosthesis is clinically positioned therein.

According to an embodiment of the method, the three-dimensional shape of the at least substantial portions of the root portion of the tooth prosthesis can be initially undersized approximately 0.2 to 0.3 mm with respect to the jaw bone cavity, and the root portion of the dental prosthesis includes applying to the at least substantial portions of the root portion of the tooth prosthesis, a layer of mineral trioxide aggregate having a thickness of between approximately 0.2 to 0.3 mm to substantially match the undersize of the root shape.

According to an embodiment of the present invention, the step of manufacturing the root portion of the tooth prosthesis can include the step of applying a layer of biocompatible material to an outer surface portion of a main body portion of the root portion of the tooth prosthesis, e.g., performed prior to insertion of the root portion of the tooth prosthesis into a jaw bone cavity of the pre-identified patient. The respective biocompatible material can include, for example, engineered tissue comprising non-autologous tissue-engineered material and/or autologous tissue-engineered material, cells of a tooth comprising ancestral cells, animal cells, and/or human cells, a matrix protein derivative, a growth protein, a layer of cement, a cement material comprising a layer of between approximately 0.05 mm and 0.2 mm of a resin-modified glass ionomer cement, a glass ionomer cement comprising a calcium-alumino-silicate glass powder and an aqueous solution of an acrylic acid homo- or co-polymer, a layer of mineral trioxide aggregate, a light-activated resin-modified glass ionomer cement, a calcium hydroxide cement, and/or a drug release coating or an antibiotic pharmaceutical, or various combinations thereof.

According to an embodiment of the present invention, the step of manufacturing the root portion of the tooth prosthesis can also or alternatively include the steps of applying a first layer of biocompatible material to outer surface portions of a main body portion of the root portion of the tooth prosthesis, and applying a second layer of biocompatible material atop the first layer of biocompatible material, performed, according to an exemplary embodiment of the method, prior to insertion of the root portion of the tooth prosthesis into a jaw bone cavity of the pre-identified patient. According to a specific example of an embodiment of the method, the first layer includes a calcium hydroxide (Ca(OH)2) cement and a second layer includes a matrix protein derivative. Further, according to this exemplary embodiment of the method, the portions of the root portion comprising the first and the second layers of biocompatible material that correspond to the jaw bone cavity in its entirety do not dimensionally exceed a natural pre-insertion three-dimensional shape of portions of the jaw bone cavity receiving the tooth prosthesis when the tooth prosthesis is clinically positioned in the jaw bone cavity of the pre-identified patient. This advantageously can reduce occurrences of atrophy caused by a chronic pressure exerted on the surrounding tissue inherent with prosthetic systems which employ a "press-fit" methodology of securing the tooth prosthesis within the jaw bone cavity.

According to an embodiment of the present invention, the step of manufacturing the root portion of the tooth prosthesis can also or alternatively include the steps of applying a gel adapted to form a barrier membrane when sprayed with water to enhance tissue growth to outer surface portions of the root portion of the tooth prosthesis adjacent the permanent crown portion connected thereto, and/or applying a layer of silver to outer surface portions of the root portion of the tooth prosthesis adjacent a permanent crown portion connected thereto to reduce healing gum tissue growth during integration into and adoption by the periodontal ligament structure.

According to an embodiment of the present invention, the step of manufacturing the root portion of the tooth prosthesis can also or alternatively include the steps of employing a rapid prototyping process performed by a computer numerical control (CNC) based rapid prototyping apparatus to form the at least a substantial portion of the root portion of the tooth prosthesis. Particularly, the step can include depositing material to form the at least a substantial portion of the root portion of the tooth prosthesis layer-by-layer in a plurality of layers, whereby each layer has an edge in accordance with the digital design data, with the layers being stacked to thereby form a solid object shaped to conform to a three-dimensional surface defined by the digital design data. The rapid prototyping process can also or alternatively include selectively hardening material to form the at least a substantial portion of the root portion of the tooth prosthesis, layer-by-layer, in a plurality of layers, with each layer having an edge in accordance with the digital design data and being stacked to thereby form a solid object shaped to conform to a three-dimensional surface defined by the digital design data. The rapid prototyping process can also or alternatively include selectively combining granular material to form the at least a substantial portion of the root portion of the tooth prosthesis. According to an exemplary configuration, the rapid prototyping process can also include manufacturing the root portion and the crown portion of the tooth prosthesis together to form a substantially unitary structure. Alternatively, the step of manufacturing the root portion can include shaping at least a substantial portion of the root portion and a crown portion of the tooth prosthesis from a single block of the body material to form a substantially unitary structure.

According to an embodiment of the method, the step of deriving digital design data includes the steps of converting at least a portion of the imaging data into a computer-aided design (CAD) and/or computer-aided manufacturing (CAM) format defining a converted three-dimensional shape data, and forming a virtual three-dimensional model of the at least a substantial portion of the root portion of the nonfunctional natural tooth of the pre-identified patient responsive to the converted three dimensional shape data. Correspondingly, the step of manufacturing the root portion of the tooth prosthesis representing at least a substantial portion of the virtual three-dimensional model comprises employing a CNC-based rapid prototyping apparatus.

According to an embodiment of the present invention, the method further or alternatively includes the step of manufacturing a custom-shaped dental splint to provide temporary primary stability to the tooth prosthesis in a final geometrical relation to the embedding portion of the jawbone cavity of the pre-identified patient. The splint-manufacturing process can include the steps of receiving imaging data describing a three-dimensional shape and position of an outer surface portion of a crown portion of at least one adjacent tooth immediately adjacent the jawbone cavity of the pre-identified patient and geometrical relation thereto, and/or receiving imaging data describing a three-dimensional shape and position of outer surface portions of a crown portion of at least one opponent tooth immediately adjacent the jawbone cavity of the pre-identified patient and geometrical relation thereto. The splint-manufacturing process can also include the steps of deriving digital data forming a virtual model defining a custom-shaped splint design of the splint having an elongate tooth-surface contoured body including a tooth-facing outer surface, a non-tooth-facing outer surface opposite the tooth-facing surface, and an outer perimeter surface extending therebetween, and manufacturing the custom-shaped splint at least partially responsive to the derived digital data defining the custom-shaped splint design to form at least a substantial portion of the splint.

According to an example of a configuration of the splint, the tooth-facing outer surface can include a first three-dimensional shape portion dimensioned to substantially match to a three-dimensional shape of a corresponding substantial surface portion of the crown portion of the tooth prosthesis, and a second three-dimensional shape portion dimensioned to substantially match to a three-dimensional shape of a corresponding substantial surface portion of the crown portion of the at least one adjacent tooth. The first and the second three-dimensional shape portions can have a geometrical relationship configured so that when the first three-dimensional shape portion is affixed to the substantial surface portion of the crown portion of the tooth prosthesis and when the second three-dimensional shape portion is affixed to the substantial surface portion of the crown portion of the at least one adjacent tooth, and when the dental prosthesis is clinically inserted into the embedding portion of the jawbone cavity of the patient, the first three-dimensional shape portion provides temporary primary stability to the tooth prosthesis to thereby maintain the tooth prosthesis in a final geometrical relation to the embedding portion of the jawbone cavity. Further, according to an exemplary configuration, the splint is shaped to not interfere with the occlusal contact between the crown portion of the at least opponent tooth with the crown portion of the at least one adjacent tooth and the crown portion of the tooth prosthesis.

Further, according to the exemplary configuration, the step of manufacturing the custom-shaped dental splint includes deriving from the splint design, numerical control data having at least three portions describing different portions of the splint. The first portion of the numerical control data can include a description of an outer surface portion of the crown portion of the tooth prosthesis corresponding to an outer surface portion of the crown portion of the non-functional natural tooth of the pre-identified patient. The second portion of the numerical control data can include a description of an outer surface portion of the crown portion of the at least one adjacent functional tooth of the pre-identified patient. The third portion of the numerical control data can include the description of the final geometrical relation between at least a portion of the crown portion of the tooth prosthesis and at least a portion of the at least one adjacent functional tooth of the pre-identified patient.

According to another embodiment of the method, the method includes the steps of receiving imaging data describing a three-dimensional shape of an outer surface portion of a root portion of a nonfunctional natural tooth of a pre-identified patient, a three-dimensional shape of an outer surface portion of a crown portion of the nonfunctional natural tooth of the pre-identified patient, and a three-dimensional shape and position of an outer surface portion of a crown portion of at least one adjacent tooth immediately adjacent the jawbone cavity of the pre-identified patient and geometrical relation thereto. The method can also include deriving digital data defining a three-dimensional shape of an outer surface of the root portion of a tooth prosthesis responsive to the received imaging data, and manufacturing the tooth prosthesis at least partially responsive to the digital data to form at least a substantial portion of the root portion of the tooth prosthesis, whereby the three-dimensional shape of the outer surface of the root portion of the tooth prosthesis dimensionally matches a corresponding three-dimensional shape of a corresponding outer surface portion of the natural tooth of the pre-identified patient. The method can further include deriving digital design data defining a custom-shaped splint design, the splint design having an elongate tooth-surface contoured body including a tooth-facing outer surface, a non-tooth-facing outer surface opposite the tooth-facing outer surface, and an outer perimeter surface extending therebetween, and manufacturing the custom-shaped splint at least partially responsive to the derived digital design data defining the custom-shaped splint to form at least a substantial portion of the splint. The tooth-facing outer surface can include a first three-dimensional shape portion dimensioned to substantially match to a three-dimensional shape of a corresponding substantial surface portion of the crown portion of the tooth prosthesis and a second three-dimensional shape portion dimensioned to substantially match to a three-dimensional shape of a corresponding substantial surface portion of the crown portion of the at least one adjacent tooth, with the first and the second three-dimensional shape portions having a geometrical relationship so that when the first three-dimensional shape portion is affixed to the substantial surface portion of the crown portion of the tooth prosthesis and when the second three-dimensional shape portion is affixed to the substantial surface portion of the crown portion of the at least one adjacent tooth, and the tooth prosthesis is clinically inserted into an embedding portion of the jawbone cavity of the pre-identified patient, the first three-dimensional shape portion provides temporary primary stability to the tooth prosthesis and, due to the positioning and orientation of the at least one adjacent tooth, the splint maintains the tooth prosthesis in a final geometrical relation to the embedding portion of the jawbone cavity.

According to an other embodiment of the present invention, a method of manufacturing a dental prosthesis for implantation into a jaw bone cavity of a pre-identified patient can include the steps of receiving imaging data describing a three-dimensional shape of an outer surface portion of a root portion of a nonfunctional natural tooth of a pre-identified patient, deriving digital design data defining a three-dimensional shape of an outer surface of the root portion of a tooth prosthesis matching a corresponding three-dimensional shape of a corresponding outer surface portion of the natural tooth of the pre-identified patient responsive to the received imaging data, manufacturing the root portion of the tooth prosthesis at least partially responsive to the digital data to form the at least a substantial portion of the root portion of the tooth prosthesis, and manufacturing tissue engineered means for surface conditioning the outer surface of the root portion of the tooth prosthesis by employing tissue engineering processes to be applied to one or more of the following: the surface of the root portion of the tooth prosthesis and the jaw bone cavity of the pre-identified patient.

According to yet another embodiment of the present invention, a method of manufacturing a dental prosthesis for implantation into a jaw bone cavity of a pre-identified patient can include the steps of receiving autologous tissue samples of the pre-identified patient, developing tissue engineered means for surface conditioning an outer surface of the root portion of the tooth prosthesis from the autologous tissue samples of the pre-identified patient, and providing the tissue engineered means for surface conditioning an outer surface of the root portion of the tooth prosthesis to be clinically applied thereto.

Such embodiments of the various methods can be also favorably combined with laboratory methods according to various embodiments of the present invention. One of such laboratory methods can include the coating of the root portion of the prosthesis with engineered tissue that is grown in the laboratory from autologous tissue, bone or root material samples of the patient of interest. Alternatively, to the aforementioned use of autologous material, human allogenic bone, root or tissue material, can be used. Alternatively, to the use of human bio-material, tooth, bone or tissue material of animals, for example, bovine or synthetic materials, can be used for the process step of tissue engineering. Tissue engineering includes the use of a combination of cells, engineering materials, and suitable biochemical factors to improve or replace biological functions. In the context of certain embodiments of the present invention disclosed herein, this would include the growth of soft tissue or bone structures in a controlled laboratory environment.

The term regenerative medicine is often used synonymously with tissue engineering, although those involved in regenerative medicine place more emphasis on the use of stem cells to produce tissues. This is an additional approach that can be favorably combined with other specific embodiments of the present invention, disclosed herein.

The various embodiments of this invention are not only substitutive but additive to the available options in the field of restorative and prosthetic dentistry with the result that in most cases the need to use removable dentures will be significantly postponed. In this context, various embodiments of the present invention described herein relate to fabricating customized segments of the dentition, single teeth, roots and crowns or parts of those. The artificial reproduction of the original root will be inserted into the alveolus, the natural cavity of the root of the tooth to be replaced. It will either be adopted by the periodontal ligament of the patient or osseointegrated, if the periodontal ligament is no longer functional. The shape of the root will be a substantial copy of the root to be replaced or may be intentionally smaller, for example, to compensate for measurement or manufacturing tolerances or inaccuracies. The shape of such roots may be a copy of the root to be replaced, or it may be directly adapted to the alveolar situation, or any combination thereof.

In certain cases it is advantageous according to an embodiment of the present invention to modify the shape to be integrated. For example, it may be appropriate to conjoin the two or three roots of a molar to gain additional stability or enable the manufacturing of such. Also, strongly bent root tips may be reduced or left away in order to ease the insertion of the prosthesis. In cases of root resorption, it may be appropriate to re-establish a shape close to the estimated shape of the original shape of the root before the resorption clinically occurred. Accordingly, advantageously, imaging data of an earlier clinical situation or imaging data of mirrored or unmirrored data of the same or a similar shaped root of the same or the other (right-to-left, left-to-right) side of the jaw or of an opponent jaw of the patient may be favorably used in this context according to one or more embodiments of the present invention. It may be additionally possible to consider and use generic (averaged) root shapes in the process designing the target shape of the prosthesis. The extraction socket may be enlarged to accommodate for a bigger or different root shape compared to the extracted root shape.

Various embodiments of the present invention avoid or postpone the need of conventional heavily invasive implants for a significant time by using at first the natural periodontal structure as long as possible and afterwards by customized osseointegrated artificial roots or teeth. No such approach in dentistry based on design and manufacture of customized teeth including the root, or only roots suitable to be used in conjunction with off-the-shelf or customized components (typically for the visible part like veneers or complete crowns) used in the field of implantology for an individual patient, and design and manufacture of such customized tooth, has been proposed to date. The implants widely used in dental treatment today are off-the-shelf products. Because teeth have to fit properly for comfort and healing-process after surgery in the periodontal ligament of a patient, some commonly used implants do not constitute an optimal replacement.

According to various embodiments of the present invention disclosed herein, the artificial root will be osseointegrated—embedded into the natural extraction cavity. Other embodiments of the present invention advantageously maintain and preserve the principle of the natural mechanism of holding the teeth in the jaw structure of a dental patient in cases where a tooth needs to be replaced. According to such embodiments of the present invention, the customized dental prostheses are integrated into, healed in, and at least partially adopted by the fibrous connective tissue interface of the anatomical structure of an individual patient that is naturally holding the tooth.

Directly after placement, the prosthesis may be tied, glued or otherwise fixated for several weeks to adjacent original or artificial teeth or tentative implants like mini-screws likewise with the custom splint according to an embodiment of the present invention.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 6 shows an artificial tooth having a root portion and a crown portion, the portions representing the root being coated in order to promote periodontal integration according to an embodiment of the present invention.

FIG. 7 is a view of an artificial tooth being made from a material promoting periodontal integration, the crown being coated with another material having optimized esthetic and/or mechanical properties according to an embodiment of the present invention.

FIG. 8 shows an artificial tooth, the portion representing the crown being made from a material having optimized esthetic and/or mechanical properties, while the portion representing the root is made from a material promoting periodontal integration according to an embodiment of the present invention.

FIG. 9 is a view of an artificial tooth being made from a material having optimized esthetic and/or mechanical properties, the portions representing the root being coated in order to promote periodontal integration according to an embodiment of the present invention.

FIG. 13 is a cross-sectional view of a segmented artificial tooth, the segment representing the root being expanded using a screw and a dowel in order to support osseointegration and improve physical stability after implantation according to an embodiment of the present invention.

FIG. 14 shows an extraction socket.

DETAILED DESCRIPTION

The present invention will now be described more fully hereinafter with reference to the accompanying drawings, which illustrate embodiments of the present invention. This invention may, however, be embodied in many different forms and should not be construed as limited to the illustrated embodiments set forth herein. Rather, these embodiments are provided so that this disclosure will be thorough and complete, and will fully convey the scope of the present invention to those skilled in the art. Like numbers refer to like elements throughout. The prime notation, if used, indicates similar elements in alternative embodiments.

Figure 1:
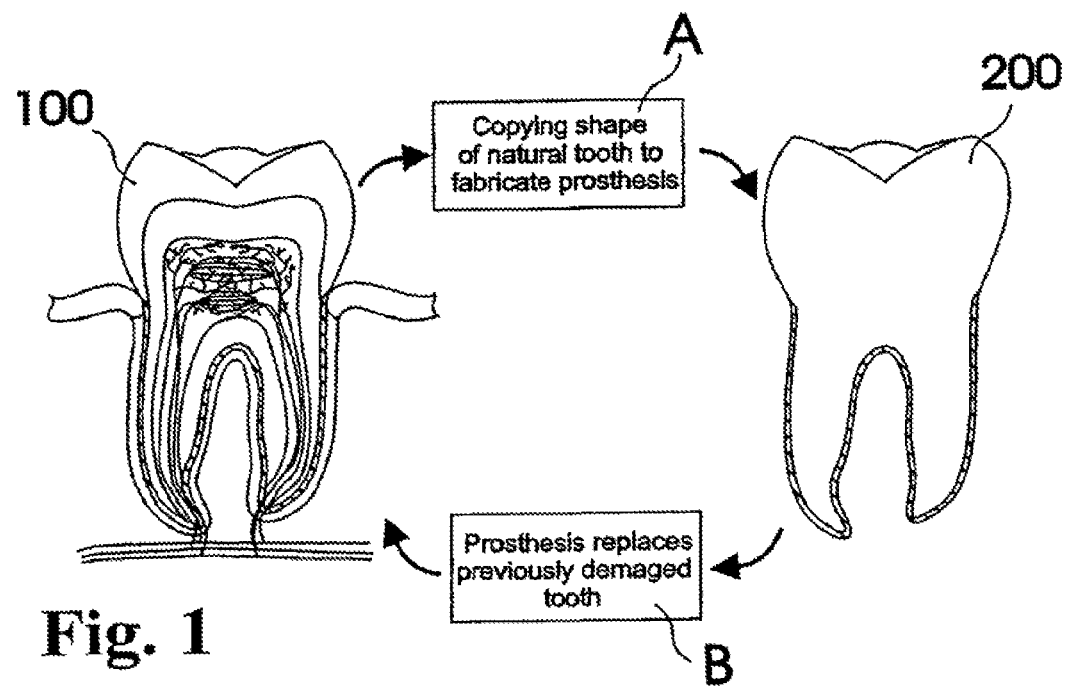
FIG. 1 shows a procedure of replacing a human tooth with a dental prosthesis in accordance with an embodiment of the present invention.
Figure 28:
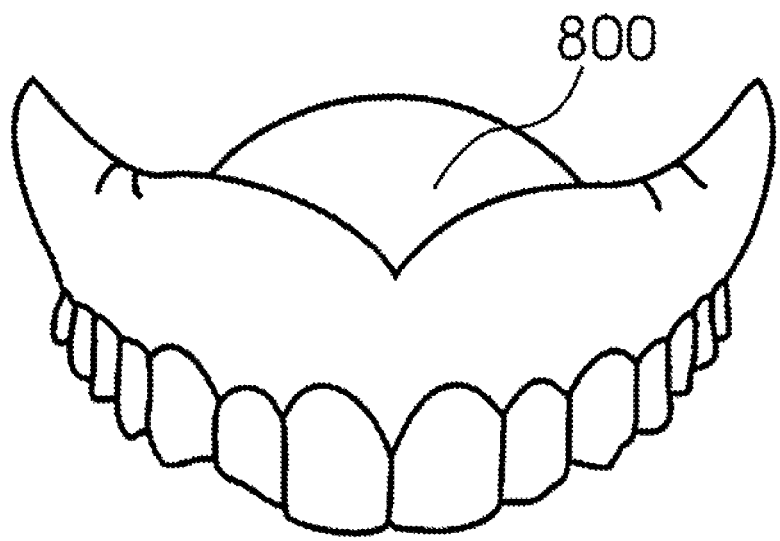
FIG. 28 shows a removable denture according to prior art.

Current methods for replacing damaged teeth have several disadvantages. For example, conventional bridge implants require healthy teeth to be ground and osseointegrated implants are drastically invasive. Additionally, these prostheses have a limited average lifetime. Removable dentures (800) as shown, for example, in FIG. 28 are certainly the final prosthetic option. An object of an embodiment of the present invention is to design and manufacture customized dental prosthesis for replacing human teeth. FIG. 1 illustrates a method of replacing a human tooth with a customized dental prosthesis according to an embodiment of the present invention. First, in step (A), a copy (200) of the natural tooth (100) to be replaced is fabricated. Then, in step (B), the natural tooth (100) is replaced with the prosthesis (200).

Figure 2:
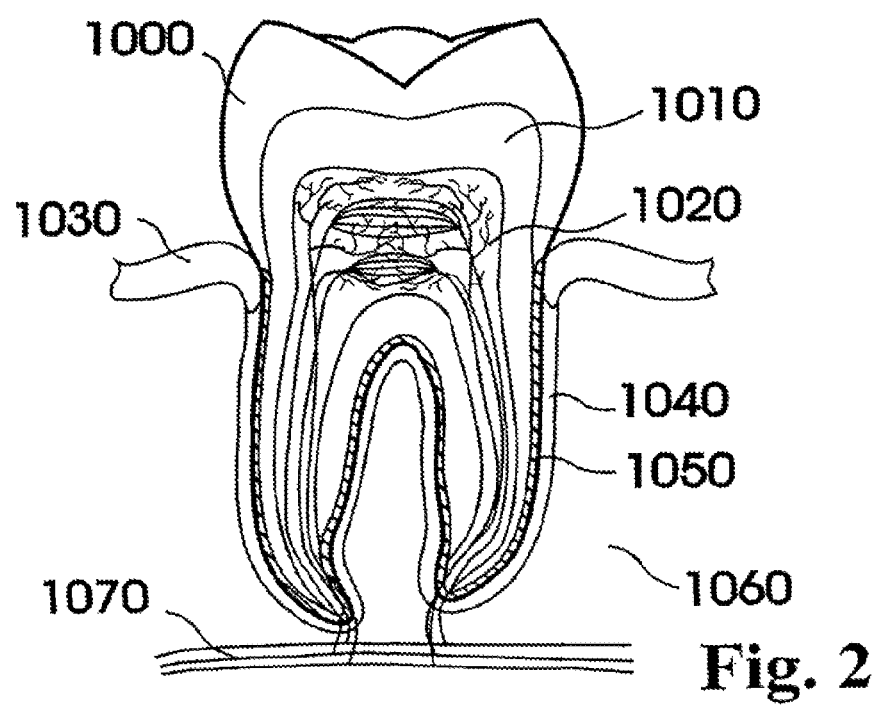
FIG. 2 is a detailed cross-sectional view of a natural tooth.

FIG. 2 shows a natural tooth embedded in its socket. The pulp (1020) holds nerves and blood vessels (1070). It is surrounded by dentine (1010), which is covered with enamel (1000). The root portions have a thin layer of cement (1050) providing connection to the ligament (1040), which serves to anchor the tooth to the bone (1060). The outside of the bone is covered with gum (1030).

Figure 26:
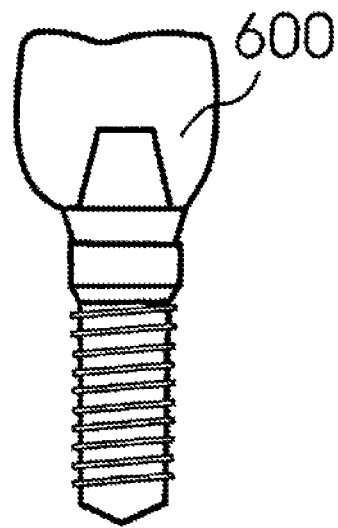
FIG. 26 shows a dental implant according to prior art.
Figure 27:
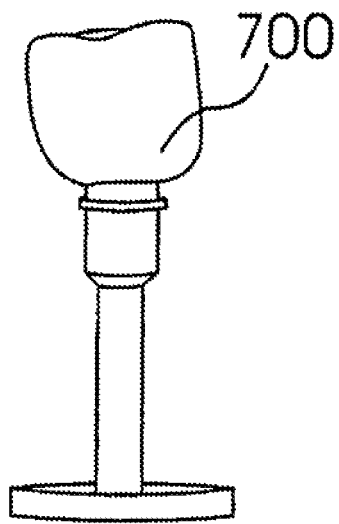
FIG. 27 shows another implant according to prior art.

FIGS. 26 and 27 show conventional implants. The implanted portion (610 and 710) is an off-the-shelf part to be inserted into a hole drilled into the jaw bone. The crown (600 and 700) is generally customized to the individual tooth it is replacing.

According to an embodiment of invention, a dental prosthesis is individually shaped and integrated into the natural extraction socket of an individual patient. The shape of the portions of the prosthesis representing the root substantially copies the natural root of the tooth that was located in the socket. The shape, however, may be modified in order to better adapt to the natural socket or to ease insertion of the prosthesis. Also, the socket may be surgically adapted for the same reasons. For example, damaged and infected soft tissue, tooth or bone substances would not allow for immediate implantation. Then, a dental laser may be used to remove the damaged structures. The most commonly used dental lasers are diode, carbon dioxide, erbium YAG, erbium YSGG, Nd:YAG, and argon lasers. The applications for each wavelength depend on the absorptions of laser energy by different tissue types. The erbium family can be used for caries removal, bone surgery, mucosal surgery and gum surgery. While other laser families are mainly used in soft tissues surgeries. Benefits in laser assisted dental treatment include decreased morbidity after surgery, hemostasis, and a reduction in the need for anaesthetics in selected cases.

An Erbium laser, for example, emits light with a wavelength of 2940 nanometers, which is primarily absorbed by water. Decayed material has an extremely high water content so that the laser light energy evaporates the damage and is able to cut very precisely with little or no collateral damage depending on the settings used during the surgery. When used on hard tissues the Erbium laser energy that touches the hard tissue heats up the water within the hard tissue and causes that water to be turned into steam. That causes a mini-explosion to occur and the hard tissue is "ablated" (removed). Diode lasers in general use as an active medium, a semi-conductor P-N junction made in a GaAlAs crystal. A flexible fiber is used to transmit the laser energy to the surgical site.

According to an embodiment of the present invention, a segmented prosthesis can be used. A segmented prosthesis, also referred to as a segment, is one in which a first segment is implanted into the extraction socket and second segment, for example, a portion representing the crown of a tooth is attached to the segmented portion. Accordingly, a segment prosthesis includes at least two separate portions which may be manufactured and implanted at separate times. The segment which is implanted into the extraction socket is a representation of the root of the natural tooth and can be manufactured based on 3D imaging data. The segment representing the crown can be manufactured according to standard procedures known in the art.

An embodiment of the present invention comprises the following steps: (i) recording and digitizing (scanning) the three-dimensional anatomical shape of a human tooth or dentition; (ii) obtaining a virtual model of the tooth as data record; and (iii) manufacturing of the prosthesis based on the three-dimensional data obtained, for example, by the scan and, if applicable, optimized.

The data may either be recorded intra-orally from the patient, such as with a 3D camera, a micro laser optical device, a computerized tomography apparatus, or an ultrasound apparatus, or be recorded extra-orally by scanning an extracted tooth, for example. If required, the model can be modified in order to ease insertion or to receive aids for the final correct positioning of the fabricated prosthesis. The prosthesis can be directly produced by milling, grinding or rapid prototyping, for example, at a dentist's office or in a laboratory. It can also be produced using conventional laboratory procedures such as, for example, casting. The implant portion representing the root can be manufactured using CAM methods, based on an acquired virtual model, while other portions of the prosthesis, for example, representing the crown, or bridge, are manufactured using standard procedures known in the art.

The process of milling or grinding dental crowns and inlays from ceramic material based on digital data was successfully introduced to dentistry approximately twenty years ago by SIEMENS (now Sirona, Bensheim, Germany) under the brand name CEREC. A modification of the SEREC system can provide a suitable similar CAD/CAM and CNC design and manufacture capability. Although conventional prosthesis manufacturing systems, such as the CEREC system, are generally closed systems, one skilled in the art would readily appreciate these closed systems can be modified such that they may be integrated into the methods of the present invention. Furthermore, certain embodiments of the present invention disclosed herein relate to standard off-the-shelf CAD/CAM and CNC components that can be readily integrated into the disclosed methods Preferably, at least the customized implant portion of the dental prosthesis is fabricated using a CAD/CAM based method and system, wherein the three-dimensional shape of an extracted tooth is scanned and substantially copied, using a 3D scanner, multi-axes CNC machinery, and biocompatible material or material later to be covered with a thin layer of biocompatible material that is suitable to be integrated into and adopted by the existing periodontal ligament cell structure of an individual patient.

Figure 5:
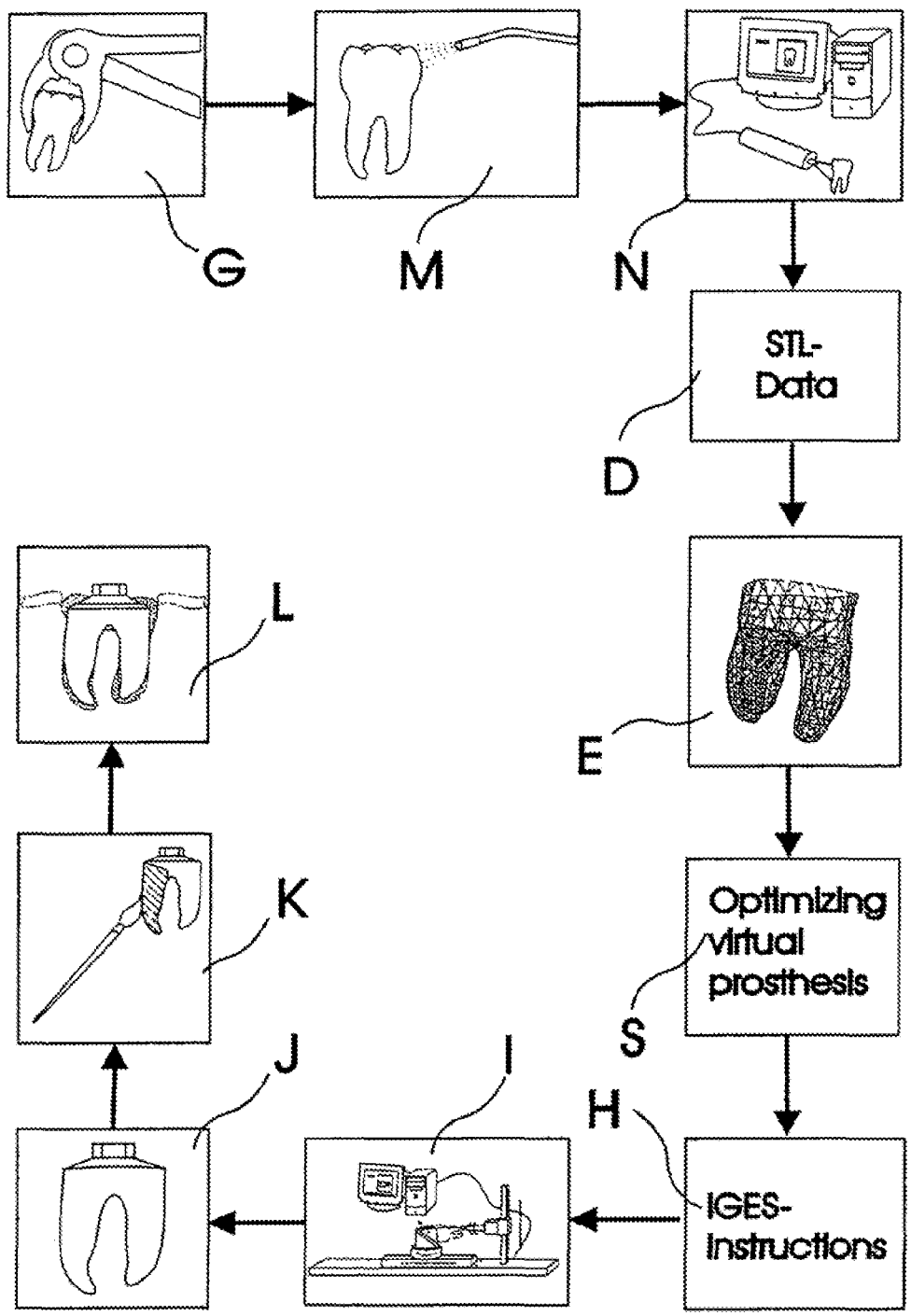
FIG. 5 shows the process steps of acquiring three-dimensional data of the root of an extracted human tooth, processing and completing the resulting 3D data with features for connecting an off-the-shelf abutment and inserting the prosthesis into the socket of the natural tooth according to an embodiment of the present invention.

An overview of a method for replacing a tooth according to an embodiment of the present invention is shown in FIG. 5. First, the tooth to be replaced is extracted (step G) and properly cleaned (step M). Then, 3D imaging (step N) is performed in order to obtain 3D data (D) representing the three-dimensional shape of the root of the tooth. The resulting 3D data is imported into CAD software and displayed to an operator (step E). At this point, the 3D data may be modified, for example, to alter the shape of the root of the virtual model. It should be noted that although FIG. 5 contemplates interaction with an operator, one skilled in the art would readily appreciate that this functionality may be fully automated. Additional features also may be added from a digital library and merged into the 3D root data (step S). The resulting 3D data is converted into IGES format and exported (step H) to a CAM system for fabricating (step I) the prosthesis (J). The fabricated prosthesis is then coated with a substance promoting bone ingrowth (step K). It should be noted that, according to an embodiment of the present invention, coating the prosthesis is an optional step. The prosthesis is then implanted into the extraction socket (step L).

The tooth to be replaced, a lower left incisor (having an envelope volume of approximately 7 min×8 mm×23 mm), for example, is extracted in a surgical environment and then disinfected and cleaned in a solution of hydrogen peroxide. The three-dimensional shape (scan) of the extracted tooth may be obtained using, for example, a light-based scanner such as, for example, the ATOS II SO (gom GmbH, Braunschweig, Germany). In a first step, the root of the tooth is scanned. To achieve an optimal surface for optical scanning, the root is covered with a thin layer of $TiO_2$ powder (e.g., CEREC powder from Sirona, Bensheim, Germany) that is applied with an atomizer using compressed air. Other coatings are also applicable that can, for example, be applied by air-brush painting or a regular brush. For example, it is possible to "shake-up" $TiO_2$ powder in alcohol and apply a uniform thin layer of $TiO_2$ by airbrushing to thereby generate high-precision data during scanning. A portion of the crown of the tooth can be attached to the turntable of the scanner using a removable adhesive material (like, e.g., wax used in dental laboratories).

The turntable is then rotated in 15° increments step by step for a 360° view. The scanner scans at each of the 15° degree increments the optically accessible root surface of the tooth, and can thus, generate and export digital surface data representing the scanned portions of the three-dimensional shape of the surface of the root. The turntable is controlled by the software delivered with the scanner.

Figures 32, 33, 34:
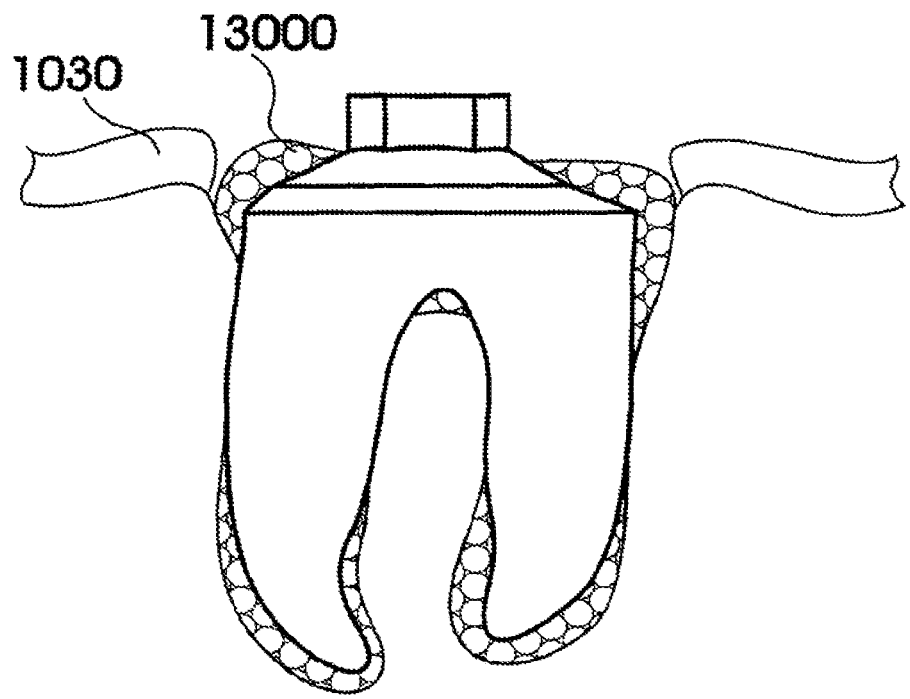
FIG. 32 shows an arbitrary portion of an STL file in ACSII format.
FIG. 33 shows an arbitrary portion of an IGES file in ACSII format.
FIG. 34 shows an implanted artificial tooth, the voids between the root portion and the extraction socket filled with a bone promoting substance according to an embodiment of the present invention.

The digital surface data consists of multiple measurement data points each having an x, y, and z coordinate and together having a density better than 0.1 mm and an accuracy noise of less than 0.05 mm. Alternatively, other resolutions, accuracies, and coordinate systems including, but are not limited to cylindrical or spherical coordinate systems, can be employed by those skilled in the art. The data points are then exported in STL format according to this exemplary embodiment of the present invention. This widely used file format describes a surface or portions of a surface by interconnected triangles. STL files can be encoded either binary or in ASCII format. FIG. 32 shows an arbitrary example of a portion of such a file in the easily readable ASCII format.

Reference elements that are fixed to the turntable can additionally be scanned at each increment. The ATOS II scanner software is able to detect such reference elements in the STL data of each incremental scan. Based on the reference elements it automatically transforms, superimposes, and combines the incremental scans. The result is a comprehensive STL file describing the surface of the root of the tooth.

Other suitable imaging methods include, but are not limited to CT, CBCT, MRT, ultra sound, destructive scanning, active triangulation, passive triangulation, confocal scanning, and Time of Flight (TOF). Such methods generate either surface descriptions, for example, in STL-format, or volumetric data, for example, in a so called "voxel"-format that can be transformed into surface data by generally available software applications known to those skilled in the art, and vice versa.

Figure 29:
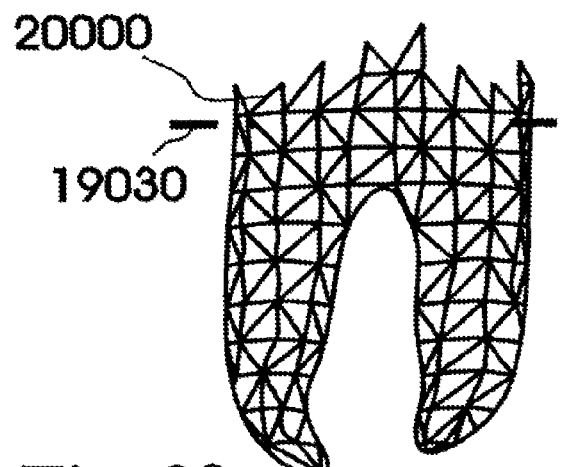
FIG. 29 shows 3D data resulting from the imaging of the root of a natural tooth according to an embodiment of the present invention.
Figure 30:
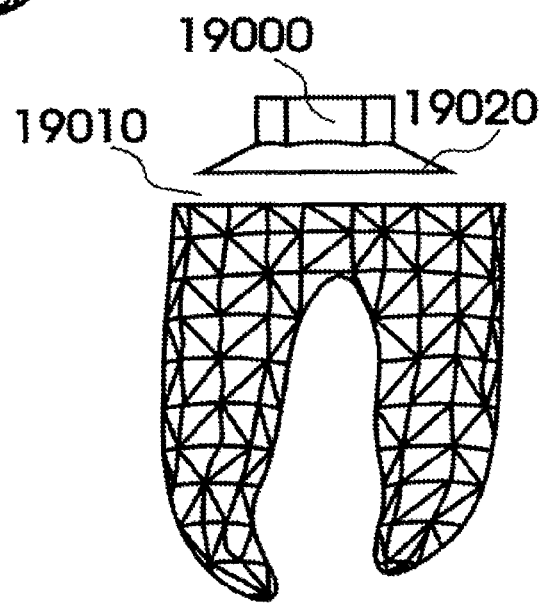
FIG. 30 shows the 3D data of FIG. 29, but cleanly cut at the top, and a virtual hexagon socket from an electronic library according to an embodiment of the present invention.

The scan of the root is then loaded into a CAD software application called MAGICS (Materialise, Leuven, Belgium), for example. Using the cutting features of MAGICS, the occlusal facing edge of the virtual root model (FIG. 29, 20000), which will be uneven and "frayed" in the original scan data, can be straightened in order to receive a clean contour. A straight cut is then performed at a location (19030) where scan data is substantially complete. This is demonstrated in FIGS. 29 and 30. Then, from an electronic library, a virtual hexagon socket is selected, for example, and additionally loaded into MAGICS and placed on top of the virtual root, as shown in FIG. 30. Note, when terms like "top" and "bottom" are used in this context, it is always assumed the root tip points downwards. The hexagon socket consists of the hexagon shape (19000) fitting to the off-the-shelf abutment that can later be mounted to the artificial root, and a junction portion (19020) provides the transition to the virtual root. Since there is a significant variation in root thicknesses and shapes, a selection of hexagon sockets is available in the electronic library, each having a different junction portion in order to receive a minimal gap between the virtual root and the virtual socket.

In a next step, the so-called "stitching" functionality of MAGICS can be used to close the gap (19010) between the virtual root and the virtual socket and, if applicable, also other gaps that may be a result of incomplete scanning. The outcome of this step is a virtual representation of a solid. In this context, a three-dimensional solid is an unambiguous numerical description of the surface of the geometrical shape of a three-dimensional object, with the numerical description showing no holes and clearly identifying the inside and the outside of the surface.

Figure 31:
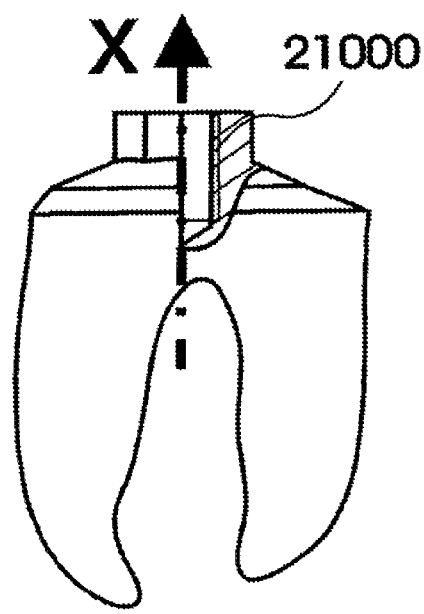
FIG. 31 shows a partial cross-section of an implant having a hexagon socket and a thread for attaching the abutment according to an embodiment of the present invention.

The hexagon socket of the actual prosthesis may also have an inside thread (FIG. 31, 21000) to receive the screw used for mounting the crown. In the embodiment of the present invention, this thread is not part of the virtual model. Rather, the first step of manufacturing is to cut this thread into the workpiece used for fabricating the prosthesis, and then to use it to mount the workpiece to the machine table of the milling machine. To ensure spatial integrity, the coordinate system of the virtual solid generally must be placed properly. Preferably, the origin of the coordinate system will be placed in the center of the hexagon, with one of the main axes running parallel to the midline of the thread as shown in FIG. 31.

The STL data describing the solid representing the tooth are then converted to an IGES data format. This is performed using, for example, software named SolidWorks (SolidWorks Corp., Concord, Mass. USA). The IGES file allows generating a CNC sequence to machine an artificial tooth from a piece of biocompatible material like titanium or a titanium alloy (like Ti6Al4V), that consists, for example, of more than 60% of titanium. FIG. 33 shows an arbitrary example of a portion of such a file. Ceramic material and other biocompatible materials (including but not limited to stainless steel (like 1.4435, 1.4542 or 1.4548), synthetics, elastics, plastics, resin-modified glass-ionomer cement, hybrid-ionomer cement, resin-enforced cement, and other synthetic and plastic materials) are also applicable. For manufacturing the prosthesis for the above mentioned lower left incisor, a workpiece having a size of 20 mm×10 mm×10 mm is generally adequate. For machining, a traditional 5-axis CNC milling device with a high-speed spindle can be used. Other workpiece sizes and multi-axes CNC machining devices can, however, be employed in this context by those skilled in the art.

After cutting the thread that will be located in the center of the hexagon of the finished prosthesis, the workpiece is screwed to an adapter on the machine table of the milling machine by using said thread. The adapter is either shaped so that it leaves sufficient clearance for the milling spindle and the cutter, or a disposable adapter is used so that portions of the adapter itself may be milled off. After teaching the machine the position and inclination of the workpiece, entering the machine and process parameters, and overlapping the physical workpiece with the virtual shape, the root shape of the left lower incisor can be machined by grinding the workpiece down layer-by-layer to the desired shape.

After manually cleaning, removing the excess, if applicable, polishing, degreasing, etching rinsing, disinfecting and drying the workpiece, it is ready for insertion. In order to improve the integration of the implant into the bone, further treatments known to those skilled in the art are possible. Sand-blasting with ceramic particles, for example, creates a rough and thus significantly enlarged surface. Other porous-surfacing technologies can be used in this context too. Coating the surface with hydroxylapatite stimulates bone formation, promoting a physico-chemical bond. Other coatings suitable to facilitate include, but are not limited to, pharmaceuticals, ancestral cells, and proteins. Instead of coating, the aforementioned substances can be applied by others means including, but not limited to, adjunction and injection.

Before inserting the prosthesis, the extraction socket will be properly scraped out or curetted and cleaned. In another embodiment of the present invention, the socket will then be filled with Bioplant (Ken Corporation, Orange, Calif.). Bioplant is a bone promoting substance. It is hydrated with marrow blood from the extraction socket and then injected into the socket using a special syringe delivered with Bioplant. Bioplant fills any voids present between the socket and the implant. After insertion of the implant, additional Bioplant may be applied in order to fully embed the implant below the hexagon socket. FIG. 34 shows the prosthesis embedded in the extraction socket, with the voids being filled with Bioplant (13000). Alternatively, or in addition, bone de-mineralized matrix proteins, bone growth stimulating proteins, or other growth stimulating substances may be applied or otherwise used to facilitate the osseointegration and the building of the secondary stability of the prosthesis. The application of growth stimulating substances can be combined with antibiotic substances to avoid or suppress infection or inflammation. Drug releasing surfaces can be loaded with the aforementioned medical substances or any combination thereof releasing such substance(s) over a period of time. Growth stimulating substances can include or be derived from autologous, allogenic, or animal-derived cells or tissue. In order to avoid the growth of the gum into the void between the implant and the extraction socket, membrane techniques known to those skilled in the art can be employed. Also, the top of the implant excluding the hexagon can be covered with Bioplant. A healing cap is placed on top of the implant. The implant can be secured to the adjacent teeth for about six weeks, for example, by means of a light-curing resin strip known to those skilled in the art.

After the implant is healed in, standard procedures known to those skilled in the art can be performed. After an alginate impression has been taken, a customized tray is fabricated, reinforced, and perforated where the implant is located. An impression post is screwed onto the implant, and the customized tray is placed onto the dentition. The void between the perforation in the tray and the impression post is filled with impression putty. After the putty has set, the screw attaching the impression pin to the implant is unscrewed, and the impression is removed from the patient's dentition and sent to a specialized laboratory. Based on the impression and an impression of the opposing jaw, the technician can fabricate a crown. When the crown is delivered, the abutment is screwed to the implant, and the crown is cemented onto the abutment.

Another substance suitable to promote bone regeneration is CERASORB DENTAL (curasan AG, Kleinostheim, Germany). It consists mainly of pure phase beta-tricalcium phosphate (beta-TCP). CERASORB is completely resorbed and replaced by natural bone structure. Collagen fibers and blood vessels invade the interconnecting micro-pores of the CERASORB granules (micro-pores) and the inter-granular cavities (macro-pores). The primary-grain size of 10-63 µm does not provoke phagocytosis by macrophages.

U.S. Patent Application Publication No. 2005/0084513, which is hereby incorporated by reference in its entirety, discloses a coating for an implant surface. The coating promotes characteristics on the implant surface such as reducing protein unfolding, preventing inflammatory and fibrotic cell accumulation, reducing the number of such cell attachment sites and preventing other adverse biological reactions. The coating may be applied on material via physical and/or chemical binding. It may also be used for in vitro purposes.

Another option is to apply nano-crystalline diamond coating. A coating named r-BeSt (Hartstoffbeschichtungs GmbH, Innsbruck, Austria) shows 100% biocompatibility due to the pureness of the diamond coating, an optimal interconnection between substrate and diamond coatings, and good tribological properties due to the smoothness of the layer and an active surface for bio-chemical reactions. Another option is to apply inert coating with pyrolyt-carbon, which includes isotropic and non-isotropic structures.

In yet another embodiment sputter technologies are used to apply, for example, zircon-oxide surface on a custom-made titanium body to prepare adventurous surface features. For example, it is known that zirconium-oxide is tissue friendly. Sputter technologies include ion sputtering, plasma sputtering and other sputtering technologies used under vacuum.

In another embodiment of the present invention, an unsegmented prosthesis can be fabricated as shown in FIG. 9. The steps of the process are outlined, for example, in FIG. 4. The tooth to be replaced is extracted (step G) and properly cleaned (step M). Then 3D imaging (step N) is performed in order to obtain 3D data representing the three-dimensional shape of the complete tooth. The resulting 3D data (D) is imported into CAD software and displayed to the operator (step E). The shape is modified and optimized as needed (step F, see also FIGS. 23 and 24). The resulting 3D data is converted into IGES format and exported (step H) to a CAM system for fabrication of the prosthesis (step I). The finished prosthesis (J) can be coated with a substance promoting bone ingrowth (step K) and is then implanted into the extraction socket (step L). It should be noted that although FIG. 4 contemplates possibly interaction with an operator, one skilled in the art would readily appreciate that this functionality may be fully automated.

The prosthesis according to this exemplary embodiment, is preferably made from a material supporting osseointegration, such as porous calcium phosphate ceramic. This material provides a scaffold for bony ingrowth. In order to fabricate a complete prosthesis, the shape of the crown must also be available. Therefore, after the imaging of the root portion has been completed, as described above, for example, with respect to FIG. 5, the crown, covered with $TiO_2$ powder, is scanned: A portion of the root of the tooth is attached to the turntable of the scanner while the crown is optically exposed in order to be scanned in the same incremental manner. A second comprehensive STL file describing the surface of the crown of the tooth is accordingly generated. The scan of the root as well as the scan of the crown is performed in such a way that a significant overlapping area of the surface of the counterpart is included in each scan.

The scan of the root and of the crown are then loaded into MAGICS and manually maneuvered to a best fit using the overlapping areas of both scans, and merged into one STL data file. In order to increase accuracy, software detecting a best fit for two independent surfaces can also be used. After manually removing outliers of the scanned measurement data, if required, and identifying and correcting deficient triangles and adding missing parts, the resulting STL surface data forms a three-dimensional solid representing the overall shape of the extracted tooth.

The STL data is then converted to an IGES data format. To fabricate the above mentioned lower left incisor, a piece of calcium phosphate ceramic having a size of approximately 25 mm×10 mm×10 mm using a traditional 5-axis CNC milling device with a high-speed spindle (about 60.000 rpm), a spherical diamond cutter having a diameter of the tip of the cutter of 1 mm and water cooling, can be used. The ceramic workpiece is clamped to the machine table of the milling machine. After teaching the machine the position and inclination of the workpiece, dialing in the machine and process parameters, and overlapping the physical workpiece with the virtual shape, a first portion representing the root shape of the lower left incisor is machined by grinding down layer-by-layer the workpiece to the shape of interest. Then a fixture is made for that specific workpiece to clamp the workpiece at the already machined first portion, for example, by grinding a portion of the geometrical negative shape of the first portion into the receiving part of the fixture.

After teaching the machine position and inclination of the reoriented workpiece clamped into that customized fixture, entering machine and process parameters and overlapping the physical second part of the workpiece with the virtual shape of the second portion to be machined, the crown shape of the left lower incisor is machined by grinding the workpiece down layer-by-layer to the desired shape. After properly cleaning, removing the excess, and degreasing, the prosthesis is ready for insertion into the extraction socket. After the implantation, the artificial tooth is fixed substantially to the same position and inclination of the extracted tooth by being bonded with light curing resin strip to the adjacent teeth.

Figure 17:
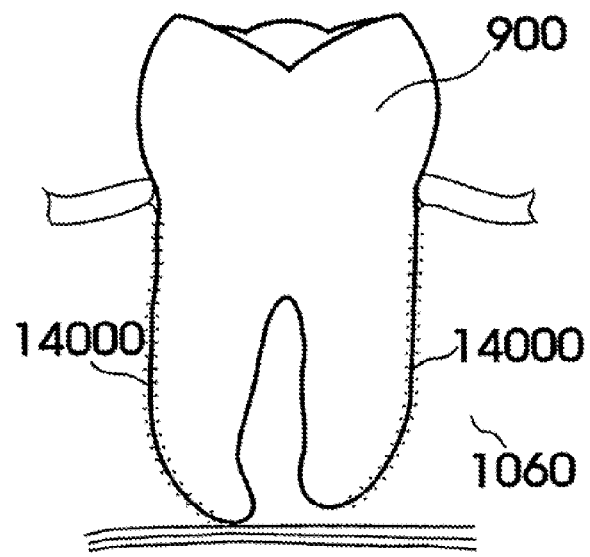
FIG. 17 shows an artificial tooth inserted into the extraction socket and firmly pressed against the walls of the socket in order to promote osseointegration into the bone.

An advantage of this embodiment of the invention is that the complete replacement of the natural tooth can be performed in one appointment. After the prosthesis has healed in, only the resin strip initially securing the prosthesis to the adjacent teeth must be removed. A significant amount of laborious steps can thus be avoided. FIG. 17 shows an osseointegrated unsegmented tooth (900). Osseointegration is achieved in marked areas (14000).

Using computer networks, all process steps may be carried out by different and independent parties. The imaging part can, for example, be performed at the dentist's office, at a hospital or at a location specialized in imaging. The imaging data can then be transferred to a location where the imaging data are further processed in order to ready them for manufacturing. After the design is finished, the data can again be transferred to the dentist for further optimization and/or approval. Consulting a remote specialist in difficult cases using data transfer may also be applicable. Such a remote specialist may be a clinician or an expert in manufacturing or laboratory procedures. Then, the data can be transferred to a remote manufacturing location. All these data transfers can, for example, be performed via the Internet, using preferably Virtual Private Network channels to secure privacy, or through a local area network.

In yet another embodiment shown in FIG. 7, the implant can be made by one type of biocompatible material (9020), for example, titanium or a titanium alloy, and the portion representing the crown can be coated with another biocompatible material (9010), for example, ceramic, to support both optimal physical strength and esthetics. Alternatively, the crown portion is not coated, but is made from a material different from the material used for the root portion. FIG. 8 shows an artificial tooth, the portion representing the crown being made from a material having optimized esthetic and/or mechanical properties, while the portion representing the root is made from a material promoting periodontal integration. Both portions can be attached to each other by a variety of connection methods: they can be bonded, cemented, fixed mechanically (either by a screw or an interlocking surface), or they can be fabricated from a workpiece that is already comprising different materials. Sintering would be one of the suitable processes. Therefore, the prosthesis can be fabricated either segmented, with the parts being connected to each other either before or after implantation or the complete prosthesis is made in a single process. In another embodiment of the present invention, a material promoting cell growth and providing good adhesion for cells is used for the root portions. FullCure 720 may serve as an example of such a material. This is an acrylic based photopolymer and distributed by Object Geometries Ltd., Hebron, Israel. This material can be processed by a rapid prototyping process named "objet Print". Devices for this process are also distributed by Object Geometries Ltd.

In another embodiment of the present invention, the prosthesis is made from stabilized tetragonal zirconium oxide polycrystalline or another aluminum oxide or zirconium oxide material known to those skilled in the art (inCoris ZI, inCoris AL, VITABLOCS, and CEREC Blocs distributed by and Ivoclar Vivadent and SIRONA). Alternatively, the prosthesis can be made of titanium or a titanium alloy and surface coated with zirconium oxide, for example, in sputtering technologies (as offered by Clinical House Europe GmbH).

In case of the osseointegration of a prosthesis according to an embodiment of the present invention disclosed herein, INFUSE® Bone Graft (Medtronic Sofamor Danek) can be applied to stimulate bone formation. INFUSE® Bone Graft consists of two parts—a solution containing rhBMP-2 (recombinant human bone morphogenetic protein 2) and the ACS (absorbable collagen sponge). The protein is a genetically engineered version of a natural protein normally found in small quantities in the body. The stimulation of bone formation can be key to developing osseointegration and to fill voids in between the extraction socket and the actual prosthesis in an accelerated manner. Other growth aiding proteins like bone morphogenetic protein (BMP), dentin matrix protein (DMP), platelet-derived growth factor (PDGF) and/or other bone growth stimulating proteins may be applied or otherwise used additionally or instead in order to facilitate integration, healing, and rebuild of the bone structure of the patient.

In yet another embodiment of the present invention, the prosthesis will not be osseointegrated, but adopted by the ligament of the extraction socket. In this case the prosthesis can be coated, for example, with a material promoting periodontal adoption. According to an exemplary embodiment of the present invention, a thin layer of about 0.05 mm to 0.2 mm of resin-modified glass-ionomer cement (FIG. 9, 9000) can be applied to the surface of the part of the workpiece being inserted into the extraction socket. FIG. 6 shows a segmented artificial tooth, the crown (10000) being made from a material having optimized esthetic and/or mechanical properties, and the root portion (10010) being coated with a substance (9000) promoting periodontal integration, for example, glass ionomer cement. FIG. 9 shows an artificial tooth (9030) made from a material suitable for crowns like ceramics, the root portion being coated with a substance promoting periodontal integration. Other substances promoting periodontal integration include, but are not limited to engineered tissue comprising non-autologous tissue-engineered material and/or autologous tissue-engineered material, cells of a tooth comprising ancestral cells, animal cells, and/or human cells, a matrix protein derivative, a growth protein, a layer of cement, a glass ionomer cement comprising a calcium-alumino-silicate glass powder and an aqueous solution of an acrylic acid homo- or co-polymer, a layer of mineral trioxide aggregate, a light-activated resin-modified glass ionomer cement, a calcium hydroxide cement, and/or a drug release coating or an antibiotic pharmaceutical, or various combinations thereof.

Glass ionomer cement is composed of a calcium-alumino-silicate glass powder and an aqueous solution of an acrylic acid homo- or co-polymer. It is a biocompatible material widely used, for example, for tooth restorations and provides good adhesion to the ligament. Resin-modified glass ionomer cement can be light-cured. The light activates a catalyst in the cement that causes it to cure in seconds. After curing, the artificial tooth is implanted and integrated into the existing periodontal tissue formation of that lower left incisor of the patient and fixed substantially into the same position and inclination of the extracted tooth by being bonded with light curing resin strips to the adjacent teeth.

Another option is coating the portion to be implanted with Ca(OH)2-cement. This is a well known substance in dentistry also used to fill root canals. After setting, EMDOGAIN (Institut Straumann AG, Basel, Switzerland), a substance containing the enamel matrix protein Amelogenin, can be applied. Beneficially, EMDOGAIN is resorbed naturally during the normal healing process, leaving only a residue of enamel matrix protein on the coated surface. This natural and insoluble surface layer encourages the population of cementum-forming cells from the surrounding tissues. Other proteins aiding the growth of dentin, bone or tissue structures like bone morphogenetic protein (BMP), dentin matrix protein (DMP), platelet-derived growth factor (PDGF) and/or other tissue growth stimulating proteins may be applied or otherwise used additionally or instead in order to facilitate integration, healing, and rebuild of the periodontal ligament. The newly created surface also functions as an interface between the tooth and the surrounding tissues, preventing down-growth of the epithelial tissues. Again, instead of coating, all the aforementioned substances can be applied by others means including, but not limited to, adjunction and injection. It may be advisable to prescribe antibiotic pharmaceuticals to reduce the infection risk during the healing process. In another embodiment of the present invention, the root portion(s) of the prosthesis are coated with a drug releasing surface that releases the aforementioned proteins and antibiotic and other inflammation reducing substances or any combination thereof over time. The drug releasing surfaces can be made, for example, of materials that can be completely resorbed and replaced by natural bone structure or soft tissue. Especially in the context of periodontal integration, it might be advisable to utilize an absorbable collagen membrane to separate the faster gum growth from the healing process of the periodontal ligament.

In another embodiment of the present invention, an undersized customized root representation of a ceramic prosthesis is coated with a thin layer of mineral trioxide aggregate (Pro-Root MTA, Dentsply) while potential socket irregularities are prepared with calcium sulphate (Capset, Lifecore Biomedical) in order to promote the selective formation of new periodontal tissue (i.e., cementum, periodontal ligament, Sharpey's fibers and alveolar bone) and to build a barrier against an overgrowth by gingival tissue. The thickness of the coating layer should match the undersizing of the root shape and would preferably be chosen to be about 0.2 to 0.3 mm. It would furthermore be advantageous to insert the prosthesis into the socket as soon as possible, but preferably no more than 24 hours after extraction (see respective reference re: Spouge, Oral Pathology, Mosby, Saint Louis, 1973 above).

Figure 10:
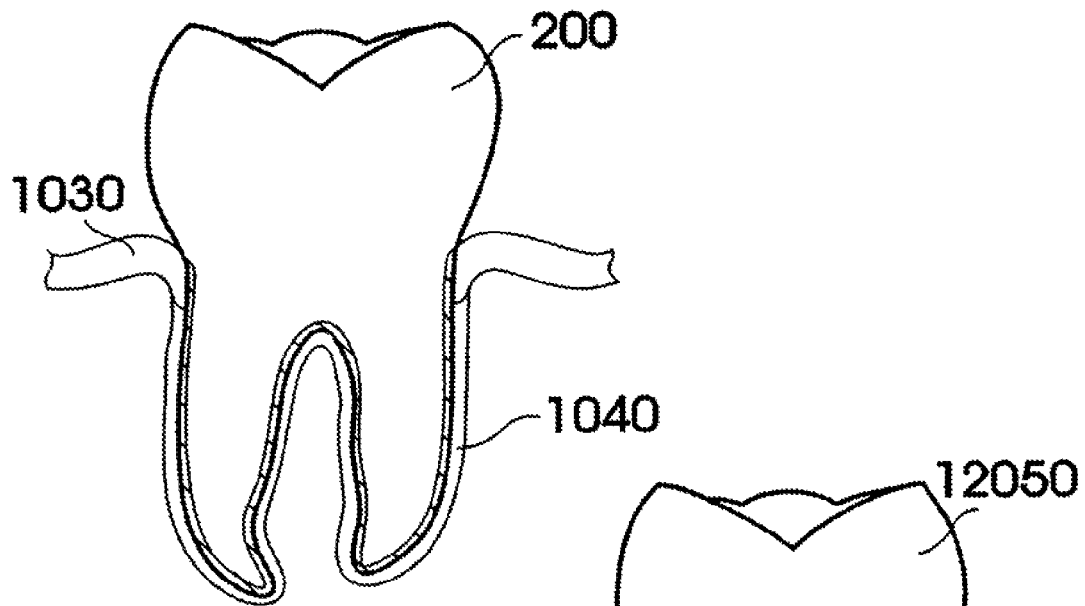
FIG. 10 shows an artificial tooth being embedded in the socket of the natural tooth according to an embodiment of the present invention.

Periodontal integration (see, e.g., FIG. 10) has the advantage that the anchoring of the prosthesis (200) is not stiff as with osseointegrated implants, but shows the elasticity of the natural tooth. The ligaments (1040) are providing support to the teeth in a viscoelastic manner. Furthermore, forces applied to the tooth, and thus to the ligaments, create tension which is actually the stimulus for bone growth. Another function of the periodontal ligaments is to serve as a method for sensation. To support periodontal integration, the implantation of the prostheses should be performed shortly after extraction of the natural tooth, preferably not more than 24 hours after extraction. The key to success is the preservation of cellular vitality in the periodontal ligament and performing the extraction in a surgical environment under conditions of asepsis. Further below, other embodiments of the present invention are disclosed providing instant replacement of the natural tooth.

In another embodiment of the present invention, suitable pre-determined generic root shapes can be selected and employed fabricating the portion of the implant to be osseointegrated or integrated into the periodontal ligament. A variety of generic shapes may be stored on a computer-readable media and accessed by the CAD/CAM system.

Another product that is helpful in adapting an implant into the extraction socket is Atrisorb (CollaGenex Pharmaceuticals, Inc., Newtown, Pa.). Atrisorb helps regrow healthy bone and soft tissues and forms a barrier creating a space in which tissue can grow. Atrisorb is applied as gel and forms a barrier membrane when sprayed with sterile water. It maintains structural integrity for approximately six months. Complete bioabsorption, however, is achieved within nine to twelve months.

In order to assure that only the desired portions of the prosthesis are adopted by the periodontal tissue, other portions, like the surface intended to carry the crown later to be attached to the implant, may be covered with a substance preventing such adoption. Silver is, for example, a biocompatible material suitable for that purpose. The Fraunhofer Institute for Manufacturing Technology and Applied Materials Research (IFAM) has developed a nano-composite plasma coating technology that can be used for applying a thin layer containing silver.

In yet another embodiment of the present invention, the crown of the extracted tooth or the tooth to be extracted is not only subject to 3D imaging, but additional color data are obtained. Depending on the scanning method, color data can already be contained in the scan data, or a separate imaging is performed to record the color of the crown. It is possible to obtain a uniform overall color representing the average color of the crown, or alternatively different shadings for different portions of the crown can be recorded. Based on the color data, the color of the crown can be adapted to the color of the original tooth. The lab technician manufacturing an artificial crown can, for example, be provided with the color data and select the most appropriate color for the prosthesis. If a complete prosthesis is manufactured using CAM methods, a material best fitting the original color can be used, or a coating can be selected that matches the original color.

In another embodiment of the present invention, no fixture is used to manufacture the second portion of the artificial tooth. Instead, dedicated features elements will be added to the shape of the root, such as small holes or posts sticking out, allowing for precise positioning of the artificial tooth for the second step, which includes manufacturing the crown portion. These dedicated features will be removed or closed after the complete tooth has been fabricated.

In yet another embodiment of the present invention, a rapid prototyping process is used for fabricating the dental prosthesis from hybrid materials. The rapid prototyping process may build the prosthesis layer-by-layer. For example, a powdery layer of a substance can be applied on top a workpiece, and then portions of the new layer are hardened by a controlled laser beam, while the other unhardened portions are later be removed. In this manner, different substances having different properties (stiffness, hardness, biological properties etc.) can be applied and therefore different portions of the workpiece be made from different materials. In an embodiment of the present invention, the crown is made from a material different from the one used for the crown. In yet another embodiment of the present invention, the portions representing dentine are made from a material different from the one used for the portions representing enamel.

In another embodiment of the present invention, the three-dimensional data used to fabricate the dental prosthesis is not acquired from an extracted tooth, but obtained intra-orally, the tooth to be replaced still in place. The advantage of this embodiment is that the complete digital preparation and also the manufacturing steps of the artificial replacement can be performed prior to the extraction. That is, according to such embodiment, only when the artificial tooth or segment to be implanted is ready for insertion, is the original tooth extracted. Immediately after extraction, the artificial tooth can be implanted. This contributes to a better healing of the trauma.

Figure 3:
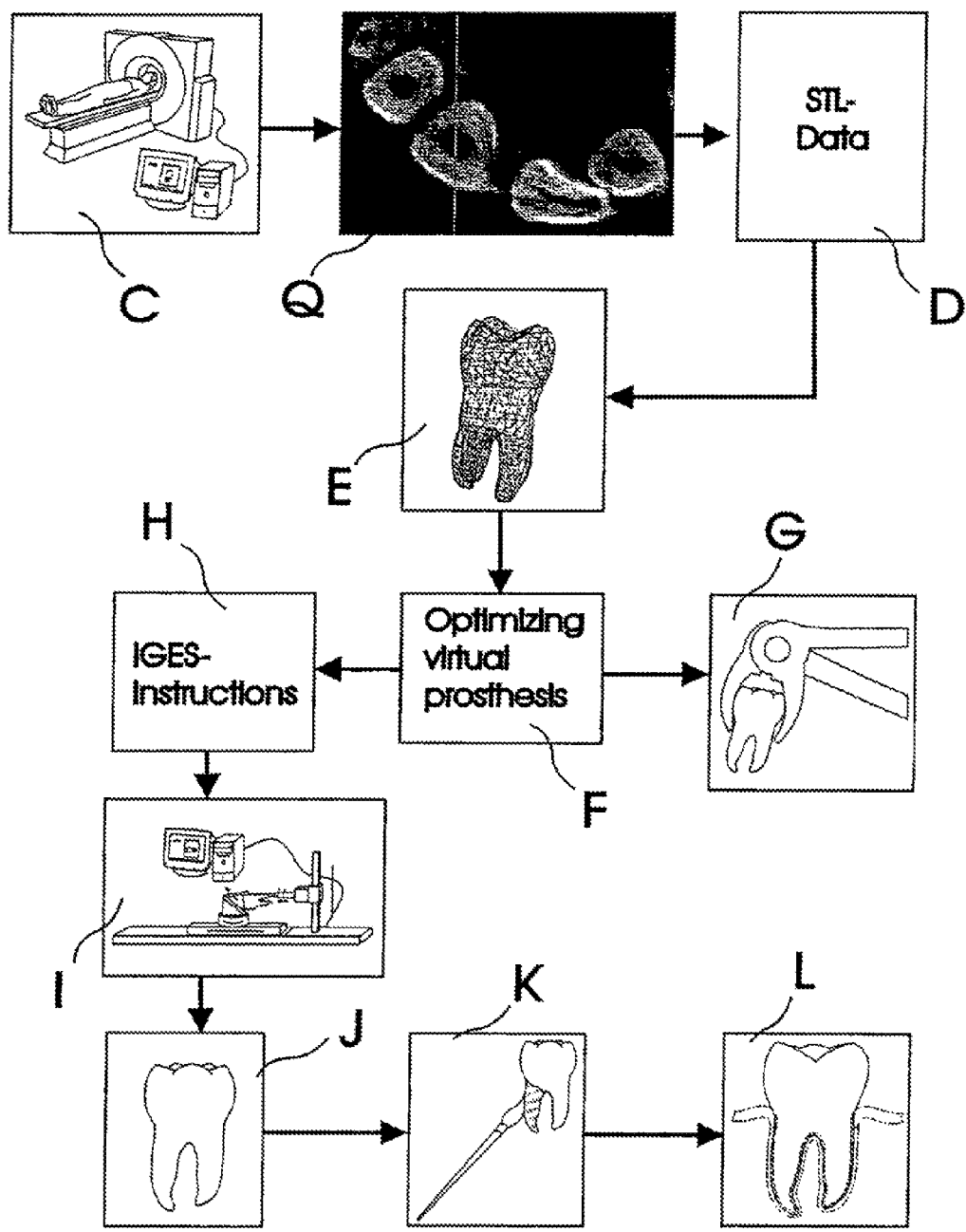
FIG. 3 shows the process steps of intra-orally acquiring three-dimensional data of a human tooth, fabricating an artificial copy, extracting the natural tooth and replacing it with the artificial copy according to an embodiment of the present invention.

FIG. 3 outlines the process steps according to an exemplary embodiment of the present invention. A CT scan (steps C, Q) is made of the dentition of the patient. The resulting 3D data (D) is imported into CAD software and displayed to the operator (step E). The shape is modified and optimized as needed (step F). The resulting 3D data is converted into IGES format and exported (step H) to a CAM system for fabricating the prosthesis (step I). The process may include coating the finished prosthesis (step J) with a substance promoting bone ingrowth (step K). Only after the prosthesis is ready for insertion, is the natural tooth extracted (step G), and the implant is placed into the extraction socket (step L). It should be noted that although FIG. 3 contemplates possibly interaction with an operator, one skilled in the art would readily appreciate that this functionality may be fully automated.

A NewTom 3G-MF12 Cone Beam CT (NewTom Deutschland AG, Marburg, Germany) can be used to acquire the imaging data. The accuracy of the measurement data will be better than 0.2 mm, and therefore, highly sufficient for the process. A spline CT with a small envelope dedicated to dentistry like the Morita can deliver 3D data with even better resolution.

The in-vivo structures represented by CT raw data (for example, in DICOM format) can be analyzed by voxel-based software platforms (IVS Solutions AG; Germany) where 3D objects are separated to be distinguished from "grey scale" data. In another embodiment, adaptable algorithms can be used to analyze the dental structures of interest. Such adaptable algorithms can use known data of generic shapes, for example, to drive the adoption of "grey scale" filters.

Further, methods for intra-oral imaging include, but are not limited to CT, CBCT, MRT, ultra sound, active triangulation, passive triangulation, confocal scanning, and Time of Flight (TOF). The anatomical structures obtained by intra-oral imaging include, but are not limited to, periodontal structure, the alveolus, and the jaw bone of the patient.

Using intra-oral 3D imaging, it is even possible to perform a scan of a patient long in advance of treatment and to file the personal imaging data of the dentition of the patient. In case of an injury or accident where teeth get lost or damaged or are not available for a scan for any other reason, a fabrication of individual prostheses can be initiated immediately, using the previously collected imaging data.

Instead of 3D imaging and digitally processing imaging data, copy milling or copy grinding from the original tooth or parts or the tooth, can be performed. The root can also be shaped according to an impression made directly from the alveolus of the extracted teeth as shown in FIG. 14, using a specialized material or using standard impression materials separated from the surface (periodontal ligament or bone) of the alveolus (500) by a very thin film of plastic or another material suitable for the purpose. Alternatively, an impression can be taken from the extracted tooth. Laboratory methods for fabricating dental prostheses based on impressions, are readily available. These methods are mostly employed using casting processes or light curing or chemical curing processes where monomer components are polymerized to molecular networks. Further, methods of fabricating a substantial copy of the original tooth include, but are not limited to, depositing, sintering, 3D printing, molding, curing, grinding and milling. The ongoing progresses made in rapid prototyping, that is fabricating individual parts directly based on digital data, can strongly contribute to advancing various embodiments of the present invention.

Figure 23:
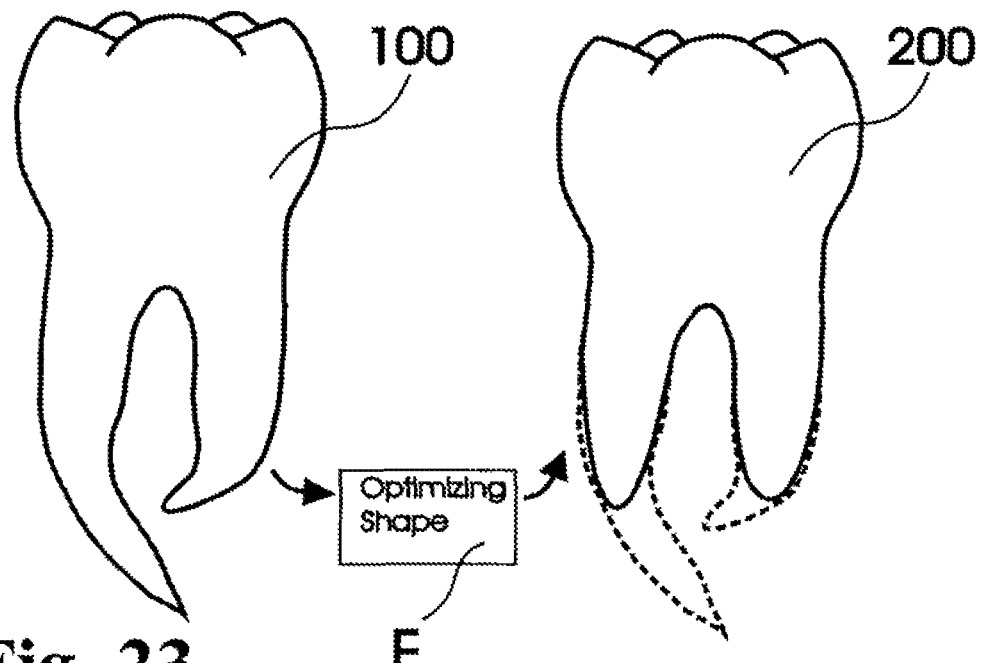
FIG. 23 shows a natural tooth having strongly crooked roots and the artificial substitute according to an embodiment of the present invention, wherein the shape of the substitute has been altered in order to allow for simplified insertion into the natural socket.
Figure 24:
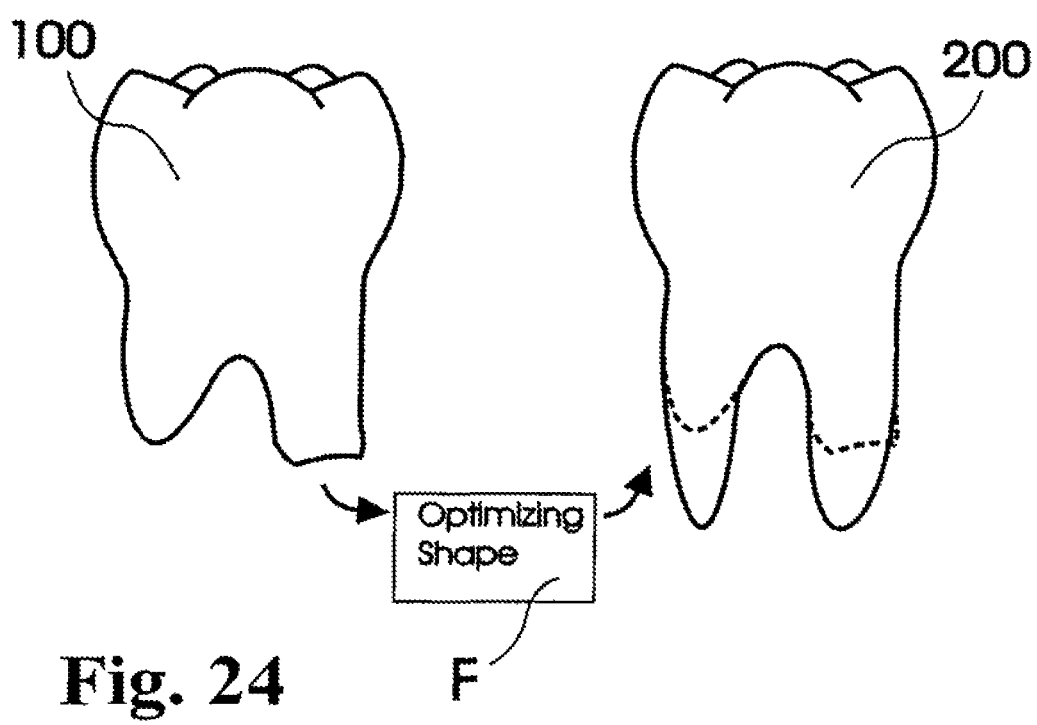
FIG. 24 shows a natural tooth suffering from partial root loss due to root resorption or a surgical procedure and an artificial substitute according to an embodiment of the present invention, the shape of the artificial tooth being optimized for better adaption to the natural socket.
Figure 25:
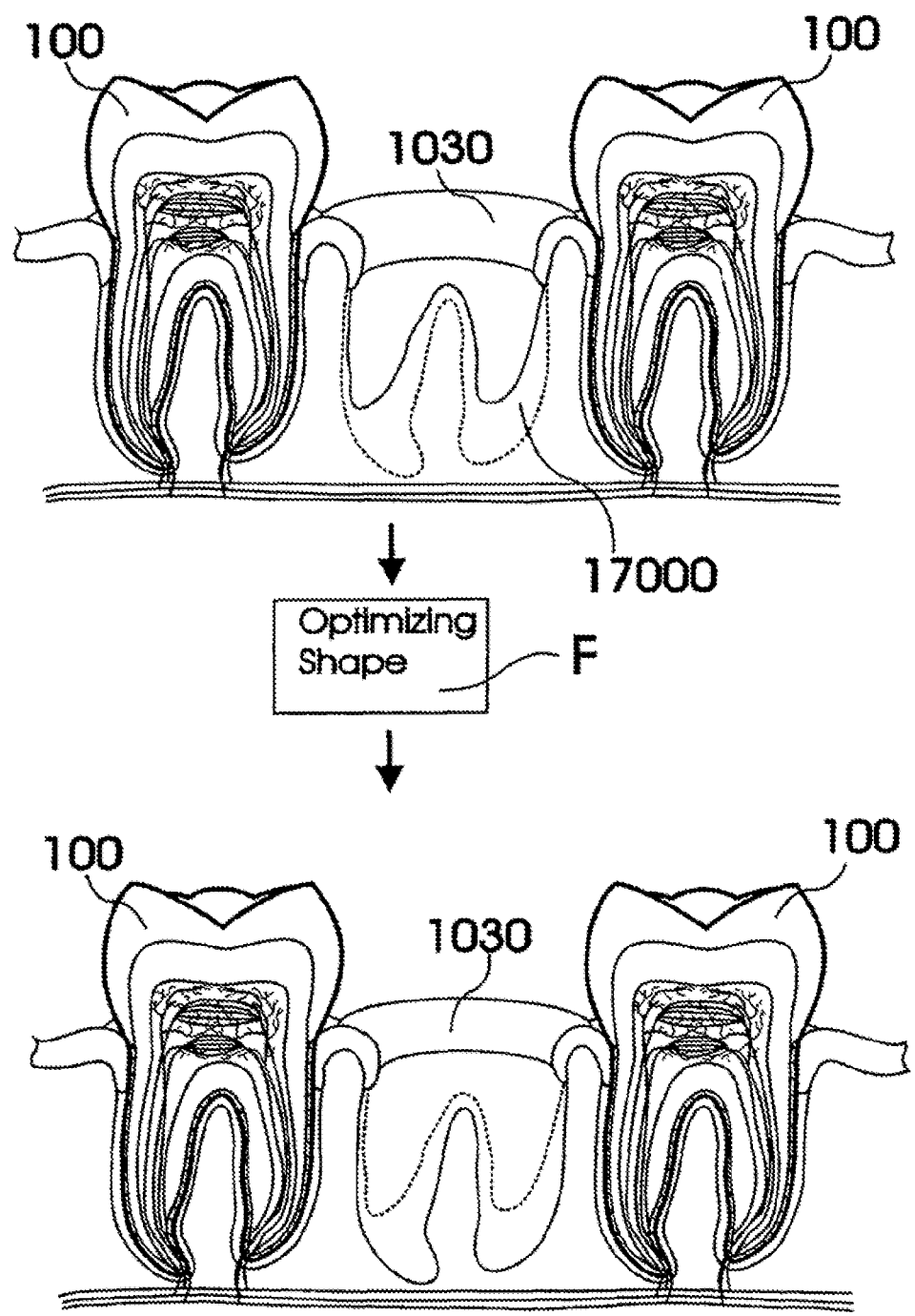
FIG. 25 shows a tooth socket after extraction. Due to root resorption, the size of the socket has been reduced over time. In order to enhance anchoring, the artificial replacement will have a root portion of greater size. Therefore, the socket is surgically enlarged.

In some cases, the shape of the original roots can present difficulties with the insertion of the artificial replacement. In such cases, a proper modification and optimization of the shape of the artificial root according to FIG. 23, is applicable. In other cases, the root of the natural tooth may be suffering from partial root loss due to root resorption or a surgical procedure. In these cases, the root of the replacement can be adapted to the extraction socket as demonstrated in FIG. 24. For example, the customized portion can include a substantial copy of at least 60% of the root shape of the natural tooth while the other portion of the artificial root can be modified as described herein. In other cases, the size of the socket may have been reduced over time due to root resorption as displayed in FIG. 25. The size reduction has occurred in areas (17000). In such cases, it is advantageous to enhance anchoring by surgically enlarging the socket and to adapt the root of the artificial tooth to the enlarged socket. SolidWorks is a suitable CAD software which can be utilized to alter the shape of the implant with respect to the original imaging data.

Figure 22:
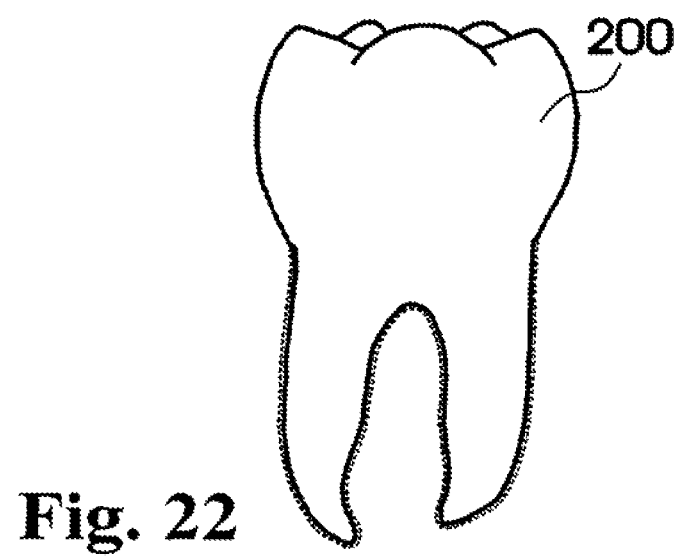
FIG. 22 shows an artificial tooth according to an embodiment of the present invention, the portion representing the root being slightly reduced in size compared to the natural tooth.

There are more reasons to modify the shape of the implant with respect to the original root. To ease insertion into the extraction socket, the shape of the implant may be slightly undersized as shown in FIG. 22. MAGICS provides a functionality allowing for a simple reduction of the overall size of a body. On the contrary, an oversized artificial root may be desirable in order to receive a very tight mechanical fit in the extraction socket to promote osseointegration as displayed in FIG. 17. This can also easily be achieved with MAGICS. This software has a couple of helpful features that have originally been developed to optimize plastic parts for injection molding, but turn out to be useful also for the processes of various embodiments of the present invention.

In yet another embodiment of the present invention, original portions of the natural tooth will be integrated into the implant. Especially portions of the root still being covered with cement will greatly improve adoption into the ligaments of the extraction socket. On order to integrate those natural portions; they will be cleaned and prepared for imaging as described further above. The resulting 3D imaging data can be imported into MAGICS and processed like the data of a complete tooth. The three-dimensional virtual body can then be placed at the proper location with respect to the virtual body representing the shape of the implant to be produced. Using Boolean functions of MAGICS, the body representing the natural portion(s) of the tooth can be subtracted from the body representing the implant, thus creating a cavity in the implant having the exact size and shape of the natural portion(s) of the tooth to be integrated into the implant. After the implant has been fabricated and processed, the natural portions of the tooth are cemented into the implant.

Figure 15:
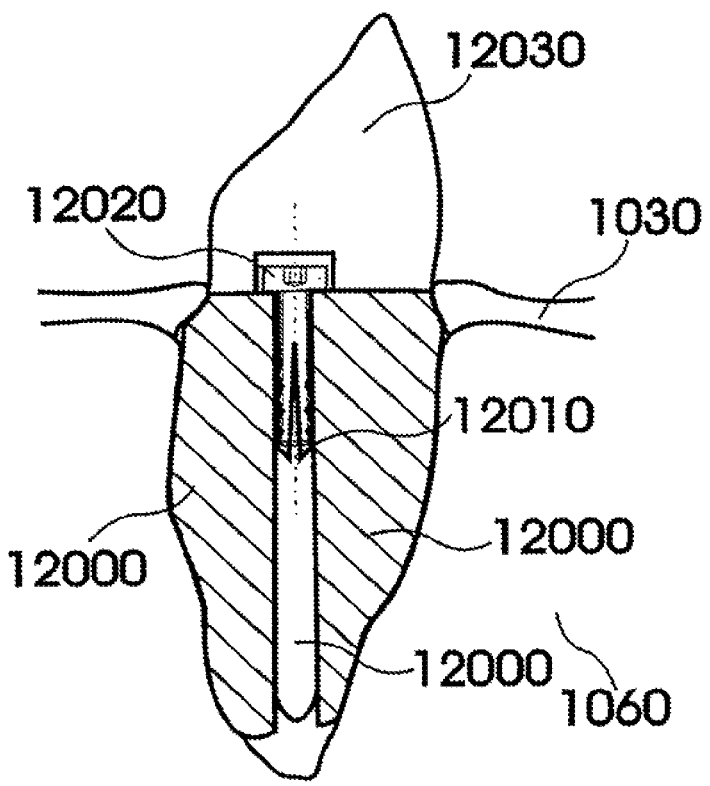
FIG. 15 is the artificial tooth of FIG. 13 inserted into the extraction socket and expanded.
Figure 16:
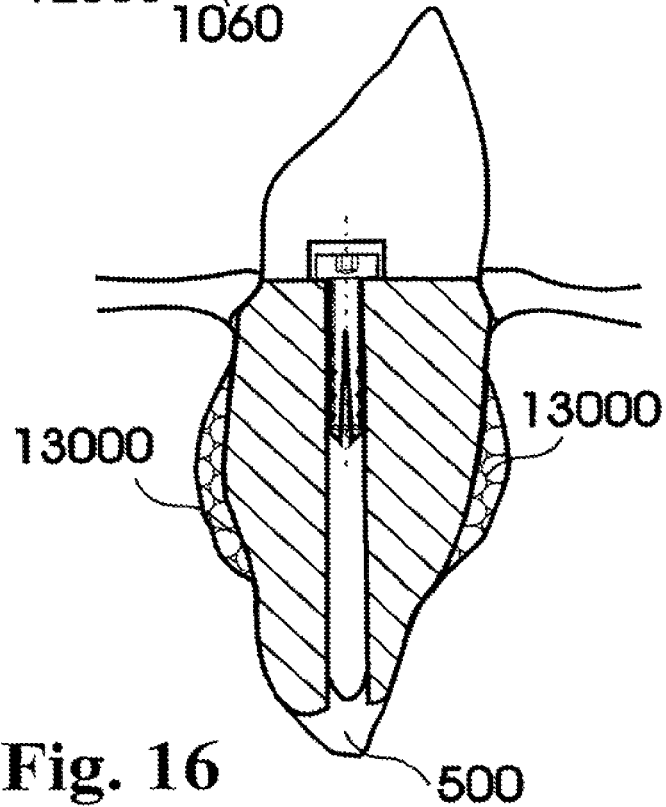
FIG. 16 is a view of an artificial tooth according to FIG. 15, wherein voids between the socket and the tooth are filled with a bone promoting substance according to an embodiment of the present invention.
Figures 35, 36:
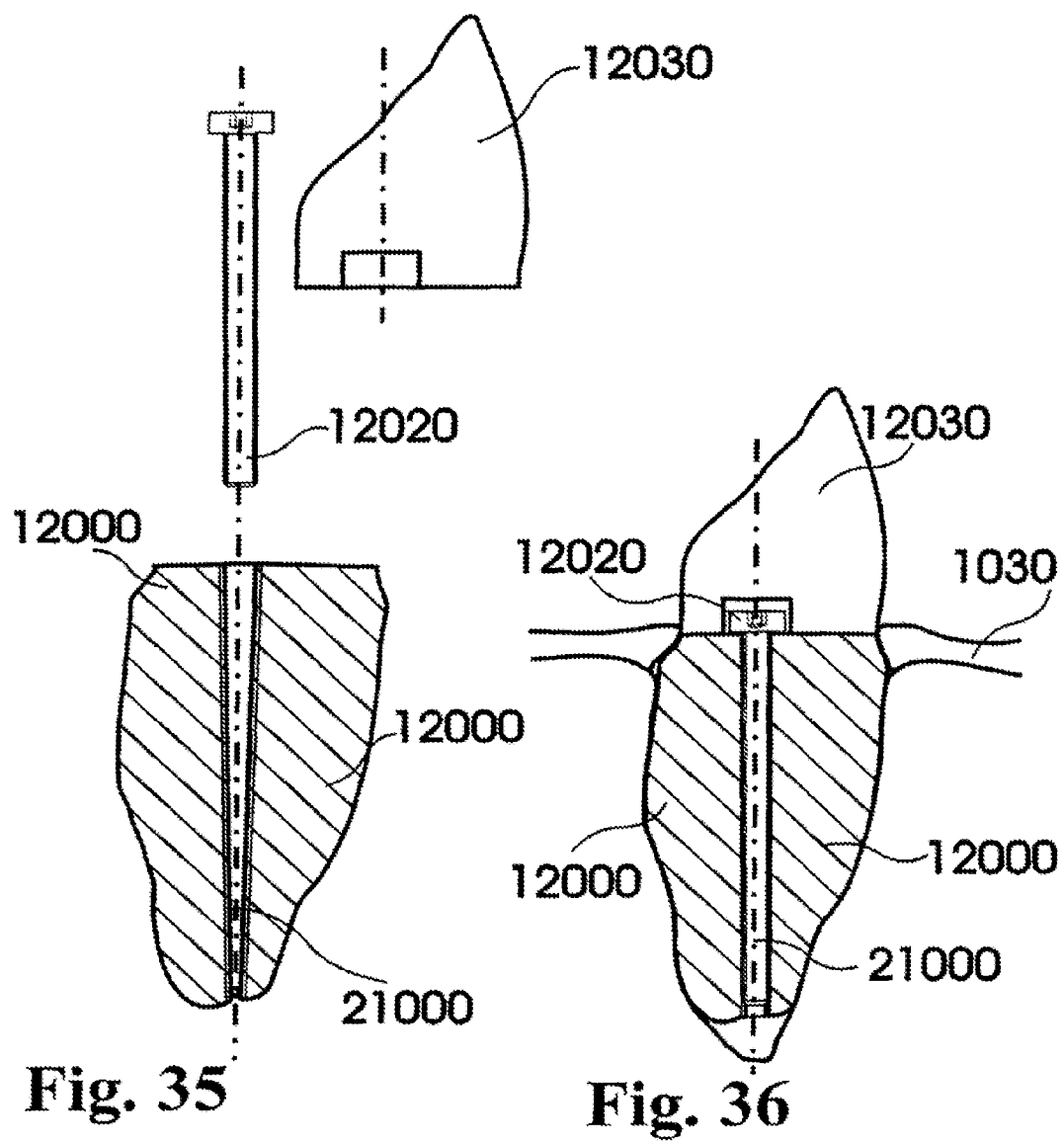
FIG. 35 is a cross-sectional view of the components of a segmented artificial tooth according to an embodiment of the present invention, the segment representing the root being expandable by being slotted and having a conical thread.
FIG. 36 is the artificial tooth of FIG. 35 inserted into the extraction socket and being expanded by inserting screw into the conical thread according to an embodiment of the present invention.

In yet another embodiment of the present invention, firm anchoring of the implant is achieved by expanding the portion being located in the extraction socket in order to support osseointegration and improve physical stability after the implantation. By expanding the implanted portion, forces are applied to the alveolus or bone. In this embodiment of the present invention, the artificial root is shaped to form an expansion anchor. Expansion can be achieved by either using a material changing its shape due to temperature changes after insertion like SMA (shape memory alloy) or by using a material like shape memory polymers activated by electromagnetic radiation. Expansion can also be achieved mechanically by placing a dowel inside the artificial root. This is demonstrated in FIGS. 13 and 15. The root portion of the implant is slotted, thus forming posts or wings (12000) and made from a material providing sufficient elasticity in conjunction with the slots. When screw (12020) is inserted into dowel (12010), the posts are pressed against the walls of the extraction socket. The crown (12030) is attached to the implant after insertion, using standard procedures known in prior art. FIG. 16 displays such an implant located in an extraction socket where voids have been filled with a substance (13000) promoting bone growth like Bioplant or CERASORB. In FIG. 35, another embodiment is displayed. No dowel is used, but instead the thread is conical. When screw (12020) is inserted into the conical thread, the wings (12000) are accordingly expanded and pressed firmly against the extraction socket, as demonstrated in FIG. 36. Alternatively, the initial pressure supporting the fast integration into the bone may be performed by, for example, three oversized small grooves positioned on the outer surface parallel to the londigitudinal axis of the root causing pressure when the artificial root is inserted.

To achieve a long living prosthesis the size and the shape of the root and the socket needs to be appropriate to enable solid anchorage in the bone. If, for example, a root is too small to absorb the normal chewing forces, it may be necessary to expand the size of the socket before designing and manufacturing the customized root. Other patients may not have enough bone material, so that the thickness of the bone gingivally and labially is not sufficient for the anchorage of an implant. In such a case, the root may be shaped like a clamp so that the corticalis is used for the anchorage. This approach is known as "juxtaosseous" method (the implant adapts to the bone and not the bone to the implant). If an appropriate material like titanium in combination with biological ossifying substance is used, the bone adapts to the implant and so the implant becomes an osseointegrated implant. For abutments, this is already successfully being used by the San Babila Day Hospital in Italy. Even more solidity can be achieved by a "multi-legged" root shape combining an artificial root and clamp shaped outer part for the adaptation to the corticalis. This approach significantly increases the stability of the anchorage because no hollow or less stabile areas remain in the bone. If crown and root are manufactured as one unitary part, the crown can be coated with an enamel-colored layer or multiple layers for aesthetic reasons. Such layer(s) can be, for example, translucent to certain extent. During the healing process, appropriate measures need to be put in place to avoid early exposure of the implant to forces (bite bumpers, partials positioners, etc.).

Figure 20:
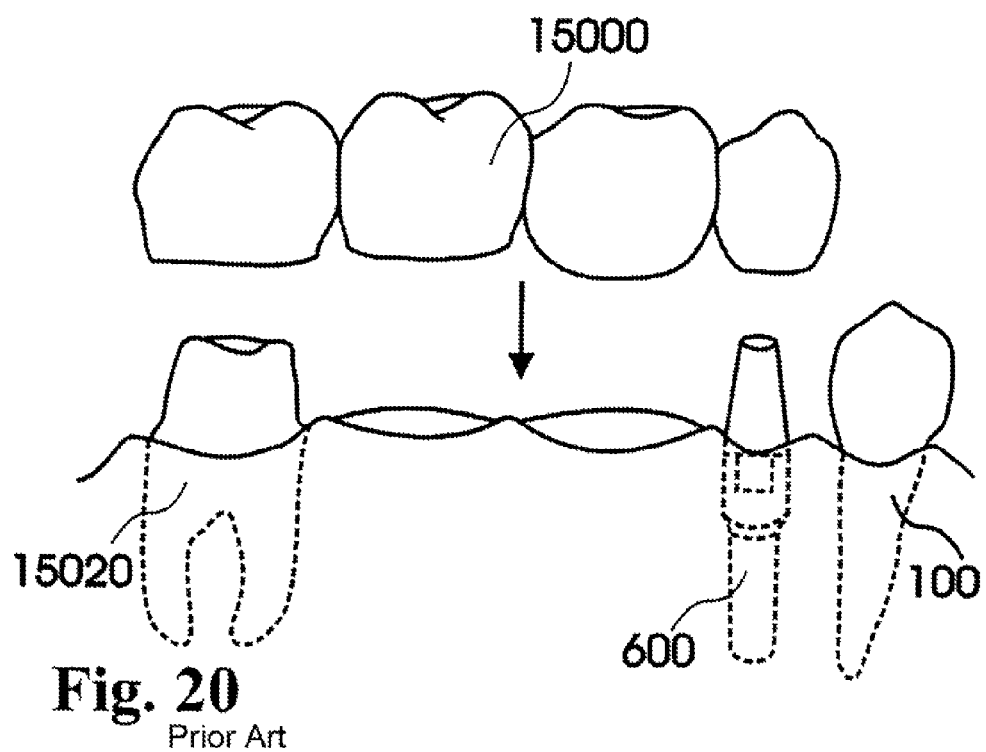
FIG. 20 is a view of a bridge according to prior art.
Figure 21:
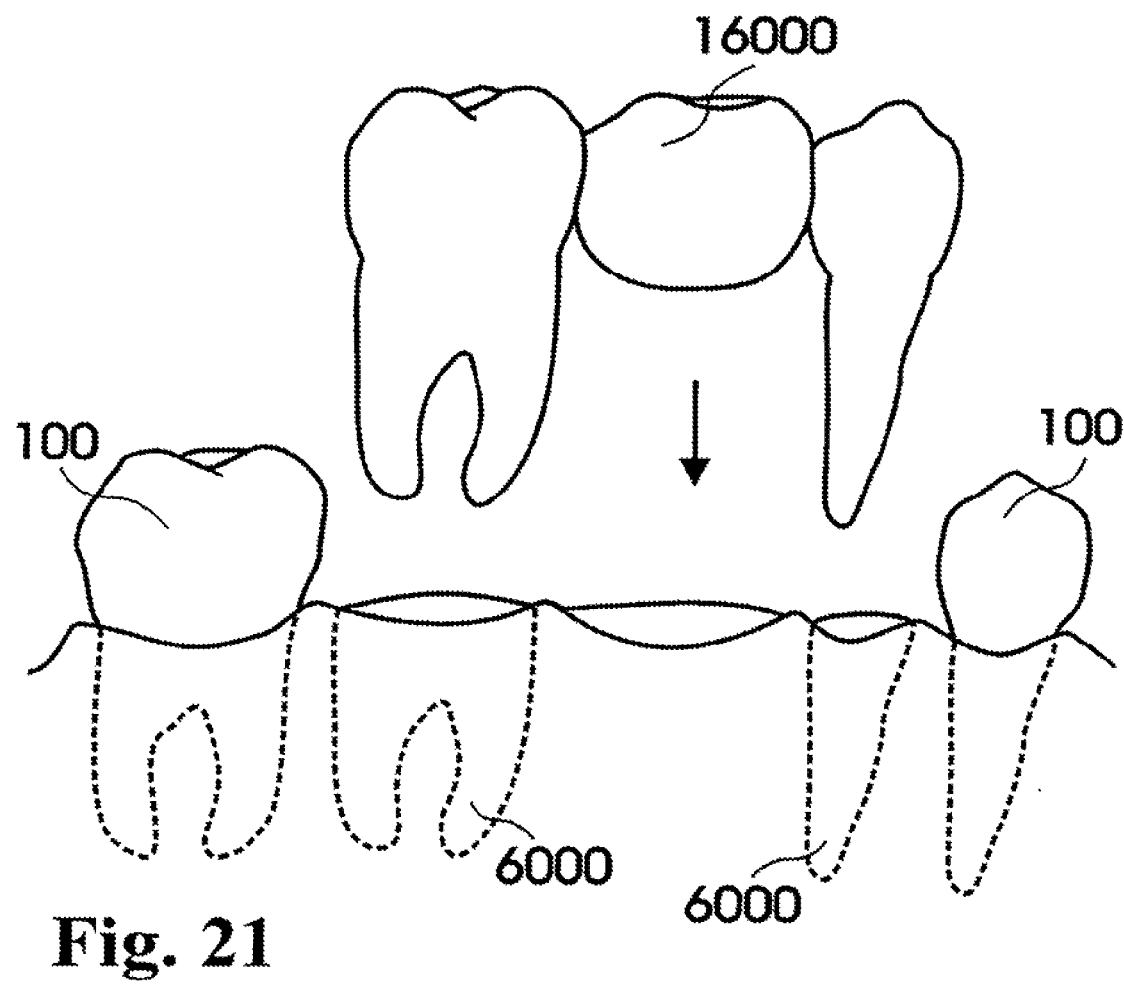
FIG. 21 is a view of a bridge according to an embodiment of the present invention.

The various embodiments of the present invention are not limited to the replacement of a single tooth. It is possible to manufacture dental bridges, the lateral teeth having root features that can readily be implanted into an existing socket. Conventional dental bridges (15000) as displayed in FIG. 20, for example, are cemented onto natural teeth with the crown being grinded down (15020) or onto conventional implants (600). According to this embodiment of the present invention, the natural sockets (6000) can be used as shown in FIG. 21 for attaching the bridge (16000), the adjacent teeth (100) staying healthy and complete. It is also possible to fabricate a partial prosthesis to be implanted into the natural socket, with the prosthesis being the anchor for a later installment of a dental bridge. This embodiment is especially useful in cases where one of the two lateral supports of the bridge is already present, and the bridge, therefore, needs to be cemented.

Due to the ability of the suggested manufacturing processes, various embodiments of the present invention allow the fabrication of prostheses representing crowns, roots, bridges, segments or any combination thereof, and also the entirety of a dentition.

In another embodiment of the present invention, off-the-shelf abutments can be integrated into the artificial root using the intended connection method recommended by the manufacturer, such as, for example, screwing them into the artificial root with or without drilling a hole, clicking them onto a counter shape, or others.

In yet another embodiment of the present invention, the components will be molded directly into the artificial root.

Figure 11:
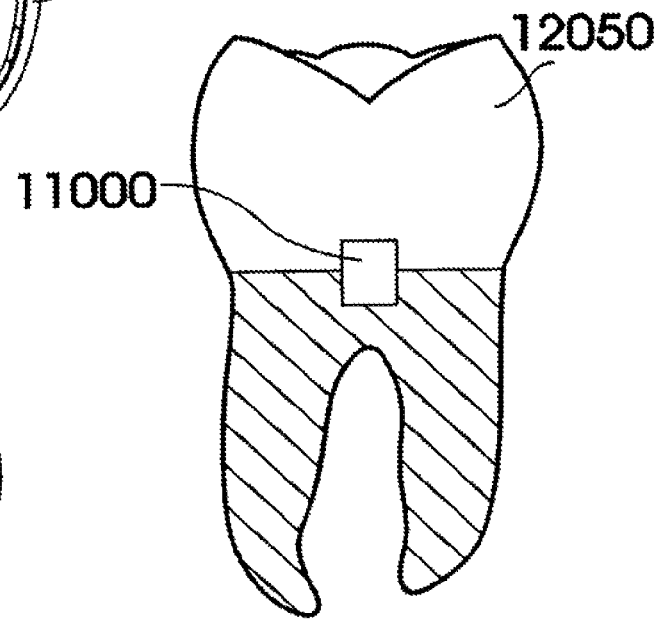
FIG. 11 shows a view of a segmented artificial tooth, the segment representing the root being connected to the segment representing the crown by a connecting element according to an embodiment of the present invention.
Figure 12:
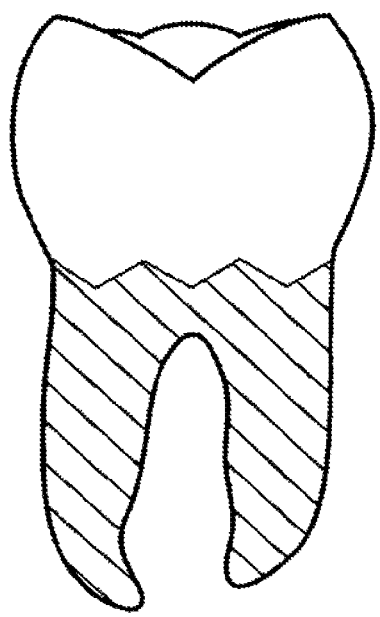
FIG. 12 is a view of a segmented artificial tooth, the segment representing the root and the segment representing the crown having an interlocking connection according to an embodiment of the present invention.

In yet another embodiment of the present invention, the artificial root can comprise a feature on its occlusal-facing surface shaped in a way that it allows for assembly of a conventional veneer or a pre-manufactured veneer or crown to the root. The occlusal-facing surface can also be shaped to provide an interlocking connection to the crown as shown in FIG. 12. The occlusal surface can also have all kinds of connecting features (11000) symbolized in FIG. 11 to allow for attachment of a crown (12050).

Figure 18:
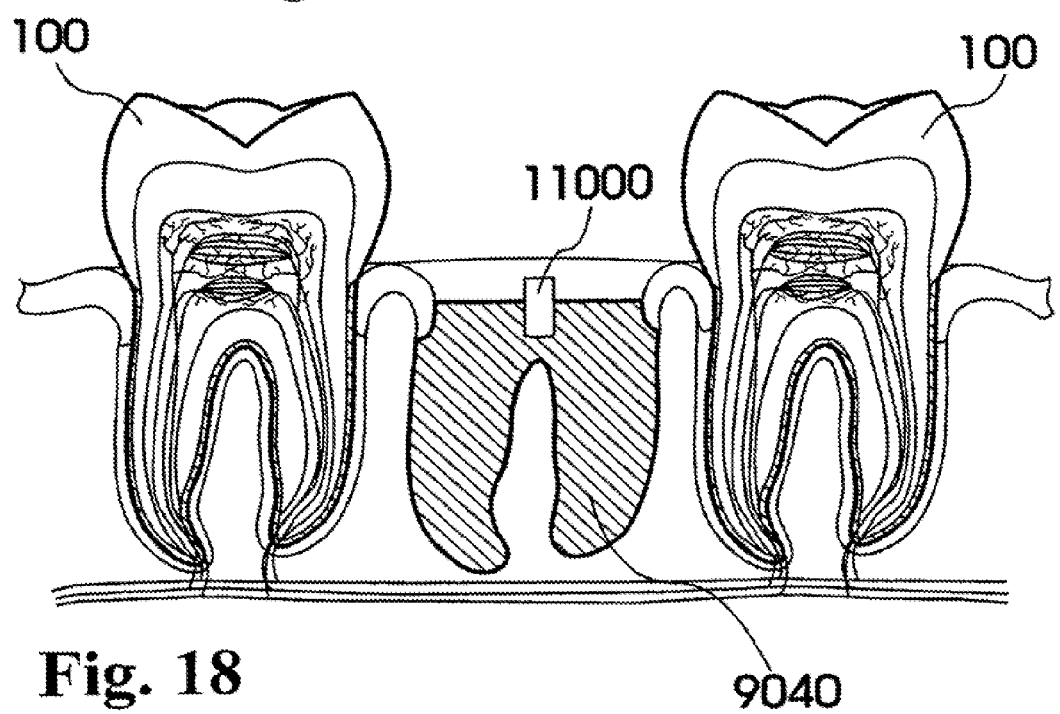
FIG. 18 shows an extraction socket of a patient, the socket filled with a bone promoting substance, and a connection element for the root being embedded into the bone promoting substance.
Figure 19:
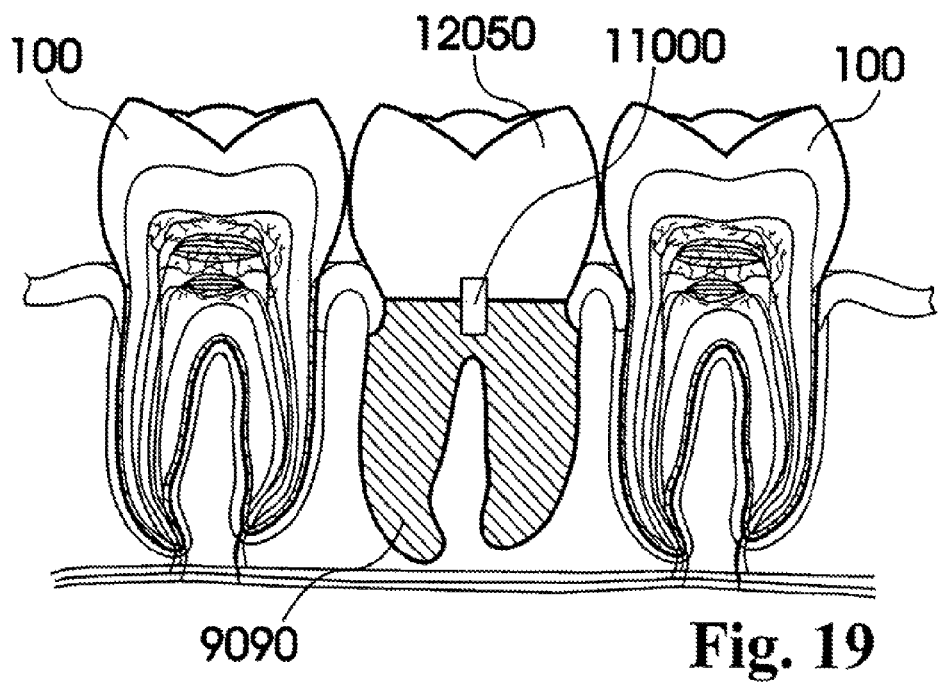
FIG. 19 shows an artificial crown attached to the connection element of FIG. 18 after the bone promoting substance has been replaced by newly grown bone.

In yet another embodiment as shown, for example, in FIG. 18, the extraction socket can be filled with a bone promoting substance (9040), and a connection element (11000) for the root is embedded into the bone promoting substance. FIG. 19 shows the artificial crown attached to the connection element of FIG. 18 after the bone promoting substance has been replaced by newly grown bone (9090).

In another embodiment of the present invention, the time needed for the adoption into the periodontal ligament can be reduced and/or the strength and/or the life-time of the connection to the surface of the artificial root can be optimized by increasing the surface by sandblasting, adding a mesh or other suitable means, and/or pharmaceutics or other substances supporting the integration of the chosen material of the artificial root into the periodontal ligament like the protein amelogenin. These pharmaceutics can be applied by all conventional or state-of-the-art methods like dry or liquids suspensions to be painted onto the artificial roots before integration, or by injection with a hypodermic needle or intra-orally through pills. Also ancestral cells can be used to support the rebuilding of the periodontal ligament. Membrane techniques may also be used to protect the area dedicated to the relatively slow growing periodontal ligaments from the fast growing gingival epithelium.

In another embodiment of the present invention, decreasing the time needed for the osseointegration and/or to increasing the strength and/or the life-time of the connection to the surface of the artificial root can be achieved by increasing the surface by sandblasting, adding a mesh or other suitable means, and/or pharmaceutics supporting the integration of the chosen material of the artificial root into the bone. These pharmaceutics can be applied by conventional or state-of-the-art methods like dry or liquid suspensions to be painted onto the artificial roots before integration, or by injection with a hypodermic needle or intra-orally through pill and/or ray treatment.

In another embodiment of the present invention, the shape of the artificial root may not completely reflect the shape of the root to be replaced. In order to strengthen the connection with the periodontal ligament or the bone, the shape can be modified. If, for example, the three roots of a molar are located very close to each other, the three roots can be replaced by only one root which will comprise parts of the original shape of the three original roots. There is a great deal of software readily available on the market that allows for easy and intuitive modification of 3D shapes. Both previously mentioned programs MAGICS and SolidWorks are suitable for this task.

In another embodiment of the present invention, the closure of remaining gaps between the artificial root and the socket used for implantation can be accelerated by suitable pharmaceutics and/or ray treatment.

In yet another embodiment of the present invention, the prosthesis is an assembly of one or more parts where the interfaces between such parts are sealed in order to provide a barrier against bacteria infiltration. The sealing can include, for example, a labyrinth feature.

In another embodiment of the present invention, the root portion of the prosthesis is an assembly that is configured to extend one or more barbed hooks, which in an embodiment of the present invention, are each connected to the root body with a hinge and activated by a leave spring.

Figure 37:
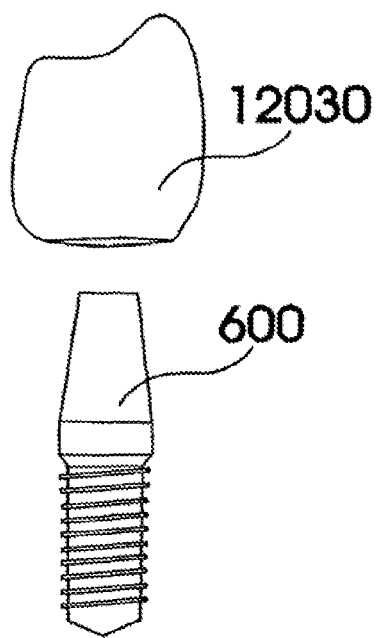
FIG. 37 is a known two-part implant for osseointegration.
Figure 38:
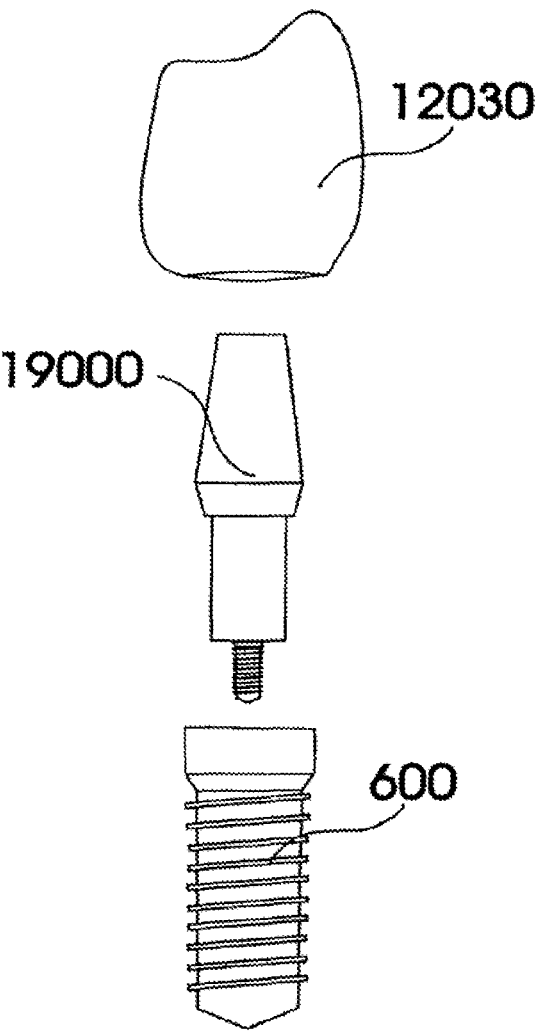
FIG. 38 is a known three-part implant for osseointegration.

Conventional two-piece implants such as, for example, those shown in FIG. 37, consist of an implant (600) to be osseointegrated that includes an abutment portion and an artificial crown (12030). Conventional three-piece implants as shown FIG. 38 consist of an implant (600) to be osseointegrated, an abutment (19000) and an artificial crown (12030). In either configuration these conventional implants (600) and the abutment (19000) are mass produced and have a generic shape. The artificial crown (12030) will be made in a dental laboratory based on impressions of the embedding dental situation which includes the abutment portion of the implant after integration into the dental anatomy of the patient. In other words, the crown will be made based on the geometrical relation between the implant and the abutment (portion) after placement.

Figure 39:
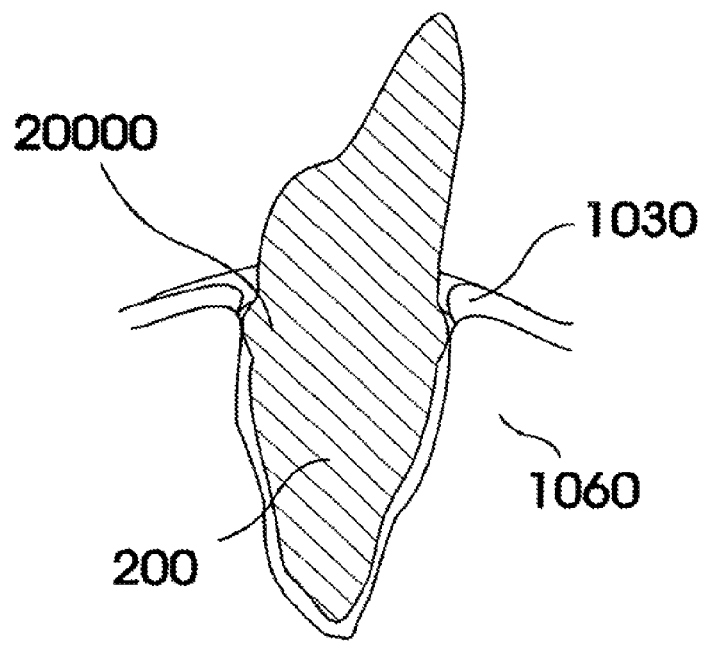
FIG. 39 is a single-tooth prosthesis for osseointegration showing a custom shaped torus as a barrier against tissue growth according to an embodiment of the present invention.

In contrast, the prosthesis according to an embodiment of the present invention is manufactured in all its parts or as a single piece in its entirety before being integrated into the dental anatomy of the patient of interest. FIG. 39, for example, shows a tooth-shaped one-piece prosthesis having an integrated root portion and an integrated crown portion (200). The prosthesis (200) can be shaped with or without a custom shaped torus (20000) that circumvents the prosthesis in a height of, for example, 0.5 mm below the line of gingiva (1030). The torus (20000) builds a barrier against in-growth of the gingival tissue. In case the prosthesis (200) is configured for osseointegration, the cavity in the bone (1060) is virtually sealed, and osseointegration will take place without being disturbed by isolating lobes of gingival tissue growing between the prosthesis and the cavity. In case the prosthesis (200) is configured for periodontal integration, the gap between the prosthesis and the extraction socket is sealed against fast growth of gingival tissue, so that the integration into the periodontal ligament structures, having a reduced growth rate in comparison, is protected.

In yet another embodiment of the present invention, the prosthesis is an assembly of two or more parts, as shown, for example, in FIGS. 5, 6, 8, 11, 12, 13, 15, 16, 18, 19, 31, 34, 35, 36, and 45. The parts are, for example, glued, sintered, mounted by pressure, and/or screwed to each other, and the interface between connecting parts needs to be sealed against bacteria infiltration. Special sealing concepts like O-ring sealing and labyrinth sealing may apply.

Figure 40:
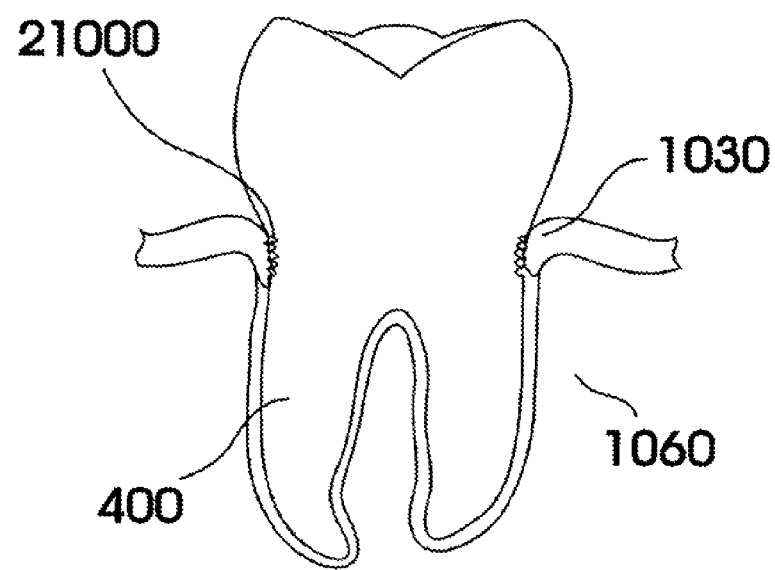
FIG. 40 is a single-tooth prosthesis showing a labyrinth-sealing feature as barrier against bacteria infiltration according to an embodiment of the present invention.

In another embodiment of the present invention as shown in FIG. 40, the prosthesis (400) has a sealing feature (21000), which is circumventing or partially placed between the crown portion and the root portion of the prosthesis (400). The sealing feature (21000) is either simply an indent or a labyrinth feature that builds the interface between the material of the prosthesis and the gingiva (1030). The respective interface seals the structure between the prosthesis and the extraction socket against bacteria infiltration in order to gain long-term stability and to avoid pockets.

Figure 41:
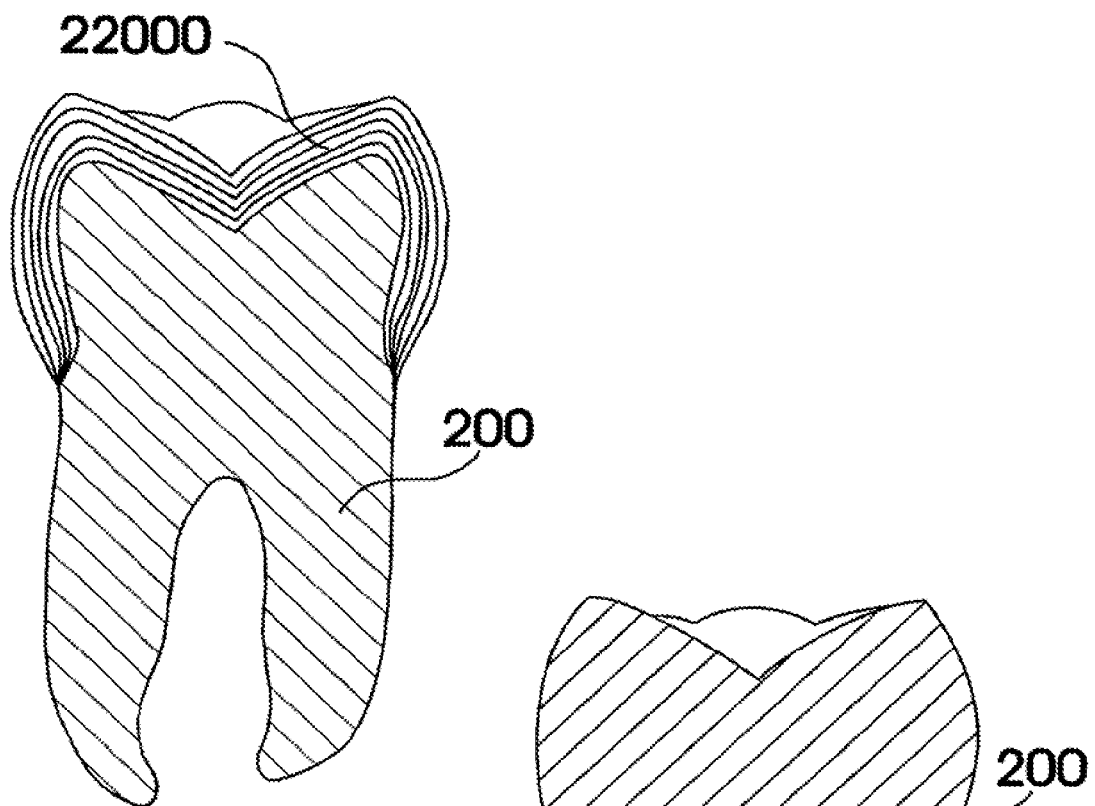
FIG. 41 is a single-tooth prosthesis showing a build-up of a crown portion of translucent ceramic layers according to an embodiment of the present invention.

In another embodiment of the present invention, the crown portion of the prosthesis is fabricated in an undersized shape compared to the final shape of the crown. Single or multiple layers of translucent ceramics are added in a laboratory process to gain esthetic performance compared to the appearance of a natural tooth. FIG. 41, for example, is a single tooth prosthesis having an undersized crown shape (200) and a build-up of several ceramic layers (22000). It is also possible to use other esthetic materials having one or more than one layer. In another embodiment of the present invention, the build-up (22000) is, for example, made of elastic materials (like an elastic cover) in order to soften early contacts and fostering this way the healing process after integrating the prosthesis.

Figure 42:
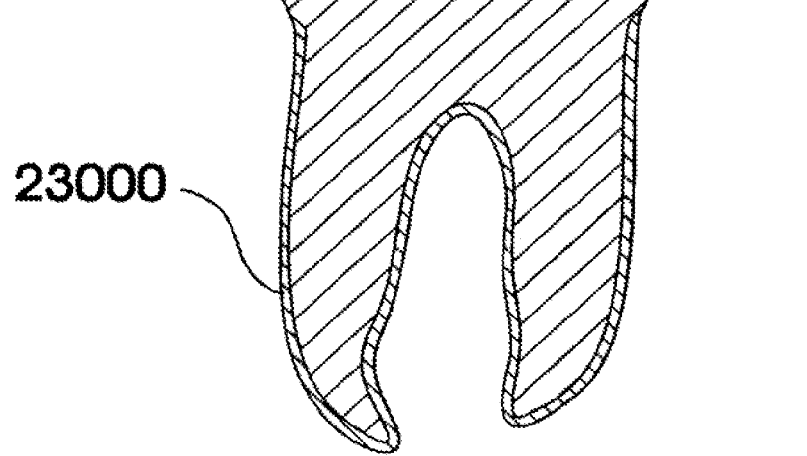
FIG. 42 is a single-tooth prosthesis showing a root portion having drug releasing surface according to an embodiment of the present invention.

In yet another embodiment, the prosthesis is at least partially made of one of the following: titanium, titanium alloy that consists of more than about 60% of titanium, cement, zirconium oxide, ceramics, synthetics, elastics, plastics, stainless steel, glasiomer cement, resin-ionomer cement, hybrid-ionomer cement, resin-enforced cement, and acrylic based photopolymer, or any combination thereof. In a further improvement the prosthesis includes a drug releasing surface, releasing over time medical substances. Such substances include, for example, one of the following: Antibiotic or other infection suppressing pharmaceuticals, growth promoting substances (for example, ancestral cells, proteins, and cell parts of a human or animal tooth) or any combination thereof. FIG. 42 is, for example, a single-tooth prosthesis (200) having a drug releasing surface (23000) covering at least a portion of the root part of the prosthesis (200).

In yet another embodiment, a prosthesis is fabricated based on imaging data of the patient's dental anatomy, which includes three-dimensional representations of one tooth or two or more teeth. Each tooth includes a crown portion and root portion. The imaging data can be made either prior to or after extraction of the tooth or teeth to be replaced. The imaging data can include in-vivo data or data made in-vitro from one tooth or two or more teeth after extraction. Other imaging data are derived from physical impressions made of a dental anatomy. Dental anatomy includes the occlusion, the articulation, and the geometrical (spatial) relationship between the teeth within one arch or between upper and lower arch of a patient, or parts thereof. The dental anatomy also includes the structures holding the tooth/teeth which include soft tissue structures and bone structures and any combination thereof. Imaging data can include two dimensional representations such as, for example, X-ray films, facial photos, etc., or three-dimensional representations such as, for example, CT or MRT data and the like. The imaging data can be any portion of the aforementioned data and/or any combination thereof. All these imaging data can be merged, overlaid and combined to derive shape data of a design of the prosthesis.

Figure 43:
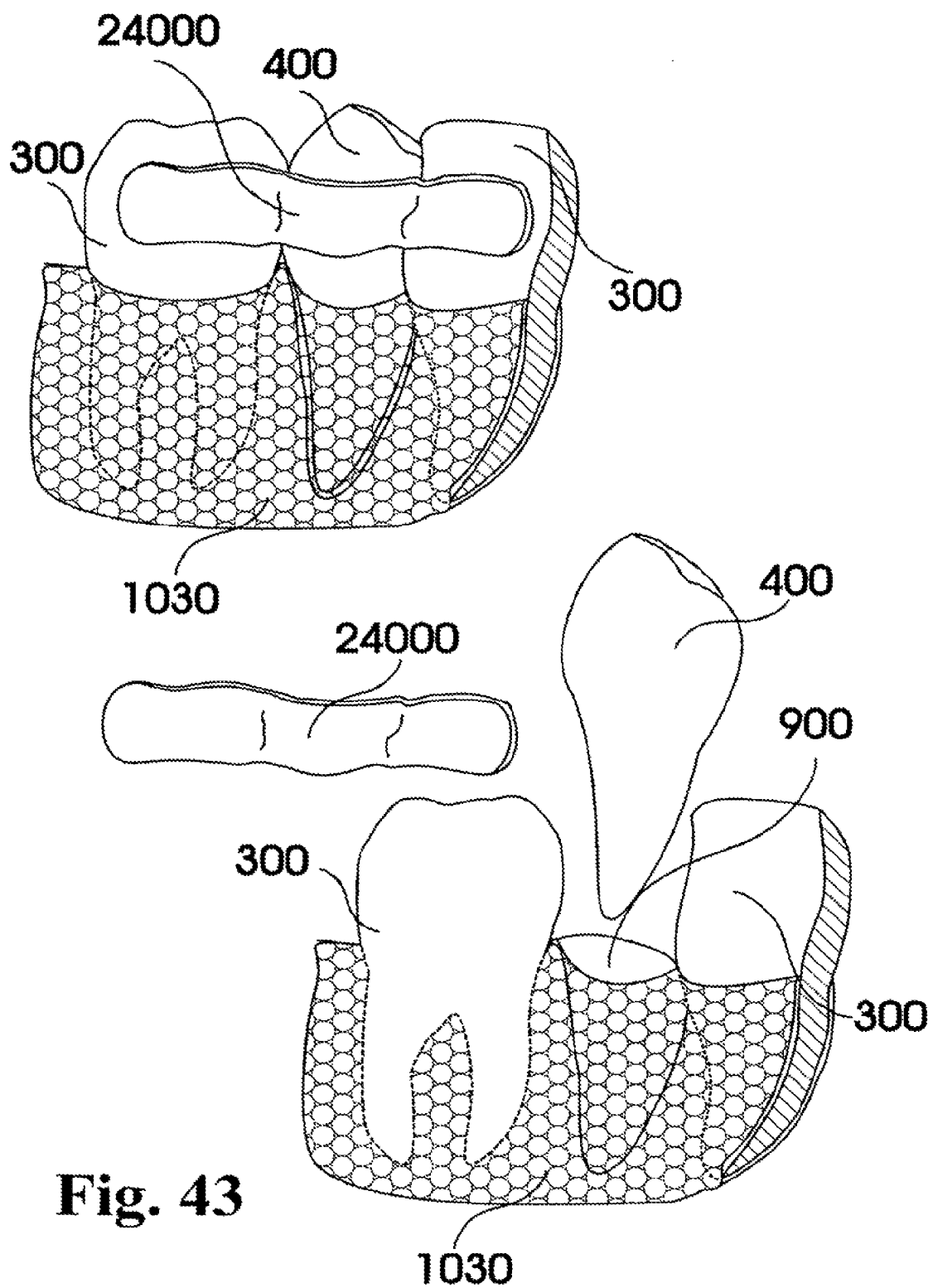
FIG. 43 is a single-tooth prosthesis and a custom-made splint for positioning and fixation of such to the adjacent dental structure according to an embodiment of the present invention.

In another embodiment of the present invention shown, for example, in FIG. 43, a single-tooth prosthesis (400), having a manufactured crown portion and a manufactured root portion is provided. The shape of each is derived, for example, from in-vivo imaging data prior to the extraction of the tooth to be replaced. By extraction of the natural, e.g., nonfunctional tooth to be replaced, the extraction void (900) was created. The adjacent teeth, e.g., mesial and distal of the extraction socket, are healthy natural teeth (300). The extraction was indicated, for example, due to a serious porosity of the root of the extracted tooth. The extraction socket was partially curetted by the doctor of record, removing damaged soft tissue. Antibiotic tablets are given orally to the patient in advance to suppress the inflammation and to avoid additional infection as a result of the clinical trauma of removing the tooth. The crown and the root shape are derived from the imaging data. In addition, the crown shape of the adjacent teeth (300) and a desired position and inclination of the prosthesis are derived from the imaging data. Based on all this data a custom-shaped splint (24000) is designed and fabricated. The splint is used to position and orient the prosthesis (400) in the dental structure (1030) building the extraction void in geometrical relation to the adjacent teeth (300). Being held in the desired position and orientation, the custom-shaped splint (24000) is glued with adhesive means to the prosthesis (400) and the adjacent teeth (300). For example, light curing adhesives can be used in that context. Finally, the prosthesis (4009 is fixated in its desired position and the crown portion is thereby integrated into the occlusion and articulation of the patients dental anatomy. Slight corrections performed by the doctor of record with a high-speed rotating instrument may be necessary to optimize the occlusal contact points. The prosthesis can be immediately loaded by the patient for the day-to-day use of mastication. That is, according to this embodiment of the present invention, the custom splint glued to the prosthesis and adjacent teeth or other dental structures beneficially provides the primary stability while either the periodontal integration or the osseointegration takes place.

Figure 44:
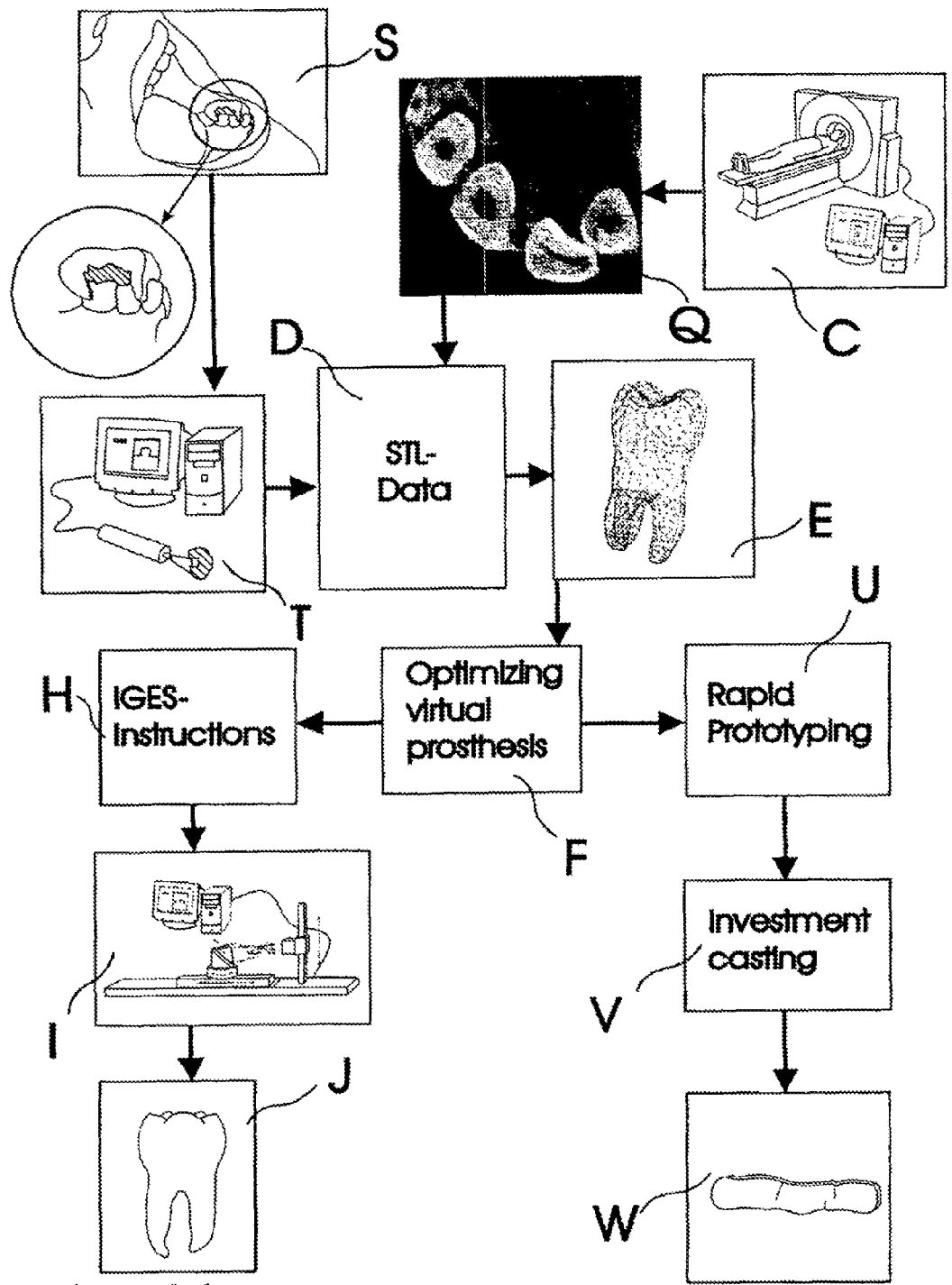
FIG. 44 shows the process steps of fabricating a one-piece prosthesis partially from in-vivo imaging data and partially from imaging data of impressions, merging those imaging data, design a prosthesis and a custom splint, and fabricating the prosthesis and the splint by computer numerical control (CNC) machining according to an embodiment of the present invention.

In the context of the aforementioned custom splint, FIG. 44 shows, for example, the process steps of fabricating such a dental prosthesis and such a splint according to an example of the embodiment of the present invention. A partial silicone impression is taken from the mouth of the patient representing the dental (occlusal) crown anatomy in the neighborhood where a prosthesis will be integrated (step S). The impression is scanned and three-dimensional STL data of the shape are derived representing the crown geometry of the tooth to be extracted, the crown geometry of the adjacent teeth, and the geometrical relation between those crown data (step T). Additionally, the patient's dental anatomy is imaged with a computed tomography device (step C). Computed tomography (CT) is a medical imaging method employing tomography where digital geometry processing is used to generate a three-dimensional image of the internals of an object from a large series of two-dimensional X-ray images taken around a single axis of rotation. The layered grey scale X-ray data in digitized format are computer analyzed, and voxel as well as three-dimensional STL data are derived representing the dental anatomy of the patient (step Q). All aforementioned STL data are scaled, merged and/or combined to generate an accurate three-dimensional shape data from tooth to be replaced and the adjacent dental anatomy (step E). Boolean algorithms are used to generate combined data of high-quality. A first design of the prosthesis, its position and orientation within the adjacent dental anatomy especially in relation to the crown portions of the adjacent teeth and a second design of a custom shaped splint that includes shape portions of the crown of the prosthesis and of the crowns of the adjacent teeth, are derived. The first and the second design may be modified and optimized (step F). This can be done automatically or interactively by having a technician operating the respective computer equipment. Computer numerical control data (CNC), for example, in IGES format for computer aided manufacturing (CAD) devices are derived from the final three-dimensional design data (step H). Usually, rapid prototyping equipment has the aforementioned step already integrated into its functionality. The prosthesis is then fabricated in response to the IGES data, for example, by a CAM high-speed milling/grinding machine (step I and J). Additionally, the rapid prototyping machine such as, for example, a layer-by-layer wax printing machine, fabricates a three-dimensional wax representation (sample) from the three-dimensional design data (step U). The sample is prepared and embedded for lost wax investment casting; the wax sample is burned out and the investment mould is filled with liquid precious metal (e.g., dental gold alloy; step V). After cooling down to room temperature, the embedding material is removed, the runner is cut-off and the splint is polished and surface prepped for bonding (step W). It should be noted that although FIG. 44 contemplates interaction with an operator, one skilled in the art would readily appreciate that certain steps are combined, further differentiated, and that this functionality may be partially or fully automated.

Figure 45:
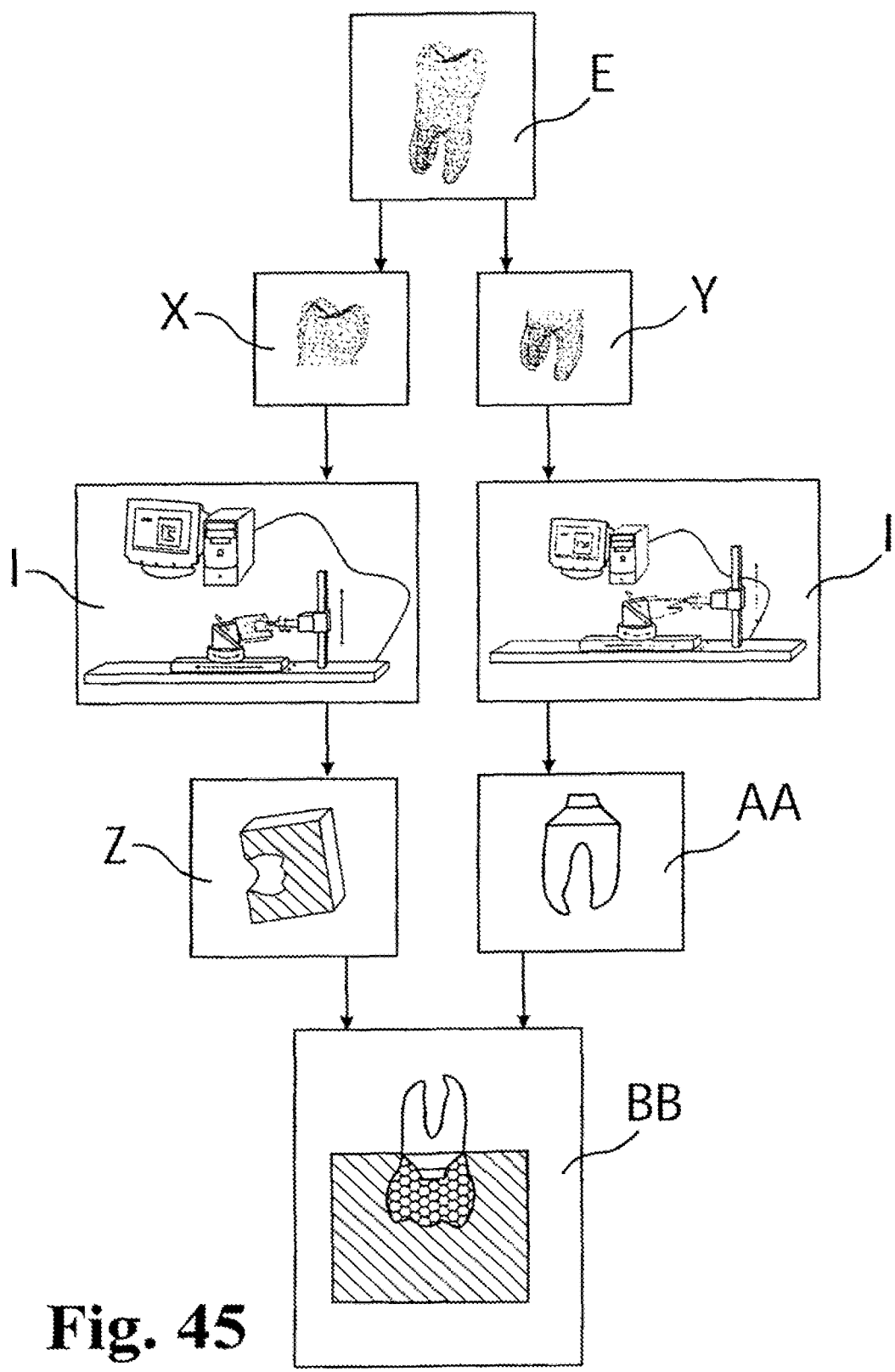
FIG. 45 shows the process steps of fabricating a one-piece prosthesis from design data, completing the design by segmenting the prosthesis in a root portion that includes an abutment and a crown portion, fabricate the root portion by computer numerical control (CNC) machining, fabricating a negative shape of the crown portion as a mould by computer numerical control (CNC) machining, and use the root portion and the mould to complete the one-piece prosthesis shaping the crown portion according to an embodiment of the present invention.

In yet another embodiment of the present invention, the dental prosthesis is segmented and such segments are fabricated using different manufacturing technologies. FIG. 45 shows the process steps of receiving design data of a prosthesis in STL format (step E), separating portions in a computer aided design (CAD) process (step X and Y), deriving computer numerical control (CNC) data and fabricating the respective portions (step Z and AA) in response to the CNC data using computer aided manufacturing (CAM) machinery, for example, high-speed milling/grinding machines (step I). The separated portions are combined to build the prosthesis (step BB).

A specific implementation of the processes of FIG. 45 is described hereinafter. A first segmented design portion, for example, the crown portion of the prosthesis (step X) is not fabricated directly. Rather, an inverse shape such as, for example, the negative representation of the crown shape, is cut (step I) to build a separate work piece, for example, a mould (step Z). The second segmented design portion (step Y), for example, the root portion of the prosthesis, is cut as a positive representation is cut from a workpiece, for example, consisting of zirconium oxide (step I) to build a portion of the prosthesis itself (step AA). The positive part of the prosthesis (e.g., the root portion) is then combined with the negative representation (e.g., the mould carrying the inverse crown shape) to fabricate the missing portion of the prosthesis according to the first segmented design portion (step BB). In a more particular implementation, for example, the mould "Z" is made of a transparent material (acryl glass, polymethyl-methacrylate), prepared with a separating layer (silicone spray), filled with nano-composite usually used for crown restorations (BISICO, Germany), the root portion "AA" is placed in the designed position and inclination to conform to the overall design of the prosthesis, and the composite is cured in a UV-light chamber widely used in dental laboratories (step BB).

Figure 46:
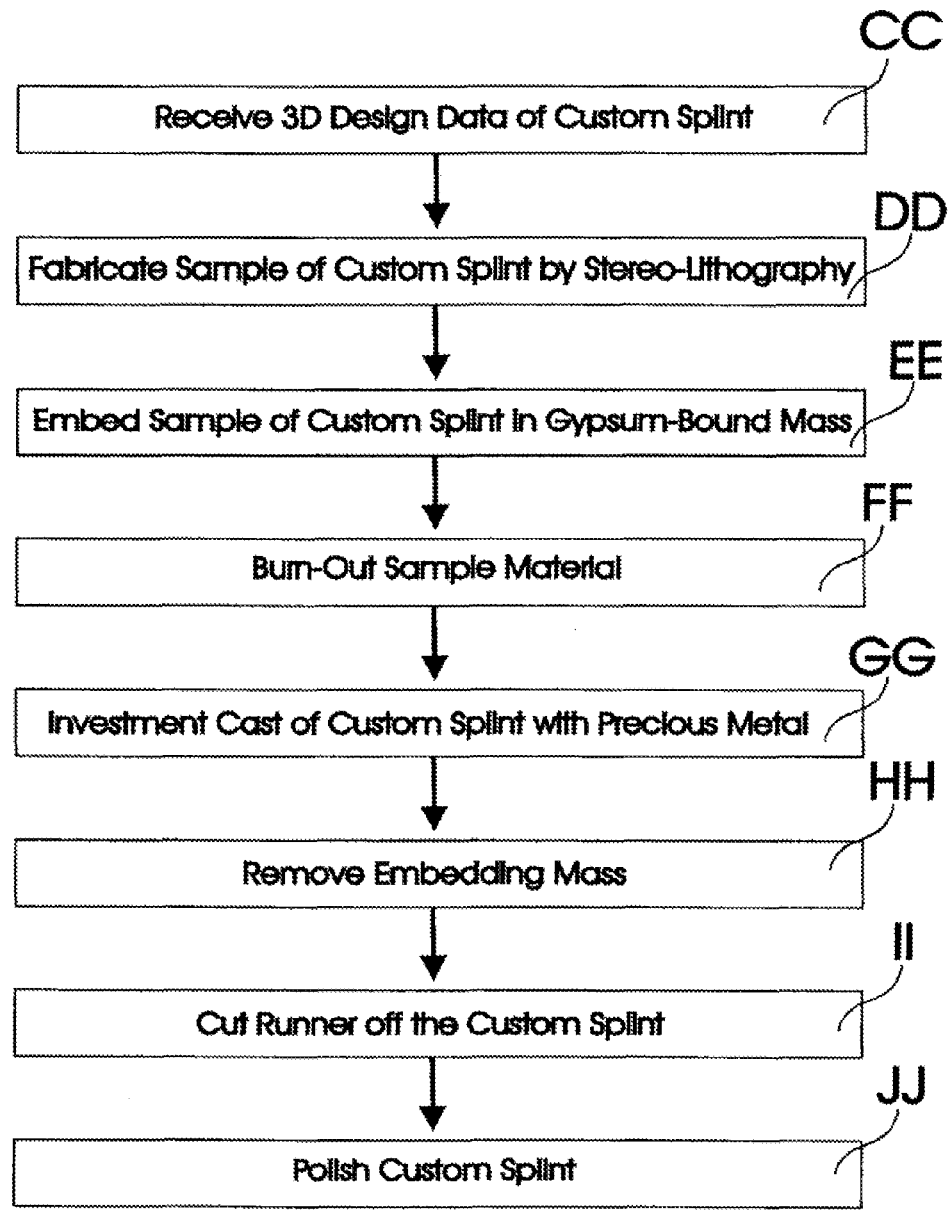
FIG. 46 shows the process steps of fabricating the custom splint from design data, and fabricating a model of the splint by rapid prototyping, build a mould around the splint, burning out the model and cast the splint by investment casting according to an embodiment of the present invention.

In another embodiment of the present invention, the custom splint is fabricated in an indirect method, for example, by lost-wax investment casting. FIG. 46 shows the process steps of fabricating the custom splint from design data, and fabricating a model of the splint by rapid prototyping, building a mould around the splint, burning out the model and casting the splint by investment casting. As shown in FIG. 46, the process starts with receiving the 3D design data of a custom splint (step CC). The sample part of the custom splint is then fabricated using stereo-lithography conforming to the design data (step DD). The sample part is embedded (step EE) in, for example, a gypsum-bound investment material, e.g., Cera Fina, Whip Mix, U.S.A. The investment mould is heated and the material of the sample part is burnt out (step FF). The mould is then filled by vacuum or centrifugal casting with liquid precious alloy, for example, Argenco 42 Type IV extra hard, The Argon Corporation, U.S.A. (step GG), and the embedding mass is removed (step HH). The casting runner is cut from the custom splint (step II), and the custom split is polished and prepared for bonding (step JJ). It should be noted that while FIG. 44 contemplates possible interaction with an operator, one skilled in the art would readily appreciate that certain steps can be combined, or further differentiated, and that this functionality may be partially or fully automated. Alternatively, to the precious metal the investment casting can be done with stainless steel or other suitable non-precious dental alloy known to those skilled in the art.

In yet another embodiment of the present invention, the custom splint is perforated or prepared with retention features on the bonding surface (like a mesh) for better light curing capabilities and better bonding strength.

Figure 47:
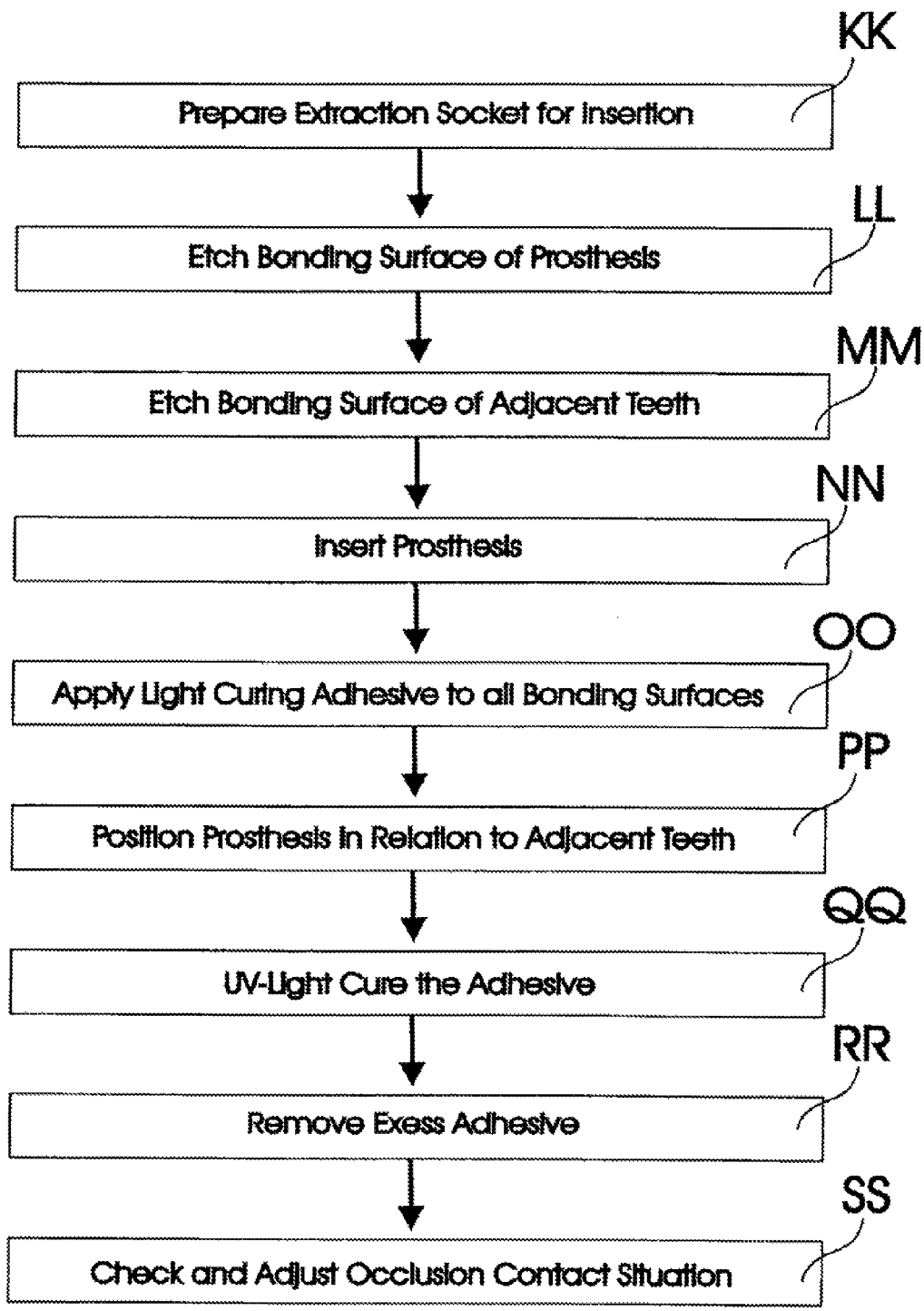
FIG. 47 shows the process steps of clinically inserting a one-piece prosthesis into an extraction socket, positioning the prosthesis in relation to the adjacent teeth with the custom splint and fixating the prosthesis in relation to the adjacent dental structure with adhesive means according to an embodiment of the present invention.

In another embodiment of the present invention, the clinical process of integrating the prosthesis is performed as shown in FIG. 47. The process begins by preparing the extraction socket for insertion, which may include rinsing (step KK), micro-etching (sandblasting) and/or etching the bonding the surface of prosthesis using, e.g., phosphoric acid (step LL), micro-etching (sandblasting) and/or etching the bonding surface of the adjacent teeth or other dental structures (step MM). Once the extraction socket is prepared the prosthesis is inserted (step NN), the process includes applying light curing adhesive to all bonding surfaces (step OO). The prosthesis is then positioned and oriented in the desired geometrical relation to the adjacent teeth or other dental anatomy of interest using the custom splint as a positioning aid or guide (step PP). The prosthesis and the splint are held firmly in position while the adhesive is light cured with a dental UV-light curing device (step QQ) in order to fixate the prosthesis in its desired position. Excess adhesive is removed (step RR), and a final check and adjustment (if necessary) of the occlusion and articulation of the patient in respect to the contact situation of the prosthesis to the teeth or other dental structures of the opponent arch, is performed (step SS).

Figure 48:
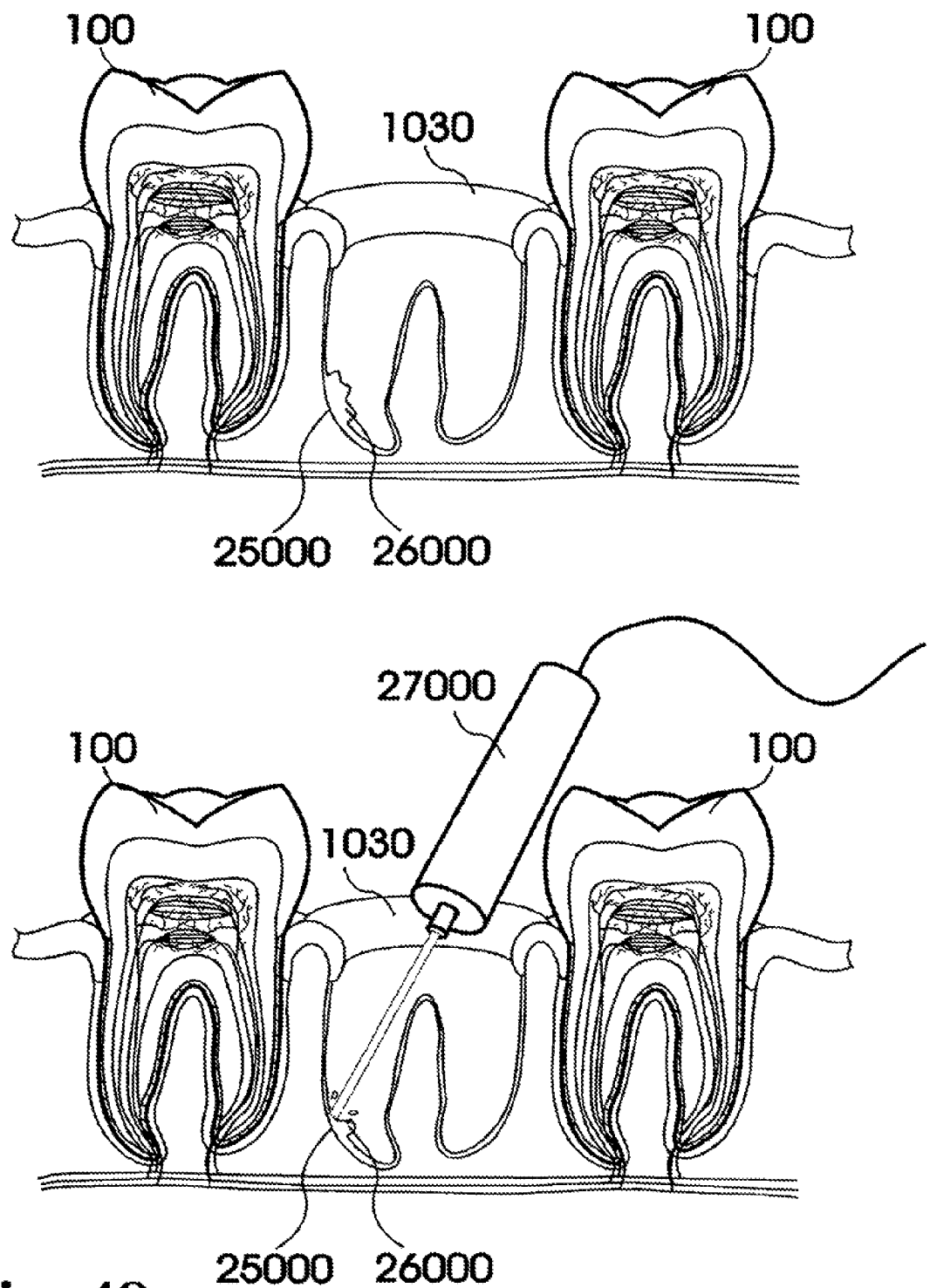
FIG. 48 shows the process steps of clinically preparing an extraction socket with a laser technology based device according to an embodiment of the present invention.

The immediate implantation of a manufactured prosthesis designed and fabricated based on in-vivo imaging data (i.e., obtained prior to the extraction of one or more tooth/teeth of interest) performed directly after extraction may be challenged by non-healthy developments of bone or soft tissue in the extraction cavity. FIG. 48 shows the process steps of clinically preparing an extraction socket by removing decayed soft tissue (26000) and/or decayed bone (25000) with a laser technology based device (27000). The high water content of decayed structures is more absorbent for the laser light energy than healthy structures so that the decayed areas can be easily removed without serious collateral damage of adjacent healthy structures of the dental anatomy. The healing process is this way combined with the integration process of the prosthesis. Negative side effects of bone resorption are reduced by the immediate integration of a dental prosthesis according to any embodiment of this invention. The immediate implementation can be combined with both the dental prosthesis configured for osseointegration and the dental prosthesis configured for periodontal integration.

In yet another embodiment of the present invention, the healing and integration of a prosthesis is facilitated after insertion by using ultrasonic or other vibrations applied to the prosthesis by special dental devices.

Figure 49:
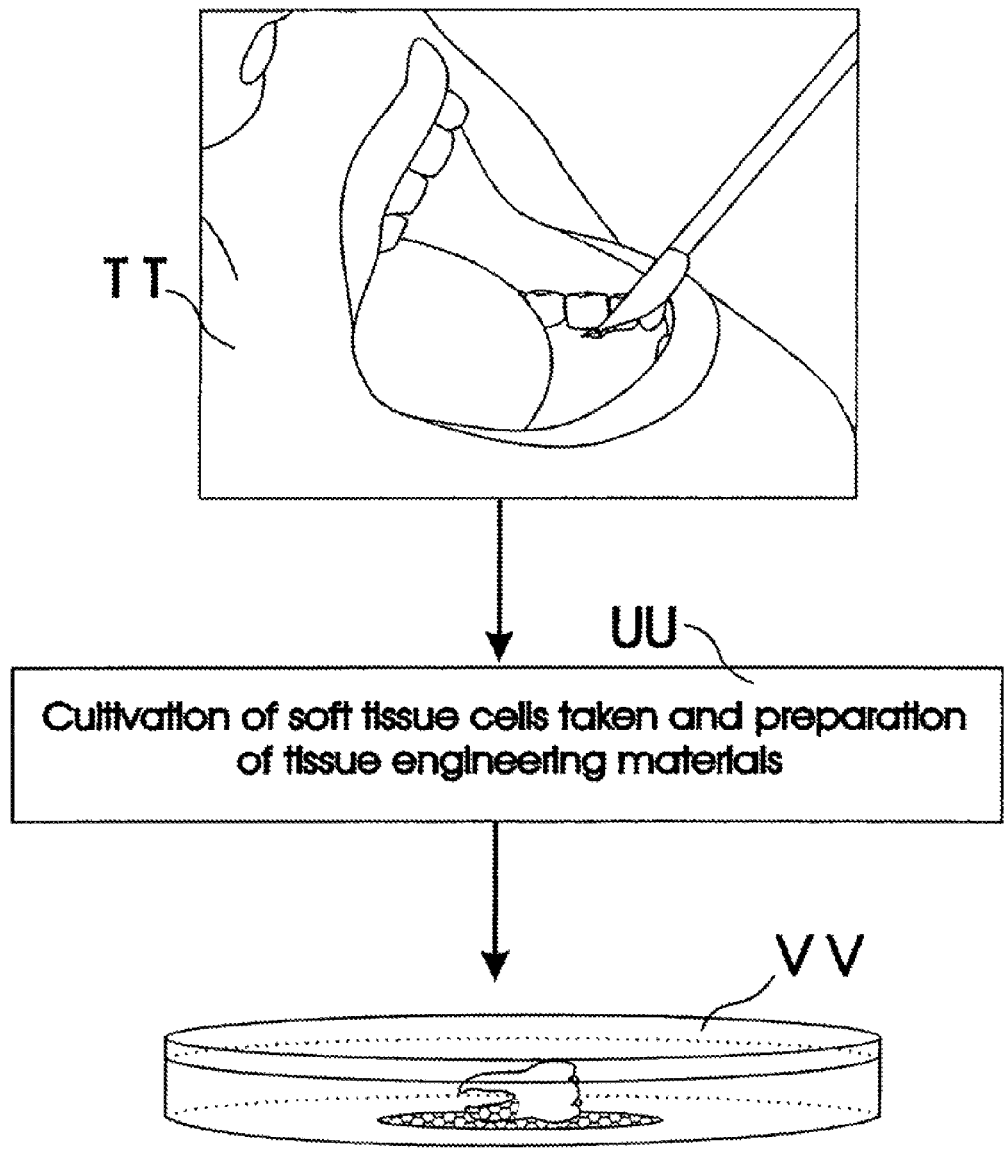
FIG. 49 shows the process steps of manufacturing a prosthesis where autologous biological tooth or tissue material is taken from a patient to be used in an tissue engineering process to configure the root portion of the prosthesis for periodontal integration according to an embodiment of the present invention.
Figure 50:
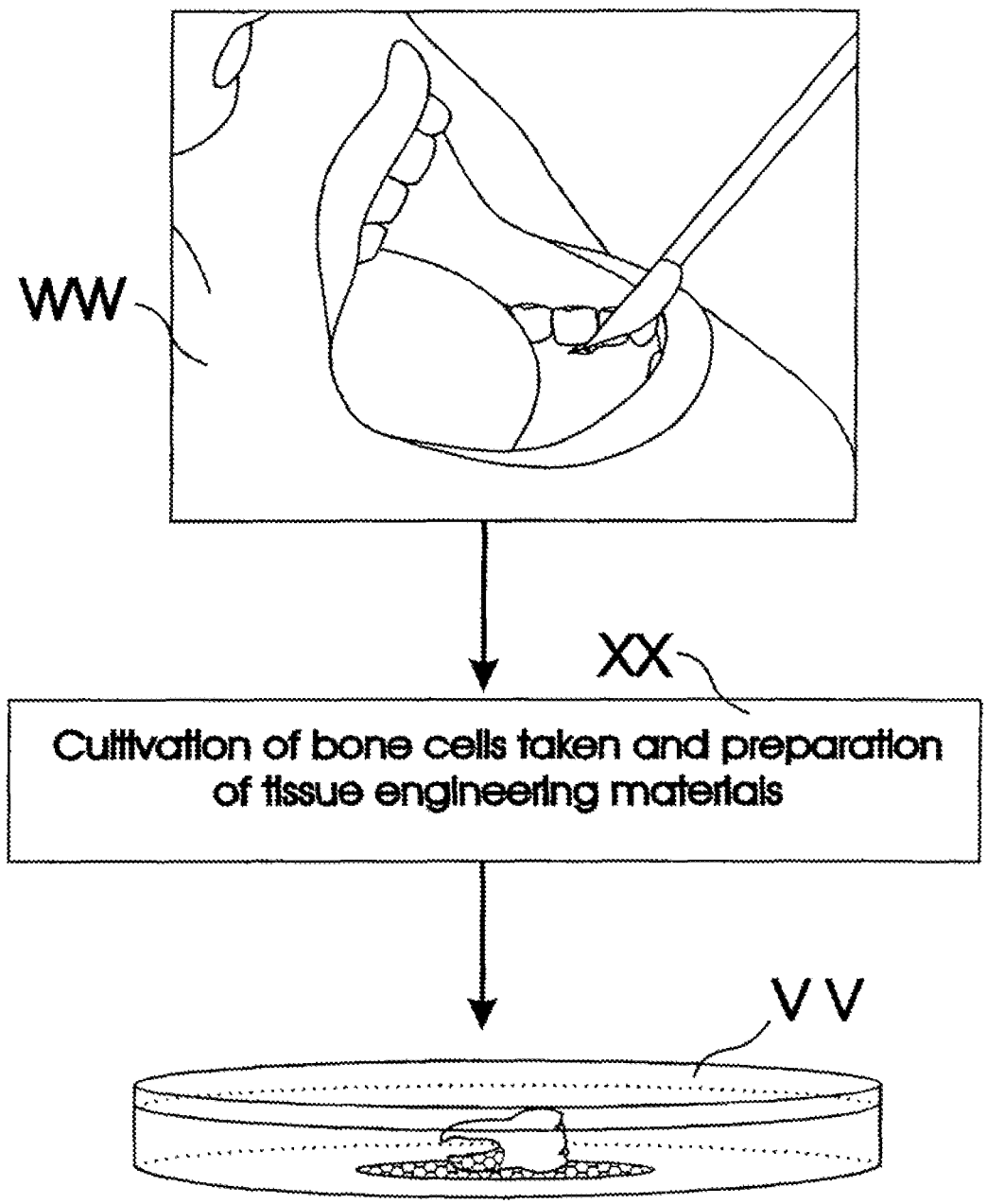
FIG. 50 shows the process steps of manufacturing a prosthesis where autologous biological bone material is taken from a patient to be used in an tissue engineering process to configure the root portion of the prosthesis for osseointegration according to an embodiment of the present invention.

Beneficially, the integration of the prosthesis described herein can be facilitated and actually accelerated by techniques of surface coating based on tissue engineering. FIG. 49 shows the process steps of taking autologous soft tissue cells from the patient (step TT), culturing such soft tissue cells in an in-vitro assay system (step UU), and applying such cells with or without other tissue engineering materials to the root portion of the prosthesis (step VV). FIG. 50 shows the process steps of taking autologous bone cells from the patient (step TT), culturing such soft bone cells in an in-vitro assay system (step XX), and applying such cells with or with out other tissue engineering materials to the root portion of the prosthesis (step VV). In both aforementioned scenarios, the soft-tissue or bone structures are taken with a sharp instrument, for example, an exenteration scoop like a Chalazion curette. Other exenteration techniques may apply.

In another embodiment of the present invention, human periodontal ligament (HPDL) fibroblasts are used and a prosthesis, according to other embodiments of the present invention, is placed in tissue culture clusters, whereby an amount of 1 ml of HPDL fibroblast cell suspension is placed over the root portion of the prosthesis and then placed into an incubator at 37° C. and 100% humidity for 72 hours. With that, the cells of HPDL fibroblast are extending and attaching firmly to the prosthesis surface by cytoplasmic extension of the lamellipodia and microvilli to extend into porous (micro) surface structures.

In yet another embodiment of the present invention, stem cells can be used to produce HPDL fibroblast or other acellular and cellular structures of the human dental anatomy such as, for example, acellular and cellular cementum, which is mineralized tissue covering the root dentin that serves to anchor periodontal ligament fibers, and/or cementoblast, which are cells found on the surface of cementum being responsible for its synthesis.

Alternatively, to the aforementioned use of autologous material, human allogenic bone, root or tissue substances can be used. Alternatively, to the use of human bio material tooth, animal-derived bone or tissue material, for example, bovine cells or even synthetic materials, can be used for in the various process steps of tissue engineering.

In yet another embodiment of the present invention, the tissue engineering techniques include the coating of the root portion(s) of the prosthesis with collagen incorporating growth factor substance, for example, platelet-derived growth factor (PDGF).

The aforementioned tissue engineering technologies may employ in the aforementioned context, for example, living cells of various kinds such as engineering materials, autologous cells, which are obtained from the same individual to which they will be reimplanted, mouse embryonic stem cells, allogenic cells, which come from the body of a donor of the same species, xenogenic cells, which are isolated from individuals of another species, syngeneic or isogenic cells, which are isolated from genetically identical organisms, such as twins, clones, or highly inbred research animal models, primary cells from an organism, secondary cells are a cell bank, and stem cells. In this context, tissue engineering shall also include the use of artificial structures capable of supporting three-dimensional tissue formation, called scaffolds, of various natural and synthetic, biodegradable and permanent materials, for example, collagen and aliphatic polyesters, on which cells are generally implanted or "seeded" into to allow cell attachment and migration, to deliver and retain cells and biochemical factors, to enable diffusion of vital cell nutrients and expressed products, or to exert certain mechanical and biological influences to modify the behavior of the cell phase, or any combination thereof.

Figure 4:
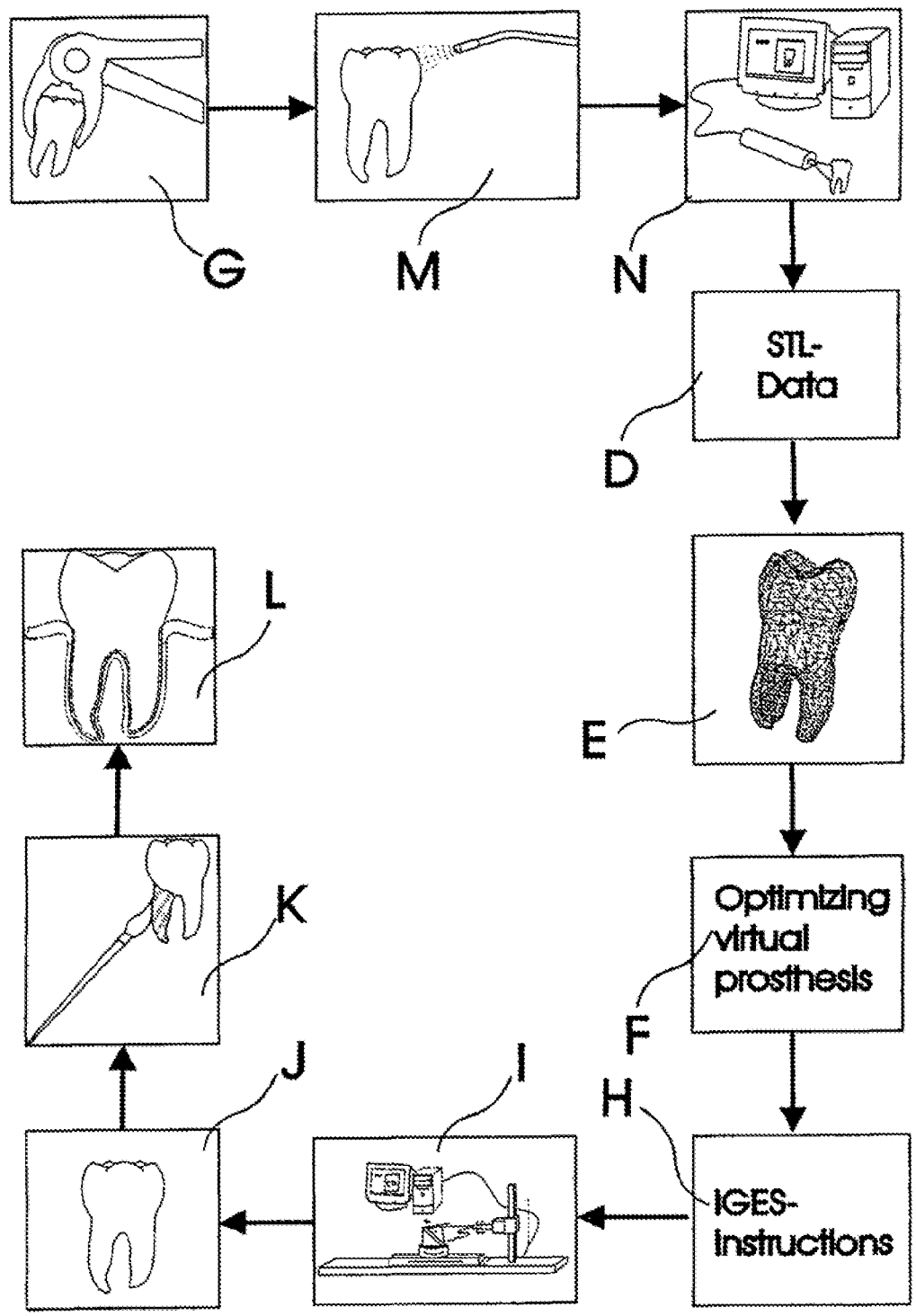
FIG. 4 shows the process steps of extracting the natural tooth, extra-orally acquiring three-dimensional data of that tooth, fabricating an artificial copy and inserting the copy into the socket of the natural tooth according to an embodiment of the present invention.
Figure 51:
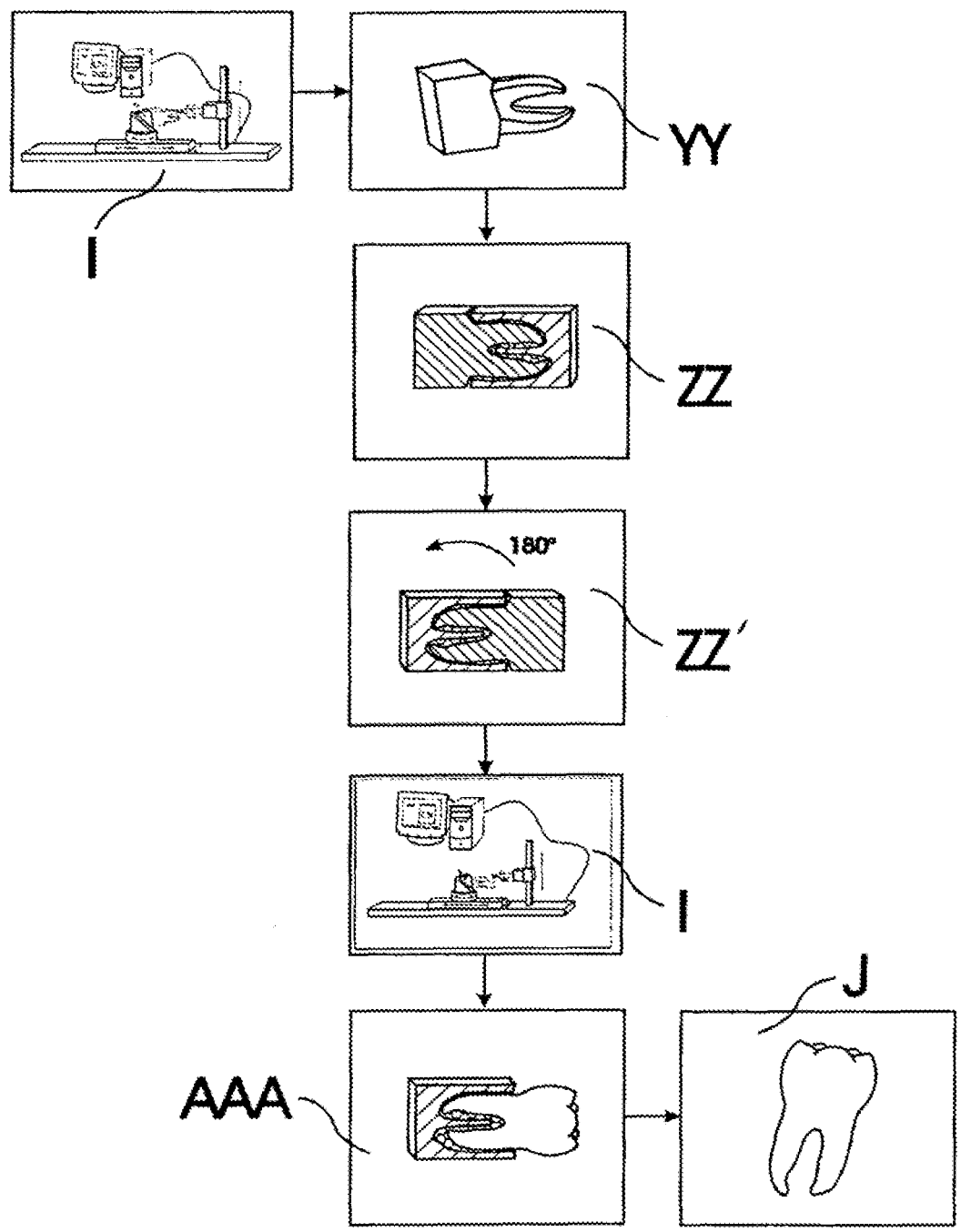
FIG. 51 shows the process steps of fabricating a one-piece prosthesis according to an embodiment of the present invention.

Several figures and several process steps described therein show a prosthesis or parts thereof configured, for example, as a single tooth prosthesis and being manufactured and shaped from all sides (see, e.g., FIG. 100 part 2, FIG. 3 step J, FIG. 4 step J, FIG. 5 step J, FIGS. 6, 7, 8, 9, 10, 11, 12, FIGS. 13/15/16 part 12030 and part 12000, FIG. 17 part 900, FIG. 18 part 9040, FIG. 19 part 9090 and part 12050, FIG. 21 part 16000, FIG. 22, FIG. 31, FIG. 34, FIGS. 35/36 part 12030 and part 12000, FIG. 39 part 200, FIG. 40 part 400, FIG. 41 part 200 and part 200 including 22000, FIG. 42 part 200 and part 200 including 23000, FIG. 43 part 400 and part 24000, FIG. 44 step J and step U, FIG. 45 step I, Z and step M, FIG. step DD). FIG. 51 outlines exemplary process steps. After a design of such prosthesis is obtained and computer numerical control (CNC) data are derived and converted, for example, into the IGES format and transferred to a CAM system for fabricating the prosthesis (step I). The prosthesis is then shaped, for example, in regards to its root portion by milling one side of the workpiece with the result shown in step YY. The side of the workpiece being already shaped will be temporarily embedded in adhesive materials (step ZZ) turned (step ZZ') and fed, positioned, orientated and clamped again into the CAM system (step I) to be shaped, for example, in regards to its crown portion by milling the opponent side to the aforementioned one side with the result as shown in step AAA. After dissolving or otherwise removing the adhesive (shown in step ZZ and AAA) the workpiece, e.g., having been shaped on all sides, is ready for use or for the following process steps of surface of polishing, surface coating by, for example, plasma technologies and tissue engineering. Drug releasing surfaces can be applied or porous surfaces may be loaded with growth hormones, proteins, antibiotic or other substances. It should be noted that although FIG. 51 contemplates interaction with an operator, one skilled in the art would readily appreciate that this functionality may be fully automated.

Note, it should be understood that one of ordinary skill in the art should understand that the various aspects of the present invention, as explained above, can readily be combined with each other.

The meaning of "CAD" shall include, but shall not be limited to, any and all technology of computer aided design.

The meaning of "CAM" shall include, but shall not be limited to, any and all technology of computer aided manufacturing.

The meaning of "CNC" shall include, but shall not be limited to, any and all technology of computer numerical control as it relates to manufacturing machinery and systems, including but not limited to rapid prototyping devices and systems.

The meaning of "rapid prototyping" shall include, but shall not be limited to, technologies qualified for manufacturing of copies of virtual three-dimensional objects and also technologies qualified for mass customization or the mass production of copies of customized or adapted geometries to the needs of an individual patient. Rapid prototyping in this context shall include, but not be limited to, manufacturing technologies based on the digital data, by a process that includes depositing material, in accordance with the digital data, layer-by-layer in a plurality of layers each constituting a two-dimensional cross section of a solid object having an edge defined by data of the three-dimensional surface, the layers being stacked in a third dimension to form the solid object having a three-dimensional surface defined by the data. Such rapid prototyping technologies can be directed to actually manufacturing the part of interest, for example, by selective laser sintering or indirect by fabricating first e.g., a resin or wax sample of the part of interest, and second using, for example, "lost-wax" casing to duplicate such sample and fabricate therewith the part of interest. It also includes sintering techniques where the "green" body is printed in response to computerized numerical controlled (CNC) data and sintered it to its final material properties. Sintering in this context includes pressure and heat.

The meaning of "body" of an artificial tooth shall include, but shall not be limited to, the part of the prosthesis representing a root structure for periodontal or osseointegration or the combined part of the prosthesis representing a root structure for periodontal or osseointegration and a support structure for a crown or a bridge.

The meaning of "prosthesis" shall include any substantially artificially shaped part of any natural and artificial material. In this sense a dental prosthesis for periodontal integration would have to be distinguished to any human tooth used for intentional re-implantation.

Whenever the context requires, the word "prosthesis" shall be deemed to include the word "implant" and vice versa.

3D" shall mean three-dimensional.

The meaning of "CT" shall include, but shall not be limited to, any and all technology of computed tomography.

CBCT" shall mean cone beam computed tomography.

The meaning of "MRT" shall include, but shall not be limited to, any and all technology of magnetic resonance tomography.

The meaning of "TOF" shall include, but shall not be limited to, any and all technology employing time of flight procedures.

The meaning of "imaging" and "scanning" shall include, but shall not be limited to, any and all technology of acquiring two-dimensional and/or three-dimensional data of physical objects or parts of a human body.

The meaning of clinical "imaging data" shall include, but shall not be limited to, in-vivo and in-vitro processes that result in any anatomical data of the anatomy of a human being. In this context the term data shall include, but shall not be limited to, two-dimensional and three-dimensional data.

The meaning of three-dimensional data shall include, but shall not be limited to, surface (e.g., triangulated data) and volumetric (e.g., voxel) data.

The meaning of "periodontal tissue" shall include, but shall not be limited to, any soft tissue surrounding a tooth.

The meaning of "periodontal ligature", "ligament" or "periodontal ligament" shall include, but shall not be limited to, the fibrous connective tissue, e.g., human gingival fibroblasts, interface usually located between a human tooth and the anatomical structure of the jaw of a human being.

The meaning of each one of the following: "periodontal integration", "parodontal integration", "integration into the periodont", "integration into the parodont", "integration into the dental soft-tissue", "integration into the dental ligament" and like word constructions shall include, but shall not be limited to, the integration into the periodontal ligament structure or any other biological structure of the human dental anatomy except osseointegration. In this sense, the term periodontal integration shall include, but shall not be limited to, the integration of the prosthesis to be adopted and held by periodontal ligament tissue of a human being.

In this sense a prostheses for periodontal integration would have to be distinguished from any osseointegrated implant.

The meaning of "cavity" shall include, but shall not be limited to, the periodontal cavity, a cavity of the jaw bone structure, a cavity of the alveolus or a combination thereof.

The meaning of "extraction socket" shall include prepared or unprepared extraction sockets. The meaning of "prepared" shall include, but shall not be limited to, being surgically pared, abraded, scraped or curetted by mechanical instruments or laser technology based devices.

The meaning of "replacement", "to replace", "to be replaced" shall include, but shall not be limited to, any substitution, where one object fills the former position of another object. In the context of the foregoing such substitution can be performed at any time, so that, for example, the term replacement shall not be limited to a replacement in a timely manner.

The meaning of a "manufactured one-piece" object shall not be limited to homogeneous objects, and shall include, but shall not be limited to, manufactured assemblies, objects that are coated, objects that are consisting of more than one pieces or materials bonded together or any combination thereof.

The meaning of a "clinical one-step" process or a "clinical one-step" method shall include, but shall not be limited to, a series clinical process or method steps performed in one or more clinical events as long as no further iteration is required that includes clinical process or method steps and process or method steps that cannot be performed chair-side.

The meaning of "immediate load" of an implant shall include, but shall not be limited to, any all integration concepts of implants where the occlusal portion of the implant (e.g., the crown portion facing the opponent jaw) is not protected against the alternate load of mastication by additional protective means.

The meaning of "configured to be integrated into the existing occlusion of the patients dentition" shall include, but shall not be limited to, any shaping of a crown or a crown-like portion of a prosthesis that contacts or otherwise substantially fills the gap between adjacent crowns, and any shaping that contacts or otherwise substantially interacts with the opponent crowns of the dentition in the process of masticating food.

In dentistry, the term occlusion is used to refer to the manner in which the teeth from upper and lower arches come together when the mouth is closed. The meaning of "occlusion" shall mean, but shall not be limited to, the manner the teeth of the upper or lower arch are fitting and coming in contact with each other while the mouth is closed or during chewing (articulation). It shall also include the fit and contact of adjacent teeth within one arch. The meaning of "integrated into the occlusion" shall include, but shall not be limited to, the configuration and integration of the fit and contact situation of a prosthesis within the existing or new build occlusion within the same and the opponent arch.

The words used in this specification to describe the various exemplary embodiments of the present invention are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word, itself.

The various embodiments of the present invention and aspects of embodiments of the invention disclosed herein are to be understood not only in the order and context specifically described in this specification, but to include any order and any combination thereof. Whenever the context requires, all words used in the singular number shall be deemed to include the plural and vice versa. Words which import one gender shall be applied to any gender wherever appropriate. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

The present application is related to U.S. patent application Ser. No. 11/724,261, titled "Customized Dental Prosthesis for Periodontal- or Osseointegration and Related Systems and Methods," filed on Mar. 15, 2007, and U.S. patent application Ser. No. 11/549,728, filed on Mar. 16, 2006, titled "Customized Dental Prosthesis for Periodontal- or Osseointegration and Related Systems and Methods," each incorporated herein by reference in its entirety.

In the drawings and specification, there have been disclosed embodiments of the present invention, and although specific terms are employed, the terms are used in a descriptive sense only and not for purposes of limitation, the scope of the invention being set forth in the following claims. The invention has been described in considerable detail with, specific reference to the illustrated embodiments. It will be apparent, however, that various modifications and changes can be made within the spirit and scope of the invention as described in the foregoing specification.

That claimed as:

1. A method of manufacturing a dental prosthesis comprising a tooth prosthesis for implantation into a jawbone cavity of a pre-identified patient, the tooth prosthesis comprising a root portion, an occlusally facing portion, and a custom crown portion as an integral part of the tooth prosthesis prior to integrating the tooth prosthesis into an embedding portion of the jawbone cavity of the pre-identified patient, the crown portion comprising or integrated with the occlusally facing portion, the method comprising the steps of:

receiving imaging data describing a three-dimensional shape of an outer surface portion of a root portion of a nonfunctional natural tooth of the pre-identified patient, deriving digital design data defining a three-dimensional shape of an outer surface of a root portion of the tooth prosthesis responsive to the received imaging data, and a three-dimensional shape of an outer surface of an occlusally facing interface of the root portion of the tooth prosthesis to receive the occlusally facing portion of the tooth prosthesis, the three-dimensional shape of the outer surface of the root portion of the tooth prosthesis dimensionally matching a three-dimensional shape of a corresponding outer surface portion of the nonfunctional natural tooth of the pre-identified patient, and the deriving step includes combining a plurality of artificially created surface elements with a plurality of naturally shaped surface elements of the root portion, the plurality of naturally shaped surface elements being selected from the group comprising:

shape elements included in the received imaging data, and shape elements created in close vicinity of surface elements included in the received imaging data;

manufacturing the root portion of the tooth prosthesis at least partially responsive to the digital design data to form at least a substantial portion of the root portion of the tooth prosthesis, to include shaping at least a substantial portion of the outer surface portion of the root portion of the tooth prosthesis to conform with and to substantially dimensionally match the three-dimensional shape of the outer surface of the root portion of the tooth prosthesis derived from the three-dimensional shape of the corresponding outer surface portion of the root portion of the nonfunctional natural tooth, so that the entire outer surface portion of the root portion of the tooth prosthesis that corresponds to an entire embedding jaw bone cavity surface associated with the nonfunctional natural tooth of the pre-identified patient is sized and shaped so as to not exceed dimensionally a natural pre-insertion three-dimensional shape of the respective embedding jaw bone cavity surface when the tooth prosthesis is clinically positioned therein; and manufacturing a custom-shaped dental splint configured to provide temporary primary stability to the tooth prosthesis in a final geometrical relation to the embedding portion of the jawbone cavity of the pre-identified patient, to include the steps of:

receiving imaging data describing a three-dimensional shape and position of an outer surface portion of a crown portion of at least one adjacent tooth immediately adjacent the jawbone cavity of the pre-identified patient to receive the tooth prosthesis in respect to its geometrical relation to the jawbone cavity to receive the tooth prosthesis, deriving digital data defining a custom-shaped splint design of the custom-shaped dental splint responsive to the received imaging data, the custom-shaped dental splint having an elongate tooth-surface contoured body including a tooth-facing outer surface, a non-tooth-facing outer surface opposite the tooth-facing surface, and an outer perimeter surface extending therebetween, the tooth-facing outer surface including a first three-dimensional shape portion dimensioned to substantially match to a three-dimensional shape of a corresponding substantial surface portion of the crown portion of the tooth prosthesis and a second three-dimensional shape portion dimensioned to substantially match to a three-dimensional shape of a corresponding substantial surface portion of the crown portion of the at least one adjacent tooth, the first and the second three-dimensional shape portions having a geometrical relationship configured so that when the first three-dimensional shape portion is affixed to the substantial surface portion of the crown portion of the tooth prosthesis and when the second three-dimensional shape portion is affixed to the substantial surface portion of the crown portion of the at least one adjacent tooth, the custom-shaped dental splint provides temporary primary stability to the tooth prosthesis, maintaining the tooth prosthesis in a final geometrical relation to the embedding portion of the jawbone cavity, the substantial surface portion of the crown portion of the tooth prosthesis and the substantial surface portion of the at least one adjacent tooth matched to the tooth facing second three-dimensional shape portion of the custom-shaped dental splint each comprising one of the following: a labial surface portion and a lingual surface portion, and manufacturing the custom-shaped dental splint at least partially responsive to the derived digital data defining the custom-shaped splint design to form at least a substantial portion of the custom-shaped dental splint.

2. A method as defined in claim 1, wherein the step of manufacturing the custom-shaped dental splint includes deriving numerical control data from the custom-shaped splint design;

wherein a first portion of the numerical control data includes a description of an outer surface portion of the crown portion of the tooth prosthesis corresponding to an outer surface portion of the crown portion of the non-functional natural tooth of the pre-identified patient;

wherein a second portion of the numerical control data includes a description of an outer surface portion of the crown portion of the at least one adjacent functional tooth of the pre-identified patient; and wherein a third portion of the numerical control data includes the description of the final geometrical relation between at least a portion of the crown portion of the tooth prosthesis and at least a portion of the at least one adjacent functional tooth of the pre-identified patient.

3. A method as defined in claim 1, further comprising the step of:

receiving imaging data describing a three-dimensional shape and position of outer surface portions of a crown portion of at least one opponent tooth immediately adjacent the jawbone cavity of the pre-identified patient to receive the tooth prosthesis in respect to its geometrical relation thereto; and wherein the custom-shaped dental splint is shaped to not interfere with the occlusal contact between the crown portion of the at least opponent tooth with the crown portion of the at least one adjacent tooth and the crown portion of the tooth prosthesis.

4. A method as defined in claim 1, wherein the plurality of naturally shaped surface elements of the root portion comprise the shape elements included in the received imaging data.

5. A method as defined in claim 4, wherein the shape elements included in the received imaging data are selected from the group comprising: points, pixels, triangles, splines, voxels, volumetric data representing MRT density values, and volumetric data representing x-ray density values.

6. A method as defined in claim 1, wherein the plurality of naturally shaped surface elements of the root portion include the shape elements created in close vicinity of surface elements included in the received imaging data.

7. A method as defined in claim 1, wherein the step of deriving digital design data defining the three-dimensional shape of the outer surface of the root portion of the tooth prothesis further includes combining the plurality of naturally shaped surface elements of the root portion with artificially created surface elements that deviate substantially from a three-dimensional shape of a corresponding outer surface portion of the root portion of the nonfunctional natural tooth of the pre-identified patient, thereby optimizing the shape of the root portion of the tooth prosthesis for easy insertion.

8. A method as defined in claim 1, wherein the plurality of naturally shaped surface elements of the root portion include the shape elements created in close vicinity of surface elements included in the received imaging data, and wherein the step of deriving digital design data defining the three-dimensional shape of the outer surface of the root portion of the tooth prothesis further includes numerical smoothing processes to define the shape elements created in close vicinity of surface elements included in the imaging data received.

9. A method of manufacturing a tooth prosthesis configured for implantation into a jaw bone cavity of a pre-identified patient and a custom-shaped splint configured to provide temporary primary stability to the tooth prosthesis in a final geometric relationship to an embedding portion of the jawbone cavity of the pre-identified patient, the method comprising the steps of:
  receiving imaging data describing a three-dimensional shape of an outer surface portion of a root portion of a nonfunctional natural tooth of a pre-identified patient, a three-dimensional shape of an outer surface portion of a crown portion of the nonfunctional natural tooth of the pre-identified patient, and a three-dimensional shape and position of an outer surface portion of a crown portion of at least one adjacent tooth immediately adjacent the jawbone cavity of the pre-identified patient to receive the tooth prosthesis in respect to its geometrical relation thereto;
  deriving digital data defining a three-dimensional shape of an outer surface of the root portion of a tooth prosthesis responsive to the received imaging data, the three-dimensional shape of the outer surface of the root portion of the tooth prosthesis dimensionally matching a corresponding three-dimensional shape of a corresponding outer surface portion of the natural tooth of the pre-identified patient;
  manufacturing the tooth prosthesis at least partially responsive to the digital data to form at least a substantial portion of the root portion of the tooth prosthesis;
  deriving digital design data defining a custom-shaped splint design of a custom-shaped splint responsive to the received imaging data, the custom-shaped splint having an elongate tooth-surface contoured body including a tooth-facing outer surface, a non-tooth-facing outer surface opposite the tooth-facing surface, and an outer perimeter surface extending therebetween, the tooth-facing outer surface including a first three-dimensional shape portion dimensioned to substantially match to a three-dimensional shape of a corresponding substantial surface portion of a crown portion of the tooth prosthesis and a second three-dimensional shape portion dimensioned to substantially match to a three-dimensional shape of a corresponding substantial surface portion of the crown portion of the at least one adjacent tooth, the first and the second three-dimensional shape portions having a geometrical relationship so that when the first three-dimensional shape portion is affixed to the substantial surface portion of the crown portion of the tooth prosthesis and when the second three-dimensional shape portion is affixed to the substantial surface portion of the crown portion of the at least one adjacent tooth, the custom-shaped splint provides temporary primary stability to the tooth prosthesis, maintaining the tooth prosthesis in a final geometrical relation to an embedding portion of the jawbone cavity, the substantial surface portion of the at least one adjacent tooth matched to the tooth facing second three-dimensional shape portion of the custom-shaped splint comprising one of the following: a labial surface portion and a lingual surface portion, and
  manufacturing the custom-shaped splint at least partially responsive to the derived digital design data defining the custom-shaped splint to form at least a substantial portion of the custom-shaped splint.

10. A method as defined in claim 9, further comprising the step of:
  receiving imaging data describing a three-dimensional shape and position of an outer surface portion of a crown portion of at least one opponent tooth immediately adjacent the jawbone cavity of the pre-identified patient in respect to its geometrical relation thereto; and
  wherein the custom-shaped splint is shaped to not interfere with the occlusal contact between the crown portion of the at least opponent tooth and the crown portion of the at least one adjacent tooth and the crown portion of the tooth prosthesis.

11. A method as defined in claim 9,
  wherein the three-dimensional shape of the at least a substantial portion of the manufactured root portion of the tooth prosthesis substantially dimensionally matches the three-dimensional shape of a corresponding outer surface portion of the root portion of the nonfunctional natural tooth of the pre-identified patient described by the imaging data; and
  wherein the three-dimensional shape of the at least a substantial portion of a crown portion of the tooth prosthesis substantially dimensionally matches the three-dimensional shape of a corresponding outer surface portion of the crown portion of the nonfunctional natural tooth of the pre-identified patient described by the imaging data.

* * * * *